US007908090B2

(12) United States Patent
Kim et al.

(10) Patent No.: US 7,908,090 B2
(45) Date of Patent: Mar. 15, 2011

(54) SIGNATURES FOR HUMAN AGING

(75) Inventors: Stuart K. Kim, Stanford, CA (US); Jacob M. Zahn, Mountain View, CA (US); Graham Rodwell, Tucson, AZ (US); Art B. Owen, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 995 days.

(21) Appl. No.: 11/605,859

(22) Filed: Nov. 28, 2006

(65) Prior Publication Data

US 2007/0161022 A1 Jul. 12, 2007

Related U.S. Application Data

(60) Provisional application No. 60/741,230, filed on Nov. 30, 2005.

(51) Int. Cl.
*G06G 7/58* (2006.01)
*G01N 33/483* (2006.01)
*C12Q 1/68* (2006.01)

(52) U.S. Cl. .................... 702/19; 703/11; 700/30; 435/6

(58) Field of Classification Search ........................ None
See application file for complete search history.

(56) References Cited

OTHER PUBLICATIONS

Rodwell et al. (PLOS Biology, 2004, 2(12), e427, 2191-2201); including Tables S1-S5.*

Herrero et al. (Bioinformatics, 2001, 17(2), 126-136).*
Ayers et al. (Journal of Clinical Oncology, 2004, 22(12), 2284-2293).*
Lewis et al. (The New England Journal of Medicine, 2001, 345(12), 851-860).*
Mohr et al. (Biochimie, 2004, 86, 13-19).*
Hill, A., et al., "Genomic analysis of gene expression in *C. elegans*," (2000) Science, 290:809-812.
Lee, C., et al, "Gene expression profile of aging and its retardation by caloric restriction," (1999) Science, 285:1390-1393.
Lee, C., et al., "Gene-expression profile of the ageing brain in mice," (2000) Nature Genetics, 25:294-297.
Lund, J., et al., "Transcriptional profile of aging in *C. elegans*," (2002) Current Biology, 12:1566-1573.
Murphy, C., et al., "Genes that act downstream of DAF-16 to influence the lifespan of *Caenorhabditis elegans*," (2003) Nature, 424:277-284.
Pletcher, S., et al., "Genome-wide transcript profiles in aging and calorically restricted *Drosophila melanogaster*," (2002) Current Biology, 12:712-723.
Welle, S., et al., "Gene expression profile of aging in human muscle," (2003) Physiol. Genomics, 14:149-159.
Yoshida, S., et al., "Microarray analysis of gene expresison in the aging human retina," (2002) Investigative Ophthamology & Visual Science, 43(8):2554-2560.
Zou, S., et al., "Genome-wide study of aging and oxidative stress response in *Drosophila melanogaster*," (2000) 97 (25):13726-13731.

* cited by examiner

*Primary Examiner* — Marjorie Moran
*Assistant Examiner* — Larry D Riggs, II
(74) *Attorney, Agent, or Firm* — Bozicevic, Field & Francis LLP; Pamela J. Sherwood

(57) ABSTRACT

Age and related conditions are assessed with a gene expression test that determines the expression levels of a panel of genetic markers. Each age signature contains expression information for genes in at least one functional group that is identified herein as having an expression pattern that correlates with physiological aging of a tissue or tissue of interest.

2 Claims, 5 Drawing Sheets

A.

B.

C.

D.

SIGNATURES FOR HUMAN AGING

INTRODUCTION

This invention was made with Government support under contract 5RO1GM43977 awarded by the National Institutes of Health. The Government has certain rights in this invention.

Aging is marked by the gradual decline of a multitude of physiological functions leading to an increasing probability of death. Some aging-related changes affect one's appearance, such as wrinkled skin, whereas others affect organ function, such as decreased kidney filtration rate and decreased muscular strength.

Aging affects nearly all organisms and is a major risk factor in most human diseases. Recent work has begun to uncover molecular mechanisms that specify lifespan and to identify alterations in cellular physiology that occur at the end of life. For example, oxidative damage caused by the generation of free radicals in the mitochondria has been found to hasten aging by causing an accumulation of damaged cellular components. Telomere shortening may also play a role in aging by preventing DNA replication and cell division in later years. Genetic studies have identified many genes that play a role in specifying lifespan. For example, mutations in yeast sir2 (chromatin regulator), worm daf-2 (insulin-like growth factor receptor), fly methuselah (tyrosine kinase receptor), mouse p53, and the human Werner's syndrome gene (DNA helicase) cause dramatic changes in lifespan. Several aging mechanisms alter longevity in multiple organisms. For example, mutations in the gene encoding insulin-like growth factor receptor alter lifespan in worms, flies, and mice, indicating that an endocrine signaling pathway has a conserved role in aging.

Genetic studies have shown that aging can be slowed in mutants that are defective in a wide range of cellular processes, including mitochondrial function, chromatin regulation, insulin signaling, transcriptional regulation, and genome stability. This indicates that aging is a complex process driven by diverse molecular pathways and biochemical events. As such, a powerful approach to study aging is to use systems biology, which allows a multitude of factors affecting aging to be analyzed in parallel. For example, DNA microarrays and gene expression chips have been used to perform a genome-wide analysis of changes in gene expression in old age. Studies in *Caenorhabditis elegans* and *Drosophila melanogaster* have identified age-regulated genes (Hill et al. (2000) Science 290: 809-812; Zou et al. (2000) PNAS 97: 13726-13731; Lund et al. (2002) Curr Biol 12: 1566-1573; Pletcher et al. (2002) Curr Biol 12: 712-723; Murphy et al. (2003) Nature 424: 277-283.

Several studies have described age-regulated genes in the muscle and brain of mice (see Lee et al. (1999) Science 285: 1390-1393; Lee et al. (2000) Nat Genet 25: 294-297) and the retina and muscle of humans (Yoshida et al. (2002) Invest Ophthalmol Vis Sci 43: 2554-2560; Welle et al. (2003) Physiol Genomics 14: 149-159). These age-regulated genes may serve as markers of aging, enabling one to assess physiological age independently of chronological age. Analysis of the functions of these age-regulated genes has identified specific biochemical mechanisms that change toward the end of life.

At the molecular level, protein and gene expression changes are being assembled that can be used as biomarkers for aging. Biomarkers of aging preferably reflect physiological function, rather than simple chronological age, because individuals age at different rates. In the mouse, changes in the levels of CD4 immunocytes and changes in the expression of cell-cycle genes such as p16INK4a are aging biomarkers, as they predict both the remaining lifespan and the physiological age of the mouse.

The extent to which age-regulation of genetic pathways is specific to a particular tissue or common across many tissues is unknown. Another key issue is whether there are genetic pathways that are commonly age-regulated in different species with vastly different life spans, such as human, mouse, fly and worm. Transcriptional profiles of aging have been performed on both skeletal muscle and brain in the mouse, in *D. melanogaster*, and in *C. elegans*. A comparison of the patterns of gene expression changes during aging in the fly and the worm found that genes encoding mitochondrial components decreased expression with age in both species.

The identification of biomarkers for human aging are of great medical interest, particularly biomarkers that correlate with physiological age, and that are commonly regulated in multiple human tissues. The present invention addresses this issue.

SUMMARY OF THE INVENTION

Sets of genes that provide for human age signatures are identified herein. Each set comprises genes from at least one functional group having an expression pattern that correlates with physiological aging of a tissue or tissue of interest. Physiological aging reflects the physical state of the tissue, and can vary from chronological age. The expression pattern of one or a panel of genes in a functional group is assessed, e.g. by mRNA expression, protein levels, etc., and the resulting dataset provides the age signature.

In one embodiment, the expression pattern of genes in at least one age associated functional group is used to generate a common signature for aging, where the expression pattern is associated with aging across multiple human tissues. Functional groups of the human common signature for aging include the cytosolic ribosome pathway, which increases expression with age; components of the extracellular matrix, which increase expression with age; and the electron transport chain pathway, which decreases expression with age. Tissues for analysis of the common signature can include, without limitation, muscle tissue, brain tissue, and kidney tissue. In other embodiments, the tissue for analysis is other than kidney tissue or brain tissue.

In another embodiment, the expression pattern of genes in at least one identified functional group is used to generate a signature for muscle aging. In addition to the functional groups of the human common signature for aging, functional groups of the human signature for muscle aging include the mRNA splicing and processing pathway, which increases expression with age; and the calcium ion transport pathway, which decreases with age in human muscle.

In another embodiment, the expression pattern of genes in at least one functional group is used to generate a signature for kidney aging. In addition to the functional groups of the human common signature for aging, functional groups of the human signature for kidney aging include maintenance of epithelial polarity, which generally increase expression with aging; ribosomal proteins, which increase expression with aging; and specific transcription factors and signaling pathway components.

In one embodiment of the invention, analysis of the signature for aging in a sample is used in a method of diagnosing physiological age in an individual, or in a tissue. Knowledge of physiological age is useful in providing appropriate medical treatment and prevention, as many diseases are associated with physiological aging. The analysis is also useful in diagnosing the physiological age of tissues, e.g. to evaluate the suitability of organs for transplantation.

Methods of analysis may include, without limitation, establishing a training dataset, and comparing an unknown sample to the training dataset as test datasets, i.e. human age signatures. A training dataset may comprise, without limitation, expression analysis from cells known to be physiologically aged; cells from a non-aged source; cells of defined ages; and the like. The human age signature includes quantitative measure of a panel of expression products from one or more sets of genes, as described above. Expression products include mRNA and the encoded polypeptides. Other methods may utilize decision tree analysis, classification algorithms, regression analysis, and combinations thereof. Alternatively, simple quantitative measure of expression products from a set of genes may be performed, and compared to a reference to determine differential expression.

In other embodiments, analysis of human age signatures is used in a method of screening biologically active agents for efficacy in the treatment of aging. In such methods, cells of interest, e.g. kidney cells, neuronal cells, muscle cells, etc., which may be of a defined age, for example from an elderly cell source, from a non-aged source, etc. are contacted in culture or in vivo with a candidate agent, and the effect on expression of one or more of the markers, particularly a panel of markers, is determined. In another embodiment, analysis of differential expression is used in a method of following therapeutic regimens in patients. In a single time point or a time course, measurements of expression of one or more of the markers, e.g. a panel of markers, is determined when a patient has been exposed to a therapy, which may include a drug, combination of drugs, non-pharmacologic intervention, and the like.

DETAILED DESCRIPTION OF THE EMBODIMENTS

Figure 1:
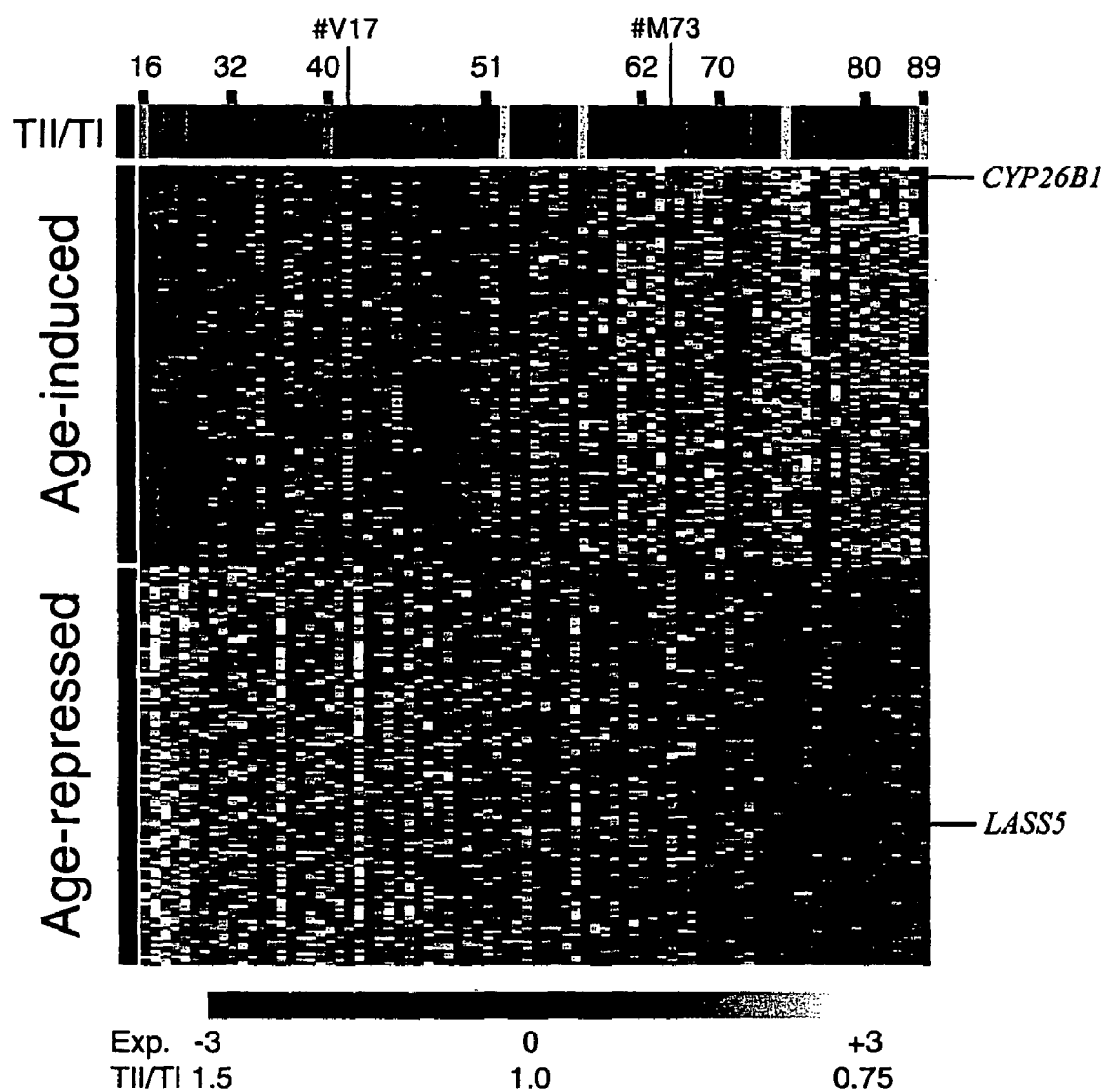
FIG. 1: Expression of 250 age-regulated genes in muscle. Rows correspond to individual genes, arranged in order from greatest increase in expression with age at top to greatest decrease in expression with age at bottom. Columns represent individual patients, from youngest at left to oldest at right. Ages of certain individuals are marked for reference. Scale represents log2 expression level (Exp). Genes discussed in the text are marked for reference.

Age and related conditions are assessed with a gene expression test that determines the expression levels of a panel of genetic markers that provide for a human age signature. Each age signature contains expression information for genes in at least one functional group that is identified herein as having an expression pattern that correlates with physiological aging of a tissue or tissue of interest.

The human age signature provides diagnostic and prognostic methods, by detecting characteristic aging related changes in expression of the indicated genes. The physiological age of an individual, organ, tissue, cell, etc. can be assessed by determining the human age signature. The methods also include screening for efficacy of therapeutic agents and methods; and the like. Early detection can be used to determine the probability of developing certain diseases, thereby allowing for intervention with appropriate preventive or protective measures.

Various techniques and reagents find use in the diagnostic methods of the present invention. In one embodiment of the invention, a tissue or cell samples, or samples derived from such tissues and cells are assayed for the presence of mRNA and/or polypeptides. Expression signatures typically utilize a detection method coupled with analysis of the results to determine if there is a statistically significant match with an age signature.

Chronological Age. The rate of aging is very species specific, where a human may be aged at about 50 years; and a rodent at about 2 years. In general terms, a natural progressive decline in body systems starts in early adulthood, but it becomes most evident several decades later. One arbitrary way to define old age more precisely in humans is to say that it begins at conventional retirement age, around about 60, around about 65 years of age. Another definition sets parameters for aging coincident with the loss of reproductive ability, which is around about age 45, more usually around about 50 in humans, but will, however, vary with the individual.

Physiological age. It has been found that individuals age at different rates, even within a species. Therefore chronological age may be at best imprecise and even misleading as to the extent of decline in function. It is therefore useful to use the methods of the present invention and to evaluate the physiological age of an individual, organ, tissue, cell, etc., rather than the chronological age. In addition to the patterns of gene expression reported herein, there are a number of indicia of physiological aging that are tissue specific.

For example, in muscle tissue, the diameters of the Type I and Type II muscle fibers correlate with physiological age. In kidney tissue, there is a general decline in the morphological appearance of the kidney with age, including a loss of glomerular structure and replacement of capillaries with fibrous tissue; collapse and atrophy of tubules; and thickening of the innermost layer of the arteriole wall due to the accumulation of hyaline material.

In some embodiments, a chronicity index is determined, which index is a quantitative estimate of the morphological appearance and physiological state of the tissue based on such criteria as discussed above.

Human age signature. Human age signatures, e.g. common signature for aging; signature for kidney aging; and signature for muscle aging; comprise a dataset of expression information for genes identified herein as being correlated with physiological age. The term expression profile is used broadly to include a gene expression profile, e.g., an expression profile of mRNAs, or a proteomic expression profile, e.g., an expression profile of one or more different proteins. Profiles may be generated by any convenient means for quantitation, e.g. quantitative hybridization of mRNA, labeled mRNA, amplified mRNA, cRNA, etc., quantitative PCR, ELISA for protein quantitation, antibody arrays, and the like.

Each age signature will include expression information from at least one functional group for the age signature of interest and may include information from two or three functional groups, e.g. the common age signature in cytosolic ribosome pathway, (increases expression with age); components of the extracellular matrix (increases expression with age); electron transport chain pathway, (decreases expression with age). Functional groups specific for muscle aging include mRNA splicing and processing pathway, (increases expression with age); and the calcium ion transport pathway, (decreases with age). Functional groups specific for the human signature for kidney aging include maintenance of epithelial polarity, (increase expression with aging); and specific transcription factors and signaling pathway components.

Within a functional group, quantitative information is obtained from a sufficient number of genes to provide statistically significant information. Usually expression information from at least about 5 genes in a group is obtained, and the signature may include expression information from about 10, 15, 20, 25, 30 or more genes. In some embodiments the genes are selected based on significance rank (as shown in Table 1, for example), where the highest ranking 5, 10, 15, 20, 25, 30 or more sequences are selected.

The expression profile may be generated from a biological sample using any convenient protocol. Samples can be obtained from the tissues or fluids of an individual, as well as from organs, tissues, cell cultures or tissue homogenates, etc. For example, samples can be obtained from whole blood, tissue biopsy, serum, etc. Also included in the term are derivatives and fractions of such cells and fluids. Where cells are analyzed, the number of cells in a sample can be at least about $10^2$, at least $10^3$, and may be about $10^4$ or more. The cells may be dissociated, in the case of solid tissues, or tissue sections may be analyzed. Alternatively a lysate of the cells may be prepared.

Following obtainment of the expression profile from the sample being assayed, the expression profile is compared with a reference or control profile to make a assessment regarding the physiological age of the cell or tissue from which the sample was obtained/derived. Typically a comparison is made with a signature from a sample of known physiological age, e.g. an aged sample, a young sample, and the like. Usually for diagnostic or prognostic methods, a determined value or test value is statistically compared against a reference or baseline value.

In certain embodiments, the obtained signature is compared to a single reference/control profile to obtain information regarding the phenotype of the cell/tissue being assayed. In other embodiments, the obtained signature is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The difference values, i.e. the difference in expression with age, may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above. A statistical analysis step is then performed to obtain the weighted contribution of the set of predictive genes.

Diagnostic Algorithms. An algorithm that combines the results of multiple expression level determinations that will discriminate robustly between aged and non-aged tissues or cells, and controls for confounding variables and evaluating potential interactions is used for diagnostic purposes.

In such an algorithm, an age dataset is obtained. The dataset comprises quantitative data for a human age signature as described above.

In order to identify profiles that are indicative of a sample age, a statistical test will provide a confidence level for a change in the biomarkers between the test and control profiles to be considered significant. The raw data may be initially analyzed by measuring the values for each marker, usually in triplicate or in multiple triplicates.

A test dataset is considered to be different than the normal control if at least one, usually at least five, at least ten, at least 15, 20, 25 or more of the parameter values of the profile exceeds the limits that correspond to a predefined level of significance.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001)

PNAS 98, 5116-21, herein incorporated by reference). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data may be subjected to non-supervised hierarchical clustering to reveal relationships among profiles. For example, hierarchical clustering may be performed, where the Pearson correlation is employed as the clustering metric. One approach is to consider a patient age dataset as a "learning sample" in a problem of "supervised learning". CART is a standard in applications to medicine (Singer (1999) Recursive Partitioning in the Health Sciences, Springer), which may be modified by transforming any qualitative features to quantitative features; sorting them by attained significance levels, evaluated by sample reuse methods for Hotelling's T2 statistic; and suitable application of the lasso method. Problems in prediction are turned into problems in regression without losing sight of prediction, indeed by making suitable use of the Gini criterion for classification in evaluating the quality of regressions.

This approach has led to what is termed FlexTree (Huang (2004) PNAS 101:10529-10534). FlexTree has performed very well in simulations and when applied to SNP and other forms of data. Software automating FlexTree has been developed. Alternatively LARTree or LART may be used Fortunately, recent efforts have led to the development of such an approach, termed LARTree (or simply LART) Turnbull (2005) Classification Trees with Subset Analysis Selection by the Lasso, Stanford University. The name reflects binary trees, as in CART and FlexTree; the lasso, as has been noted; and the implementation of the lasso through what is termed LARS by Efron et al. (2004) Annals of Statistics 32:407-451. See, also, Huang et al. (2004) Tree-structured supervised learning and the genetics of hypertension. Proc Natl Acad Sci U S A. 101(29):10529-34.

Other methods of analysis that may be used include logic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as PAM software and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome.

These statistical tools are applicable to all manner of genetic or proteomic data. A set of biomarker, clinical and/or genetic data that can be easily determined, and that is highly informative regarding assessment of physiological age of individuals or tissues, organs, cells, etc., thereof are provided.

Also provided are databases of expression profiles of age signature. Such databases will typically comprise expression profiles of individuals of specific ages, negative expression profiles, etc., where such profiles are as described above.

The analysis and database storage may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

Common human signature for aging. In one embodiment, the expression pattern of genes in at least one of the functional groups is used to generate a common signature for aging across multiple human tissues. Functional groups of the human common signature for aging include the cytosolic ribosome pathway, which increases expression with age; components of the extracellular matrix, which increase expression with age; and the electron transport chain pathway, which decreases expression with age. Tissues for analysis of the common signature can include, without limitation, muscle tissue, brain tissue, and kidney tissue. In other embodiments, the tissue for analysis is other than kidney tissue or brain tissue. Genes associated with aging in multiple tissues include those set forth in Table 1.

TABLE 1

| | Gene Name | Ranks | GenBank Accession |
|---|---|---|---|
| Cytosolic Ribosome | | | |
| RPS4Y1 | ribosomal protein S4, Y-linked | 1 | gi: 4506726 |
| RPS27L | ribosomal protein S27-like | 2 | gi: 7705705 |
| RPS19 | ribosomal protein S19 | 3 | gi: 12652562 |
| RPL28 | ribosomal protein L28 | 4 | gi: 4506626 |
| RPL12 | ribosomal protein L12 | 5 | gi: 749860 |
| RPL18A | ribosomal protein L18a | 6 | gi: 11415025 |
| RPL30 | ribosomal protein L30 | 7 | gi: 388034 |
| RPL19 | ribosomal protein L19 | 8 | gi: 4506608 |
| RPL36 | ribosomal protein L36 | 9 | gi: 7661637 |
| RPL14 | ribosomal protein L14 | 10 | gi: 608516 |
| RPL37 | ribosomal protein L37 | 11 | gi: 11110287 |
| RPS24 | ribosomal protein S24 | 12 | gi: 21753704 |
| RPL34 | ribosomal protein L34 | 13 | gi: 4506636 |
| RPL35 | ribosomal protein L35 | 14 | gi: 6005859 |
| RPL36AL | ribosomal protein L36a-like | 15 | gi: 10445222 |
| RPS27A | ribosomal protein S27a | 16 | gi: 4506712 |
| RPL27 | ribosomal protein L27 | 17 | gi: 4506622 |
| RPS25 | ribosomal protein S25 | 18 | gi: 3004063 |
| RPS17 | ribosomal protein S17 | 19 | gi: 4506692 |
| RPL13 | ribosomal protein L13 | 20 | gi: 13289968 |
| RPL36A | ribosomal protein L36a | 21 | gi: 3036783 |
| RPL10A | ribosomal protein L10a | 22 | gi: 6325471 |
| RPL27A | ribosomal protein L27a | 23 | gi: 4506624 |
| RPS6 | ribosomal protein S6 | 24 | gi: 4506730 |
| RPS15A | ribosomal protein S15a | 25 | gi: 4506688 |
| RPL23A | ribosomal protein L23a | 26 | gi: 1399085 |
| RPL11 | ribosomal protein L11 | 27 | gi: 4506594 |
| RPS11 | ribosomal protein S11 | 28 | gi: 4506680 |
| RPL35A | ribosomal protein L35a | 29 | gi: 10579506 |
| RPL21 | ribosomal protein L21 | 30 | gi: 10045426 |
| RPL13A | ribosomal protein L13a | 31 | gi: 12653484 |
| RPS10 | ribosomal protein S10 | 32 | gi: 1973113 |
| RPS21 | ribosomal protein S21 | 33 | gi: 4506698 |
| RPS7 | ribosomal protein S7 | 34 | gi: 5392153 |
| RPS3 | ribosomal protein S3 | 35 | gi: 555940 |
| RPS12 | ribosomal protein S12 | 36 | gi: 5364479 |
| RPL18 | ribosomal protein L18 | 37 | gi: 4506606 |
| RPS13 | ribosomal protein S13 | 38 | gi: 4506684 |
| RPL24 | ribosomal protein L24 | 39 | gi: 4510914 |
| RPS9 | ribosomal protein S9 | 40 | gi: 21754245 |
| RPLP1 | ribosomal protein, large, P1 | 41 | gi: 4506668 |
| RPL38 | ribosomal protein L38 | 42 | gi: 12653644 |
| RPS16 | ribosomal protein S16 | 43 | gi: 4506690 |
| RPLP2 | ribosomal protein, large P2 | 44 | gi: 4506670 |
| RPL32 | ribosomal protein L32 | 45 | gi: 4506634 |
| RPL7A | ribosomal protein L7a | 46 | gi: 4506660 |
| RPS28 | ribosomal protein S28 | 47 | gi: 11443477 |
| RPS8 | ribosomal protein S8 | 48 | gi: 4506742 |
| RPL26L1 | ribosomal protein L26-like 1 | 49 | gi: 7705812 |
| RPS20 | ribosomal protein S20 | 50 | gi: 21753754 |

TABLE 1-continued

| Gene Name | | Ranks | GenBank Accession |
|---|---|---|---|
| RPL5 | ribosomal protein L5 | 51 | gi: 820419 |
| RPS5 | ribosomal protein S5 | 52 | gi: 4506728 |
| RPP38 | ribonuclease P/MRP 38 kDa subunit | 53 | gi: 5454025 |
| RPL10 | ribosomal protein L10 | 54 | gi: 21284401 |
| RPLP0 | ribosomal protein, large, P0 | 55 | gi: 4506666 |
| RPS27 | ribosomal protein S27 (metallopanstimulin 1) | 56 | gi: 4506710 |
| RPL37A | ribosomal protein L37a | 57 | gi: 4506642 |
| RPS29 | ribosomal protein S29 | 58 | gi: 4506716 |
| RPS14 | ribosomal protein S14 | 59 | gi: 7959918 |
| RPL29 | ribosomal protein L29 | 60 | gi: 4506628 |
| RPL17 | ribosomal protein L17 | 61 | gi: 4506616 |
| RPS23 | ribosomal protein S23 | 62 | gi: 4506700 |
| RPS15 | ribosomal protein S15 | 63 | gi: 13623622 |
| RPL3 | ribosomal protein L3 | 64 | gi: 4506648 |
| RPL4 | ribosomal protein L4 | 65 | gi: 5746196 |
| RPL23 | ribosomal protein L23 | 66 | gi: 4506604 |
| RPL31 | ribosomal protein L31 | 67 | gi: 4085216 |
| RPL14 | ribosomal protein L14 | 68 | gi: 608516 |
| RPL15 | ribosomal protein L15 | 69 | gi: 4455632 |
| RPL9 | ribosomal protein L9 | 70 | gi: 4506664 |
| RPL26 | ribosomal protein L26 | 71 | gi: 6855342 |
| RPL8 | ribosomal protein L8 | 72 | gi: 4506662 |
| RPL41 | ribosomal protein L41 | 73 | gi: 10863874 |
| RPS4X | ribosomal protein S4, X-linked | 74 | gi: 4506724 |
| RPL10L | ribosomal protein L10-like | 75 | gi: 3202255 |
| RPS2 | ribosomal protein S2 | 76 | gi: 4506718 |
| RPL7 | ribosomal protein L7 | 77 | gi: 4506658 |
| RPS18 | ribosomal protein S18 | 78 | gi: 11968181 |
| RPL6 | ribosomal protein L6 | 79 | gi: 4506656 |
| RPL39 | ribosomal protein L39 | 80 | gi: 12654388 |
| RPS26 | ribosomal protein S26 | 81 | gi: 4506708 |
| RPS3A | ribosomal protein S3A | 82 | gi: 9795038 |
| RPL22 | ribosomal protein L22 | 83 | gi: 409069 |
| RPL3L | ribosomal protein L3-like | 84 | gi: 4826987 |
| RPL39L | ribosomal protein L39-like | 85 | gi: 388035 |
| Extracellular Matrix | | | |
| TIMP1 | tissue inhibitor of metalloproteinase 1 (erythroid potentiating activity, collagenase inhibitor) | 1 | gi: 4507508 |
| TFPI2 | tissue factor pathway inhibitor 2 | 2 | gi: 12933969 |
| TNC | tenascin C (hexabrachion) | 3 | gi: 4504548 |
| EFEMP1 | EGF-containing fibulin-like extracellular matrix protein 1 | 4 | gi: 5447470 |
| SPP1 | secreted phosphoprotein 1 (osteopontin, bone sialoprotein I, early T-lymphocyte activation 1) | 5 | gi: 3885365 |
| CSPG2 | chondroitin sulfate proteoglycan 2 (versican) | 6 | gi: 11682587 |
| MMP7 | matrix metalloproteinase 7 (matrilysin, uterine) | 7 | gi: 13027804 |
| MMP13 | matrix metalloproteinase 13 (collagenase 3) | 8 | gi: 13027796 |
| CTGF | connective tissue growth factor | 9 | gi: 180923 |
| VWF | von Willebrand factor | 10 | gi: 9257255 |
| CHI3L1 | chitinase 3-like 1 (cartilage glycoprotein-39) | 11 | gi: 348911 |
| THBS2 | thrombospondin 2 | 12 | gi: 4507486 |
| TGFBI | transforming growth factor, beta-induced, 68 kDa | 13 | gi: 4507466 |
| ADAMTS1 | a disintegrin-like and metalloprotease (reprolysin type) with thrombospondin type 1 motif, 1 | 14 | gi: 10435838 |
| POSTN | periostin, osteoblast specific factor | 15 | gi: 23345099 |
| COMP | cartilage oligomeric matrix protein | 16 | gi: 4557482 |
| THBS4 | thrombospondin 4 | 17 | gi: 4507488 |
| ZP2 | zona pellucida glycoprotein 2 (sperm receptor) | 18 | gi: 4508044 |
| ECM2 | extracellular matrix protein 2, female organ and adipocyte specific | 19 | gi: 4326141 |
| LTBP1 | latent transforming growth factor beta binding protein 1 | 20 | gi: 5813397 |
| LUM | lumican | 21 | gi: 4505046 |
| MGP | matrix Gla protein | 22 | gi: 4505178 |
| BGN | biglycan | 23 | gi: 12803216 |
| LAMA2 | laminin, alpha 2 (merosin, congenital muscular dystrophy) | 24 | gi: 4557708 |
| TIMP2 | tissue inhibitor of metalloproteinase 2 | 25 | gi: 9257247 |
| SPARCL1 | SPARC-like 1 (mast9, hevin) | 26 | gi: 4758521 |
| TIMP4 | tissue inhibitor of metalloproteinase 4 | 27 | gi: 4507514 |
| FBN1 | fibrillin 1 (Marfan syndrome) | 28 | gi: 3872399 |
| GPC4 | glypican 4 | 29 | gi: 3420276 |
| LAMA5 | laminin, alpha 5 | 30 | gi: 13097167 |
| MATN3 | matrilin 3 | 31 | gi: 13518040 |
| FLRT3 | fibronectin leucine rich transmembrane protein 3 | 32 | gi: 7019382 |
| COL9A3 | collagen, type IX, alpha 3 | 33 | gi: 4502966 |
| FBLN1 | fibulin 1 | 34 | gi: 4503662 |

TABLE 1-continued

| Gene Name | | Ranks | GenBank Accession |
|---|---|---|---|
| COL17A1 | collagen, type XVII, alpha 1 | 35 | gi: 4502942 |
| COL6A3 | collagen, type VI, alpha 3 | 36 | gi: 4758027 |
| MATN2 | matrilin 2 | 37 | gi: 13518036 |
| FMOD | fibromodulin | 38 | gi: 5016093 |
| THBS1 | thrombospondin 1 | 39 | gi: 5398596 |
| LTBP2 | latent transforming growth factor beta binding protein 2 | 40 | gi: 4557732 |
| DGCR6 | DiGeorge syndrome critical region gene 6 | 41 | gi: 5031662 |
| LAMC1 | laminin, gamma 1 (formerly LAMB2) | 42 | gi: 186916 |
| COL6A2 | collagen, type VI, alpha 2 | 43 | gi: 13603393 |
| ADAMTS5 | a disintegrin-like and metalloprotease (reprolysin type) with thrombospondin type 1 motif, 5 (aggrecanase-2) | 44 | gi: 14806159 |
| MMRN2 | multimerin 2 | 45 | gi: 13376090 |
| MMP17 | matrix metalloproteinase 17 (membrane-inserted) | 46 | gi: 7706618 |
| KAL1 | Kallmann syndrome 1 sequence | 47 | gi: 4557682 |
| FLRT2 | fibronectin leucine rich transmembrane protein 2 | 48 | gi: 6808604 |
| DAG1 | dystroglycan 1 (dystrophin-associated glycoprotein 1) | 49 | gi: 4758115 |
| LAMB2 | laminin, beta 2 (laminin S) /// laminin, beta 2 (laminin S) | 50 | gi: 663206 |
| MMP2 | matrix metalloproteinase 2 (gelatinase A, 72 kDa gelatinase, 72 kDa type IV collagenase) | 51 | gi: 16553445 |
| GPC6 | glypican 6 | 52 | gi: 4877642 |
| SOD3 | superoxide dismutase 3, extracellular | 53 | gi: 4507150 |
| MMP3 | matrix metalloproteinase 3 (stromelysin 1, progelatinase) | 54 | gi: 13027803 |
| DCN | decorin | 55 | gi: 5532410 |
| MMP9 | matrix metalloproteinase 9 (gelatinase B, 92 kDa gelatinase, 92 kDa type IV collagenase) | 56 | gi: 4826835 |
| MMP20 | matrix metalloproteinase 20 (enamelysin) | 57 | gi: 13027805 |
| TNA | tetranectin (plasminogen binding protein) | 58 | gi: 4507556 |
| DMP1 | dentin matrix acidic phosphoprotein | 59 | gi: 4758171 |
| EMILIN1 | elastin microfibril interfacer 1 | 60 | gi: 5901943 |
| COL9A2 | collagen, type IX, alpha 2 | 61 | gi: 5054578 |
| MATN1 | matrilin 1, cartilage matrix protein | 62 | gi: 180651 |
| MMP23B | matrix metalloproteinase 23B | 63 | gi: 4758729 |
| DPT | dermatopontin | 64 | gi: 4755134 |
| ADAMTS2 | a disintegrin-like and metalloprotease (reprolysin type) with thrombospondin type 1 motif, 2 | 65 | gi: 7656866 |
| NTN2L | netrin 2-like (chicken) | 66 | gi: 5453809 |
| ADAMTS17 | a disintegrin-like and metalloprotease (reprolysin type) with thrombospondin type 1 motif, 17 | 67 | gi: 21265063 |
| ADAMTS20 | a disintegrin-like and metalloprotease (reprolysin type) with thrombospondin type 1 motif, 20 | 68 | gi: 28460689 |
| ADAMTS15 | a disintegrin-like and metalloprotease (reprolysin type) with thrombospondin type 1 motif, 15 | 69 | gi: 21265057 |
| GPC5 | glypican 5 /// glypican 5 | 70 | gi: 5360214 |
| FBLN2 | fibulin 2 /// fibulin 2 | 71 | gi: 4503664 |
| EMILIN2 | elastin microfibril interfacer 2 | 72 | gi: 5912156 |
| ADAMTS19 | a disintegrin-like and metalloprotease (reprolysin type) with thrombospondin type 1 motif, 19 | 73 | gi: 19525736 |
| MFAP1 | microfibrillar-associated protein 1 | 74 | gi: 5174552 |
| ADAMTS14 | a disintegrin-like and metalloprotease (reprolysin type) with thrombospondin type 1 motif, 14 | 75 | gi: 1367622 |
| TNXB | tenascin XB | 76 | gi: 1688079 |
| ADAMTS6 | a disintegrin-like and metalloprotease (reprolysin type) with thrombospondin type 1 motif, 6 | 77 | gi: 7656868 |
| MFAP3 | microfibrillar-associated protein 3 | 78 | gi: 21314642 |
| TIMP3 | tissue inhibitor of metalloproteinase 3 (Sorsby fundus dystrophy, pseudoinflammatory) | 79 | gi: 11294684 |
| NYX | nyctalopin | 80 | gi: 11993320 |
| ADAMTS10 | a disintegrin-like and metalloprotease (reprolysin type) with thrombospondin type 1 motif, 10 | 81 | gi: 3401627 |
| OMD | osteomodulin | 82 | gi: 5232317 |
| WNT3 | wingless-type MMTV integration site family, member 3 / | 83 | gi: 13540476 |
| ADAMTS12 | a disintegrin-like and metalloprotease (reprolysin type) with thrombospondin type 1 motif, 12 | 84 | gi: 13569927 |
| LTBP4 | latent transforming growth factor beta binding protein 4 | 85 | gi: 4505036 |
| MMP15 | matrix metalloproteinase 15 (membrane-inserted) | 86 | gi: 4505210 |
| LAMB3 | laminin, beta 3 | 87 | gi: 510702 |
| AMBN | ameloblastin, enamel matrix protein | 88 | gi: 9665251 |
| COL14A1 | collagen, type XIV, alpha 1 (undulin) | 89 | gi: 11515232 |
| USH2A | Usher syndrome 2A (autosomal recessive, mild) | 90 | gi: 6005935 |
| ADAMTS7 | a disintegrin-like and metalloprotease (reprolysin type) with thrombospondin type 1 motif, 7 | 91 | gi: 10645198 |
| ADAMTS13 | a disintegrin-like and metalloprotease (reprolysin type) with thrombospondin type 1 motif, 13 | 92 | gi: 8922117 |
| ADAMTS4 | a disintegrin-like and metalloprotease (reprolysin type) with thrombospondin type 1 motif, 4 | 93 | gi: 21410062 |
| OPTC | opticin | 94 | gi: 5639938 |
| RBP3 | retinol binding protein 3, interstitial | 95 | gi: 186542 |

TABLE 1-continued

| Gene Name | | Ranks | GenBank Accession |
|---|---|---|---|
| PRELP | proline arginine-rich end leucine-rich repeat protein | 96 | gi: 4506040 |
| MMPL1 | matrix metalloproteinase-like 1 | 97 | gi: 4758727 |
| GPC2 | glypican 2 (cerebroglycan) | 98 | gi: 5527371 |
| MMP27 | matrix metalloproteinase 27 | 99 | gi: 11545844 |
| EMID2 | EMI domain containing 2 | 100 | gi: 10155424 |
| KERA | keratocan | 101 | gi: 8659566 |
| MEPE | matrix, extracellular phosphoglycoprotein with ASARM motif (bone) | 102 | gi: 9910429 |
| DSPP | dentin sialophosphoprotein | 103 | gi: 4322669 |
| GPC3 | glypican 3 | 104 | gi: 1237180 |
| LAMC3 | laminin, gamma 3 | 105 | gi: 5174492 |
| EMID1 | EMI domain containing 1 | 106 | gi: 21732418 |
| MMP16 | matrix metalloproteinase 16 (membrane-inserted) | 107 | gi: 1710273 |
| AMELX | amelogenin (amelogenesis imperfecta 1, X-linked) | 108 | gi: 4502072 |
| MMP28 | matrix metalloproteinase 28 | 109 | gi: 13236529 |
| ENAM | enamelin | 110 | gi: 12002215 |
| NTNG1 | netrin G1 | 111 | gi: 7662425 |
| MMP24 | matrix metalloproteinase 24 (membrane-inserted) | 112 | gi: 13027806 |
| CHAD | chondroadherin | 113 | gi: 4502798 |
| COL9A1 | collagen, type IX, alpha 1 | 114 | gi: 15929965 |
| COL6A1 | collagen, type VI, alpha 1 | 115 | gi: 3649060 |
| SPG7 | spastic paraplegia 7, paraplegin (pure and complicated autosomal recessive) | 116 | gi: 4507172 |
| HAS1 | hyaluronan synthase 1 | 117 | gi: 4504338 |
| ASPN | asporin (LRR class 1) | 118 | gi: 8923132 |
| TECTA | tectorin alpha | 119 | gi: 4885626 |
| NTN1 | netrin 1 | 120 | gi: 4758839 |
| PI3 | protease inhibitor 3, skin-derived (SKALP) | 121 | gi: 4505786 |
| MMP25 | matrix metalloproteinase 25 | 122 | gi: 13027808 |
| SPOCK | sparc/osteonectin, cwcv and kazal-like domains proteoglycan (testican) | 123 | gi: 7248844 |
| ECM1 | extracellular matrix protein 1 | 124 | gi: 1488323 |
| DSPG3 | dermatan sulfate proteoglycan 3 | 125 | gi: 10938018 |
| MMP10 | matrix metalloproteinase 10 (stromelysin 2) | 126 | gi: 4505204 |
| GPC1 | glypican 1 | 127 | gi: 4095017 |
| MMP12 | matrix metalloproteinase 12 (macrophage elastase) | 128 | gi: 4505206 |
| LAMA3 | laminin, alpha 3 | 129 | gi: 19691410 |
| CLECSF1 | C-type (calcium dependent, carbohydrate-recognition domain) lectin, superfamily member 1 (cartilage-derived) | 130 | gi: 10321450 |
| MMP1 | matrix metalloproteinase 1 (interstitial collagenase) | 131 | gi: 13027798 |
| ADAMTS8 | a disintegrin-like and metalloprotease (reprolysin type) with thrombospondin type 1 motif, 8 | 132 | gi: 5901889 |
| ADAMTS9 | a disintegrin-like and metalloprotease (reprolysin type) with thrombospondin type 1 motif, 9 | 133 | gi: 27463364 |
| SPOCK2 | sparc/osteonectin, cwcv and kazal-like domains proteoglycan (testican) 2 | 134 | gi: 5744319 |
| ADAMTS3 | a disintegrin-like and metalloprotease (reprolysin type) with thrombospondin type 1 motif, 3 | 135 | gi: 2224672 |
| MMP26 | matrix metalloproteinase 26/ | 136 | gi: 13027810 |
| LAMB4 | laminin, beta 4 | 137 | gi: 4508116 |
| MMP19 | matrix metalloproteinase 19 | 138 | gi: 13027788 |
| HAPLN2 | hyaluronan and proteoglycan link protein 2 | 139 | gi: 11141886 |
| MMP11 | matrix metalloproteinase 11 (stromelysin 3) | 140 | gi: 5177469 |
| FBN2 | fibrillin 2 (congenital contractural arachnodactyly) | 141 | gi: 10732615 |
| CD164L1 | CD164 sialomucin-like 1 | 142 | gi: 9966884 |
| ELN | elastin (supravalvular aortic stenosis, Williams-Beuren syndrome) | 143 | gi: 2207834 |
| FLRT1 | fibronectin leucine rich transmembrane protein 1 | 144 | gi: 6808602 |
| NTN4 | netrin 4 | 145 | gi: 11120047 |
| LOX | lysyl oxidase | 146 | gi: 4505008 |
| ZP4 | zona pellucida glycoprotein 4 | 147 | gi: 10863986 |
| HAPLN1 | hyaluronan and proteoglycan link protein 1 | 148 | gi: 1151008 |
| MMP8 | matrix metalloproteinase 8 (neutrophil collagenase) | 149 | gi: 4505220 |
| LAMB1 | laminin, beta 1 | 150 | gi: 4504950 |
| AGC1 | aggrecan 1 (chondroitin sulfate proteoglycan 1, large aggregating proteoglycan, antigen identified by monoclonal antibody A0122) | 151 | gi: 22209082 |
| MMP21 | matrix metalloproteinase 21 | 152 | gi: 22218340 |
| Electron Transport Chain | | | |
| ATP5A1 | ATP synthase, H+ transporting, mitochondrial F1 complex, alpha subunit, isoform 1, cardiac muscle | 1 | gi: 23958695 |
| ATP5G3 | ATP synthase, H+ transporting, mitochondrial F0 complex, subunit c (subunit 9) isoform 3 | 2 | gi: 4502300 |

TABLE 1-continued

| Gene Name | | Ranks | GenBank Accession |
|---|---|---|---|
| UQCRFS1 | ubiquinol-cytochrome c reductase, Rieske iron-sulfur polypeptide 1 | 3 | gi: 12653726 |
| NDUFB6 | NADH dehydrogenase (ubiquinone) 1 beta subcomplex, 6, 17 kDa | 4 | gi: 23240290 |
| NDUFV1 | NADH dehydrogenase (ubiquinone) flavoprotein 1, 51 kDa | 5 | gi: 5138911 |
| UQCRC1 | ubiquinol-cytochrome c reductase core protein I | 6 | gi: 4507840 |
| COX5A | cytochrome c oxidase subunit Va | 7 | gi: 4758037 |
| NDUFS1 | NADH dehydrogenase (ubiquinone) Fe—S protein 1, 75 kDa (NADH-coenzyme Q reductase) | 8 | gi: 21618534 |
| COX7B | cytochrome c oxidase subunit VIIb | 9 | gi: 4502990 |
| NDUFS2 | NADH dehydrogenase (ubiquinone) Fe—S protein 2, 49 kDa (NADH-coenzyme Q reductase) | 10 | gi: 4758785 |
| NDUFAB1 | NADH dehydrogenase (ubiquinone) 1, alpha/beta subcomplex, 1, 8 kDa | 11 | gi: 4826851 |
| NDUFA5 | NADH dehydrogenase (ubiquinone) 1 alpha subcomplex, 5, 13 kDa | 12 | gi: 13699821 |
| ATP5J | ATP synthase, H+ transporting, mitochondrial F0 complex, subunit F6 | 13 | gi: 4502292 |
| UCP3 | uncoupling protein 3 (mitochondrial, proton carrier) | 14 | gi: 13259545 |
| NDUFB5 | NADH dehydrogenase (ubiquinone) 1 beta subcomplex, 5, 16 kDa | 15 | gi: 4505362 |
| ATP5H | ATP synthase, H+ transporting, mitochondrial F0 complex, subunit d | 16 | gi: 9970327 |
| ATP5C1 | ATP synthase, H+ transporting, mitochondrial F1 complex, gamma polypeptide 1 | 17 | gi: 4885078 |
| NDUFA6 | NADH dehydrogenase (ubiquinone) 1 alpha subcomplex, 6, 14 kDa | 18 | gi: 12803858 |
| UQCRC2 | ubiquinol-cytochrome c reductase core protein II | 19 | gi: 4507842 |
| COX8A | cytochrome c oxidase subunit 8A | 20 | gi: 4758043 |
| COX7A3 | cytochrome c oxidase subunit VIIa polypeptide 3 (liver) | 21 | gi: 3041843 |
| NDUFA9 | NADH dehydrogenase (ubiquinone) 1 alpha subcomplex, 9, 39 kDa | 22 | gi: 5326822 |
| UQCRH | ubiquinol-cytochrome c reductase hinge protein | 23 | gi: 5174744 |
| NDUFS4 | NADH dehydrogenase (ubiquinone) Fe—S protein 4, 18 kDa (NADH-coenzyme Q reductase) | 24 | gi: 21104473 |
| COX5B | cytochrome c oxidase subunit Vb | 25 | gi: 4502982 |
| COX11 | COX11 homolog, cytochrome c oxidase assembly protein (yeast) | 26 | gi: 4758033 |
| COX6C | cytochrome c oxidase subunit VIc | 27 | gi: 4758039 |
| ATP5G1 | ATP synthase, H+ transporting, mitochondrial F0 complex, subunit c (subunit 9), isoform 1 | 28 | gi: 5262506 |
| NDUFV2 | NADH dehydrogenase (ubiquinone) flavoprotein 2, 24 kDa | 29 | gi: 10835024 |
| NDUFS7 | NADH dehydrogenase (ubiquinone) Fe—S protein 7, 20 kDa (NADH-coenzyme Q reductase) | 30 | gi: 13543602 |
| COX6B | cytochrome c oxidase subunit VIb | 31 | gi: 6680989 |
| SDHA | succinate dehydrogenase complex, subunit A, flavoprotein (Fp) | 32 | gi: 4759079 |
| NDUFA8 | NADH dehydrogenase (ubiquinone) 1 alpha subcomplex, 8, 19 kDa | 33 | gi: 7657368 |
| COX6A2 | cytochrome c oxidase subunit VIa polypeptide 2 | 34 | gi: 4885148 |
| NDUFAF1 | NADH dehydrogenase (ubiquinone) 1 alpha subcomplex, assembly factor 1 | 35 | gi: 7705778 |
| ATP5O | ATP synthase, H+ transporting, mitochondrial F1 complex, O subunit (oligomycin sensitivity conferring protein) | 36 | gi: 21752725 |
| SDHB | succinate dehydrogenase complex, subunit B, iron sulfur (Ip) /// succinate dehydrogenase complex, subunit B, iron sulfur (Ip) | 37 | gi: 9257241 |
| NDUFB8 | NADH dehydrogenase (ubiquinone) 1 beta subcomplex, 8, 19 kDa | 38 | gi: 4826853 |
| COX4I1 | cytochrome c oxidase subunit IV isoform 1 /// cytochrome c oxidase subunit IV isoform 1 | 39 | gi: 2942504 |
| NDUFA2 | NADH dehydrogenase (ubiquinone) 1 alpha subcomplex, 2, 8 kDa | 40 | gi: 11446623 |
| COX6BP-3 | cytochrome c oxidase subunit VIb pseudogene-3 | 41 | gi: 5050980 |
| COX7A1 | cytochrome c oxidase subunit VIIa polypeptide 1 (muscle) | 42 | gi: 4502986 |
| NDUFB3 | NADH dehydrogenase (ubiquinone) 1 beta subcomplex, 3, 12 kDa | 43 | gi: 4505360 |
| NDUFS6 | NADH dehydrogenase (ubiquinone) Fe—S protein 6, 13 kDa (NADH-coenzyme Q reductase) | 44 | gi: 4758791 |
| SDHD | succinate dehydrogenase complex, subunit D, integral membrane protein | 45 | gi: 4506864 |
| COX7C | cytochrome c oxidase subunit VIIc | 46 | gi: 4502992 |

TABLE 1-continued

| Gene Name | | Ranks | GenBank Accession |
|---|---|---|---|
| NDUFA4 | NADH dehydrogenase (ubiquinone) 1 alpha subcomplex, 4, 9 kDa | 47 | gi: 4505356 |
| NDUFA10 | NADH dehydrogenase (ubiquinone) 1 alpha subcomplex, 10, 42 kDa | 48 | gi: 21411520 |
| NDUFB4 | NADH dehydrogenase (ubiquinone) 1 beta subcomplex, 4, 15 kDa | 49 | gi: 6041668 |
| UQCR | ubiquinol-cytochrome c reductase (6.4 kD) subunit | 50 | gi: 5803216 |
| NDUFC2 | NADH dehydrogenase (ubiquinone) 1, subcomplex unknown, 2, 14.5 kDa | 51 | gi: 11641234 |
| UCP1 | uncoupling protein 1 (mitochondrial, proton carrier) | 52 | gi: 13259539 |
| NDUFC1 | NADH dehydrogenase (ubiquinone) 1, subcomplex unknown, 1, 6 kDa | 53 | gi: 4505366 |
| COX8C | cytochrome c oxidase subunit 8C | 54 | gi: 6656776 |
| NDUFB1 | NADH dehydrogenase (ubiquinone) 1 beta subcomplex, 1, 7 kDa | 55 | gi: 4758775 |
| UQCRB | ubiquinol-cytochrome c reductase binding protein | 56 | gi: 5454151 |
| NDUFS3 | NADH dehydrogenase (ubiquinone) Fe—S protein 3, 30 kDa (NADH-coenzyme Q reductase) | 57 | gi: 4758787 |
| ATP5D | ATP synthase, H+ transporting, mitochondrial F1 complex, delta subunit | 58 | gi: 4502296 |
| COX7A2 | cytochrome c oxidase subunit VIIa polypeptide 2 (liver) | 59 | gi: 4502988 |
| NDUFB7 | NADH dehydrogenase (ubiquinone) 1 beta subcomplex, 7, 18 kDa | 60 | gi: 10764846 |
| NDUFB2 | NADH dehydrogenase (ubiquinone) 1 beta subcomplex, 2, 8 kDa | 61 | gi: 4758777 |
| NDUFA1 | NADH dehydrogenase (ubiquinone) 1 alpha subcomplex, 1, 7.5 kDa | 62 | gi: 13699820 |
| ATP5J2 | ATP synthase, H+ transporting, mitochondrial F0 complex, subunit f, isoform 2 | 63 | gi: 14384723 |
| COX7A2L | cytochrome c oxidase subunit VIIa polypeptide 2 like | 64 | gi: 4758041 |
| COX7B2 | cytochrome c oxidase subunit VIIb2 | 65 | gi: 3594967 |
| NDUFV3 | NADH dehydrogenase (ubiquinone) flavoprotein 3, 10 kDa | 66 | gi: 3597860 |
| NDUFA11 | NADH dehydrogenase (ubiquinone) 1 alpha subcomplex, 11, 14.7 kDa | 67 | gi: 10155912 |
| NDUFA3 | NADH dehydrogenase (ubiquinone) 1 alpha subcomplex, 3, 9 kDa | 68 | gi: 4758771 |
| UCP2 | uncoupling protein 2 (mitochondrial, proton carrier) | 69 | gi: 1877473 |
| COX15 | COX15 homolog, cytochrome c oxidase assembly protein (yeast) | 70 | gi: 4758035 |
| MTND4 | NADH dehydrogenase 4 | 71 | gi: 12005804 |
| MTCO1 | cytochrome c oxidase I | 72 | gi: 27754203 |
| MTND2 | NADH dehydrogenase 2 | 73 | gi: 27754201 |
| MTCO2 | cytochrome c oxidase II | 74 | gi: 27754205 |
| NDUFB9 | NADH dehydrogenase (ubiquinone) 1 beta subcomplex, 9, 22 kDa | 75 | gi: 9802311 |
| NDUFB10 | NADH dehydrogenase (ubiquinone) 1 beta subcomplex, 10, 22 kDa | 76 | gi: 4164441 |
| NDUFA2 | NADH dehydrogenase (ubiquinone) 1 alpha subcomplex, 2, 8 kDa | 77 | gi: 11446623 |
| ATP5I | ATP synthase, H+ transporting, mitochondrial F0 complex, subunit e | 78 | gi: 6005716 |
| MTND6 | NADH dehydrogenase 6 | 79 | gi: 27754187 |
| ATP5G2 | ATP synthase, H+ transporting, mitochondrial F0 complex, subunit c (subunit 9), isoform 2 | 80 | gi: 6671590 |
| COX17 | COX17 homolog, cytochrome c oxidase assembly protein (yeast) | 81 | gi: 13527356 |
| ATP5S | ATP synthase, H+ transporting, mitochondrial F0 complex, subunit s (factor B) | 82 | gi: 15341678 |
| NDUFB3P5 | NADH dehydrogenase (ubiquinone) 1 beta subcomplex, 3, 12 kDa pseudogene 5 | 83 | gi: 5262922 |
| COX10 | COX10 homolog, cytochrome c oxidase assembly protein, heme A: farnesyltransferase (yeast) | 84 | gi: 4502978 |
| NDUFS8 | NADH dehydrogenase (ubiquinone) Fe—S protein 8, 23 kDa (NADH-coenzyme Q reductase) | 85 | gi: 4505370 |
| MTND3 | NADH dehydrogenase 3 | 86 | gi: 27754195 |
| ATP5E | ATP synthase, H+ transporting, mitochondrial F1 complex, epsilon subunit | 87 | gi: 5901895 |
| ATP5L | ATP synthase, H+ transporting, mitochondrial F0 complex, subunit g | 88 | gi: 5453560 |
| NDUFA7 | NADH dehydrogenase (ubiquinone) 1 alpha subcomplex, 7, 14.5 kDa | 89 | gi: 4826849 |
| ATP5B | ATP synthase, H+ transporting, mitochondrial F1 complex, beta polypeptide | 90 | gi: 4502294 |
| COX6A1 | cytochrome c oxidase subunit VIa polypeptide 1 | 91 | gi: 10047079 |
| COX4I2 | cytochrome c oxidase subunit IV isoform 2 | 92 | gi: 11493211 |

TABLE 1-continued

| Gene Name | | Ranks | GenBank Accession |
|---|---|---|---|
| SDHC | succinate dehydrogenase complex, subunit C, integral membrane protein, 15 kDa | 93 | gi: 9257243 |
| ATP5F1 | ATP synthase, H+ transporting, mitochondrial F0 complex, subunit b, isoform 1 | 94 | gi: 13543617 |
| NDUFS5 | NADH dehydrogenase (ubiquinone) Fe—S protein 5, 15 kDa (NADH-coenzyme Q reductase) | 95 | gi: 4758789 |

Signature for Human Muscle Age. In another embodiment, the expression pattern of genes in at least one identified functional group is used to generate a signature for muscle aging. In addition to the functional groups of the human common signature for aging, functional groups of the human signature for muscle aging include mRNA splicing and processing pathway, which increases expression with age; and calcium ion transport pathway, which decreases with age in human muscle. Genes associated with aging in muscle tissues include those set forth in Table 2.

| Gene Symbol | Name | Genbank ID | Slope of Expression with age (log2) |
|---|---|---|---|
| Spliceosome-Increasing Expression with Age | | | |
| ADAR | adenosine deaminase, RNA-specific | gi: 7669471 | 0.004314 |
| ADARB1 | adenosine deaminase, RNA-specific, B1 (RED1 homolog rat) | gi: 7669476 | 0.000807 |
| ADARB2 | adenosine deaminase, RNA-specific, B2 (RED2 homolog rat) | gi: 8922076 | 0.001861 |
| ADARB2 | adenosine deaminase, RNA-specific, B2 (RED2 homolog rat) | gi: 5447667 | 3.92E−05 |
| ADAT1 | adenosine deaminase, tRNA-specific 1 | gi: 7382475 | 0.003445 |
| CPSF1 | cleavage and polyadenylation specific factor 1, 160 kDa | gi: 10037183 | 0.001859 |
| CPSF2 | cleavage and polyadenylation specific factor 2, 100 kDa | gi: 7243114 | 0.003399 |
| CPSF3 | cleavage and polyadenylation specific factor 3, 73 kDa | gi: 7706426 | −0.00018 |
| CPSF4 | cleavage and polyadenylation specific factor 4, 30 kDa | gi: 5729938 | 0.003095 |
| CPSF5 | cleavage and polyadenylation specific factor 5, 25 kDa | gi: 5901925 | 0.001425 |
| CPSF6 | cleavage and polyadenylation specific factor 6, 68 kDa | gi: 11010888 | 0.001368 |
| HNRPA0 | heterogeneous nuclear ribonucleoprotein A0 | gi: 11772191 | 0.001445 |
| HNRPA1 | heterogeneous nuclear ribonucleoprotein A1 | gi: 4504444 | 0.003225 |
| HNRPA2B1 | heterogeneous nuclear ribonucleoprotein A2/B1 | gi: 4504446 | 3.12E−05 |
| HNRPA3 | heterogeneous nuclear ribonucleoprotein A3 | gi: 5031692 | 0.001038 |
| HNRPAB | heterogeneous nuclear ribonucleoprotein A/B | gi: 4758541 | 0.002551 |
| HNRPC | heterogeneous nuclear ribonucleoprotein C (C1/C2) | gi: 4758543 | 0.002504 |
| HNRPD | heterogeneous nuclear ribonucleoprotein D (AU-rich element RNA binding protein 1, 37 kDa) | gi: 181913 | 0.002637 |
| HNRPDL | heterogeneous nuclear ribonucleoprotein D-like | gi: 15010817 | −0.00079 |
| HNRPF | heterogeneous nuclear ribonucleoprotein F | gi: 4600402 | 0.001024 |
| HNRPH1 | heterogeneous nuclear ribonucleoprotein H1 (H) /// heterogeneous nuclear ribonucleoprotein H1 (H) | gi: 5031752 | 0.003195 |
| HNRPH2 | heterogeneous nuclear ribonucleoprotein H2 (H') | gi: 9624997 | 0.003309 |
| HNRPH3 | heterogeneous nuclear ribonucleoprotein H3 (2H9) | gi: 11056058 | 0.000146 |
| HNRPK | heterogeneous nuclear ribonucleoprotein K | gi: 4989849 | −0.00047 |
| HNRPL | heterogeneous nuclear ribonucleoprotein L | gi: 4557644 | 0.002437 |
| HNRPM | heterogeneous nuclear ribonucleoprotein M | gi: 19584534 | 0.002966 |
| HNRPR | heterogeneous nuclear ribonucleoprotein R | gi: 5031754 | 0.000268 |
| HNRPU | heterogeneous nuclear ribonucleoprotein U (scaffold attachment factor A) | gi: 13177672 | 0.001293 |
| HNRPUL1 | heterogeneous nuclear ribonucleoprotein U-like 1 | gi: 12040125 | |
| RBM10 | RNA binding motif protein 10 | gi: 13278827 | |
| RBM11 | RNA binding motif protein 11 | gi: 1267105 | |
| RBM12 | RNA binding motif protein 12 | gi: 12778041 | |
| RBM14 | RNA binding motif protein 14 | gi: 15022508 | |
| RBM15 | RNA binding motif protein 15 | gi: 14210074 | |
| RBM16 | RNA binding motif protein 16 | gi: 7662491 | |
| RBM17 | RNA binding motif protein 17 | gi: 5454081 | |
| RBM18 | RNA binding motif protein 18 | gi: 4901298 | |
| RBM19 | RNA binding motif protein 19 | gi: 7705364 | |
| RBM20 | RNA binding motif protein 20 | gi: 4453253 | |
| RBM21 | RNA binding motif protein 21 | gi: 12383073 | |
| RBM22 | RNA binding motif protein 22 | gi: 8922327 | |
| RBM23 | RNA binding motif protein 23 | gi: 8922449 | |
| RBM24 | RNA binding motif protein 24 | gi: 4887883 | |
| RBM25 | RNA binding motif protein 25 | gi: 2358348 | |
| RBM27 | RNA binding motif protein 27 | gi: 7242976 | |
| RBM3 | RNA binding motif (RNP1, RRM) protein 3 | gi: 5803136 | |
| RBM4 | RNA binding motif protein 4 | gi: 4506444 | |
| RBM5 | RNA binding motif protein 5 | gi: 1244403 | |
| RBM6 | RNA binding motif protein 6 | gi: 3741698 | |

-continued

| Gene Symbol | Name | Genbank ID | Slope of Expression with age (log2) |
|---|---|---|---|
| RBM7 | RNA binding motif protein 7 | gi: 9994184 | |
| RBM8A | RNA binding motif protein 8A | gi: 17389452 | |
| RBM9 | RNA binding motif protein 9 | gi: 1267308 | |
| RBMS1 | RNA binding motif, single stranded interacting protein 1 | gi: 8400723 | |
| RBMS2 | RNA binding motif, single stranded interacting protein 2 | gi: 4506448 | |
| RBMS3 | RNA binding motif, single stranded interacting protein | gi: 21732350 | |
| RBMS3 | RNA binding motif, single stranded interacting protein | gi: 7657505 | |
| RBMX | RNA binding motif protein, X-linked | gi: 2186080 | |
| SF1 | splicing factor 1 | gi: 473832 | |
| SF3A1 | splicing factor 3a, subunit 1, 120 kDa | gi: 10968379 | |
| SF3A2 | splicing factor 3a, subunit 2, 66 kDa | gi: 13325229 | |
| SF3A3 | splicing factor 3a, subunit 3, 60 kDa | gi: 5803166 | |
| SF3B1 | splicing factor 3b, subunit 1, 155 kDa | gi: 5101370 | |
| SF3B2 | splicing factor 3b, subunit 2, 145 kDa | gi: 12186182 | |
| SF3B3 | splicing factor 3b, subunit 3, 130 kDa /// splicing factor 3b, subunit 3, 130 kDa | gi: 11034822 | |
| SF3B4 | splicing factor 3b, subunit 4, 49 kDa /// splicing factor 3b, subunit 4, 49k Da | gi: 13279088 | |
| SF3B5 | splicing factor 3b, subunit 5, 10 kDa /// splicing factor 3b, subunit 5, 10 kDa | gi: 13775199 | |
| SF4 | splicing factor 4 | gi: 12654434 | |
| SFRS1 | splicing factor, arginine/serine-rich 1 (splicing factor 2, alternate splicing factor) | gi: 338046 | |
| SFRS10 | splicing factor, arginine/serine-rich 10 (transformer 2 homolog, *Drosophila*) | gi: 12653362 | |
| SFRS11 | splicing factor, arginine/serine-rich 11 | gi: 11007758 | |
| SFRS11 | splicing factor, arginine/serine-rich 11 /// splicing factor, arginine/serine-rich 11 | gi: 4759099 | |
| SFRS12 | splicing factor, arginine/serine-rich 12 | gi: 23270825 | |
| SFRS14 | splicing factor, arginine/serine-rich 14 | gi: 2224670 | |
| SFRS15 | splicing factor, arginine/serine-rich 15 | gi: 2574950 | |
| SFRS16 | splicing factor, arginine/serine-rich 16 (suppressor-of-white-apricot homolog, *Drosophila*) | gi: 5902129 | |
| SFRS2 | splicing factor, arginine/serine-rich 2 | gi: 10315361 | |
| SFRS2IP | splicing factor, arginine/serine-rich 2, interacting protein | gi: 18088437 | |
| SFRS3 | splicing factor, arginine/serine-rich 3 | gi: 4506900 | |
| SFRS4 | splicing factor, arginine/serine-rich 4 /// splicing factor, arginine/serine-rich 4 | gi: 5032088 | |
| SFRS5 | splicing factor, arginine/serine-rich 5 | gi: 5902077 | |
| SFRS6 | splicing factor, arginine/serine-rich 6 | gi: 11225261 | |
| SFRS7 | splicing factor, arginine/serine-rich 7, 35 kDa /// splicing factor, arginine/serine-rich 7, 35 kDa | gi: 6857827 | |
| SFRS8 | splicing factor, arginine/serine-rich 8 (suppressor-of-white-apricot homolog, *Drosophila*) | gi: 3238908 | |
| SFRS9 | splicing factor, arginine/serine-rich 9 /// splicing factor, arginine/serine-rich 9 /// splicing factor, arginine/serine-rich 9 | gi: 4506902 | |
| SNRP70 | small nuclear ribonucleoprotein 70 kDa polypeptide (RNP antigen) | gi: 11008109 | |
| SNRPA | small nuclear ribonucleoprotein polypeptide A | gi: 4759155 | |
| SNRPA1 | small nuclear ribonucleoprotein polypeptide A' | gi: 4507120 | |
| SNRPB | small nuclear ribonucleoprotein polypeptides B and B1 | gi: 190246 | |
| SNRPB2 | small nuclear ribonucleoprotein polypeptide B" | gi: 9512700 | |
| SNRPB2 | small nuclear ribonucleoprotein polypeptide B" | gi: 4507122 | |
| SNRPC | small nuclear ribonucleoprotein polypeptide C | gi: 4507126 | |
| SNRPD1 | small nuclear ribonucleoprotein D1 polypeptide 16 kDa | gi: 12804598 | |
| SNRPD2 | small nuclear ribonucleoprotein D2 polypeptide 16.5 kDa | gi: 7242206 | |
| SNRPD3 | small nuclear ribonucleoprotein D3 polypeptide 18 kDa | gi: 4759159 | |
| SNRPD3 | small nuclear ribonucleoprotein D3 polypeptide 18 kDa | gi: 11594462 | |
| SNRPE | small nuclear ribonucleoprotein polypeptide E | gi: 4507128 | |
| SNRPF | small nuclear ribonucleoprotein polypeptide F | gi: 4507130 | |
| SNRPG | small nuclear ribonucleoprotein polypeptide G | gi: 4507132 | |
| SNRPN | small nuclear ribonucleoprotein polypeptide N | gi: 21732797 | |
| Calcium/Chloride Ion Transport | | | |
| ATP2A1 | ATPase, Ca++ transporting, cardiac muscle, fast twitch 1 | gi: 10835219 | −0.00639 |
| ATP2A2 | ATPase, Ca++ transporting, cardiac muscle, slow twitch 2 | gi: 184100 | −0.00022 |
| ATP2A3 | ATPase, Ca++ transporting, ubiquitous | gi: 3211976 | −0.00069 |
| ATP2B1 | ATPase, Ca++ transporting, plasma membrane 1 | gi: 184269 | −0.0006 |
| ATP2B2 | ATPase, Ca++ transporting, plasma membrane 2 | gi: 814549 | −0.00247 |
| ATP2B3 | ATPase, Ca++ transporting, plasma membrane 3 | gi: 11386154 | −0.00372 |
| ATP2B4 | ATPase, Ca++ transporting, plasma membrane 4 | gi: 4502288 | −0.004 |
| ATP2C1 | ATPase, Ca++ transporting, type 2C, member 1 | gi: 7021496 | −0.00038 |
| CACNA1A | calcium channel, voltage-dependent, P/Q type, alpha 1A subunit | gi: 13386497 | −0.00219 |
| CACNA1B | calcium channel, voltage-dependent, L type, alpha 1B subunit | gi: 4502522 | 0.000632 |

-continued

| Gene Symbol | Name | Genbank ID | Slope of Expression with age (log2) |
|---|---|---|---|
| CACNA1C | calcium channel, voltage-dependent, L type, alpha 1C subunit | gi: 4502524 | −0.00323 |
| CACNA1D | calcium channel, voltage-dependent, L type, alpha 1D subunit | gi: 1162804 | −0.00359 |
| CACNA1E | calcium channel, voltage-dependent, alpha 1E subunit | gi: 4502528 | −0.00112 |
| CACNA1F | calcium channel, voltage-dependent, alpha 1F subunit | gi: 4885102 | −0.00065 |
| CACNA1G | calcium channel, voltage-dependent, alpha 1G subunit | gi: 9256522 | 0.001804 |
| CACNA1H | calcium channel, voltage-dependent, alpha 1H subunit | gi: 10864076 | |
| CACNA1I | calcium channel, voltage-dependent, alpha 1I subunit | gi: 10863882 | |
| CACNA1S | calcium channel, voltage-dependent, L type, alpha 1S subunit | gi: 4217513 | |
| CACNA2D1 | calcium channel, voltage-dependent, alpha 2/delta subunit 1 | gi: 4757893 | |
| CACNA2D2 | calcium channel, voltage-dependent, alpha 2/delta subunit 2 | gi: 5174402 | |
| CACNA2D3 | calcium channel, voltage-dependent, alpha 2/delta 3 subunit | gi: 8923764 | |
| CACNA2D4 | calcium channel, voltage-dependent, alpha 2/delta subunit 4 | gi: 27312024 | |
| CACNB1 | calcium channel, voltage-dependent, beta 1 subunit | gi: 4502530 | |
| CACNB2 | calcium channel, voltage-dependent, beta 2 subunit | gi: 18481640 | |
| CACNB3 | calcium channel, voltage-dependent, beta 3 subunit | gi: 463890 | |
| CACNB4 | calcium channel, voltage-dependent, beta 4 subunit | gi: 4502536 | |
| CACNG1 | calcium channel, voltage-dependent, gamma subunit 1 | gi: 4502538 | |
| CACNG2 | calcium channel, voltage-dependent, gamma subunit 2 | gi: 5174404 | |
| CACNG3 | calcium channel, voltage-dependent, gamma subunit 3 | gi: 5729755 | |
| CACNG4 | calcium channel, voltage-dependent, gamma subunit 4 | gi: 13325399 | |
| CACNG5 | calcium channel, voltage-dependent, gamma subunit 5 | gi: 22027550 | |
| CACNG6 | calcium channel, voltage-dependent, gamma subunit 6 | gi: 22027556 | |
| CACNG7 | calcium channel, voltage-dependent, gamma subunit 7 | gi: 13357177 | |
| CACNG8 | calcium channel, voltage-dependent, gamma subunit 8 | gi: 13357179 | |
| CLCA1 | chloride channel, calcium activated, family member 1 | gi: 4585468 | |
| CLCA2 | chloride channel, calcium activated, family member 2 | gi: 12025665 | |
| CLCA3 | chloride channel, calcium activated, family member 3 | gi: 4757997 | |
| CLCA4 | chloride channel, calcium activated, family member 4 | gi: 12025666 | |
| CLCN1 | chloride channel 1, skeletal muscle (Thomsen disease, autosomal dominant) | gi: 4502866 | |
| CLCN2 | chloride channel 2 | gi: 5803001 | |
| CLCN3 | chloride channel 3 | gi: 2599547 | |
| CLCN4 | chloride channel 4 | gi: 1578556 | |
| CLCN5 | chloride channel 5 (nephrolithiasis 2, X-linked, Dent disease) | gi: 4557472 | |
| CLCN6 | chloride channel 6 | gi: 4502872 | |
| CLCN7 | chloride channel 7 | gi: 4826481 | |
| CLCNKA | chloride channel Ka | gi: 18088620 | |
| CLCNKB | chloride channel Kb | gi: 18088620 | |

Signature for Human Muscle Age. In another embodiment, the expression pattern of genes in at least one identified functional group is used to generate a signature for kidney aging. In addition to the functional groups of the human common signature for aging, functional groups of the human signature for kidney aging include maintenance of epithelial polarity, which generally increase expression with aging; ribosomal proteins, which increase expression with aging; and specific transcription factors and signaling pathway components. Genes associated with aging in kidney include those set forth in Table 3.

Age-Related Genes ($p<0.001$) in Kidney, Arranged by Fold-Change

| Probe ID | Fold change | Description |
|---|---|---|
| 206254_AT | −2.65274472 | epidermal growth factor (beta-urogastrone) |
| 206054_AT | −1.90454932 | kininogen |
| 214598_AT | −1.68966091 | claudin 8 |
| 203549_S_AT | −1.68320046 | lipoprotein lipase |
| 203548_S_AT | −1.63017116 | lipoprotein lipase |
| 243562_AT | −1.61656252 | CLONE = IMAGE: 3133612 /UG = Hs.117112 ESTs |
| 217512_AT | −1.60274444 | ESTs, Highly similar to 1312232A kininogen L, high MW |
| 207057_AT | −1.55817498 | solute carrier family 16 (monocarboxylic acid transporters), member 7 |
| 218772_X_AT | −1.49982695 | hypothetical protein FLJ10493 |
| 221590_S_AT | −1.48573473 | aldehyde dehydrogenase 6 family, member A1 |
| 241925_X_AT | −1.46775818 | Consensus includes gb: BF207870 /FEA = EST /DB_XREF = gi: 11101456 /DB_XREF = est: 601862578F1 /CLONE = IMAGE: 4082082 /UG = Hs.219226 ESTs |
| 207781_S_AT | −1.46652361 | zinc finger protein 6 (CMPX1) |
| 215108_X_AT | −1.462704 | trinucleotide repeat containing 9 |
| 214774_X_AT | −1.45121774 | trinucleotide repeat containing 9 |
| 205413_AT | −1.45104363 | chromosome 11 open reading frame 8 |
| 205773_AT | −1.45080256 | KIAA0940 protein |
| 205278_AT | −1.42942993 | glutamate decarboxylase 1 (brain, 67 kDa) |
| 216623_X_AT | −1.42308206 | trinucleotide repeat containing 9 |

| Probe ID | Fold change | Description |
| --- | --- | --- |
| 219732_AT | −1.42081927 | hypothetical protein FLJ20300 |
| 209340_AT | −1.41960652 | UDP-N-acteylglucosamine pyrophosphorylase 1 |
| 211689_S_AT | −1.41384655 | transmembrane protease, serine 2 |
| 209966_X_AT | −1.40803139 | estrogen-related receptor gamma |
| 203543_S_AT | −1.40692542 | basic transcription element binding protein 1 |
| 208869_S_AT | −1.39958281 | GABA(A) receptor-associated protein like 1 |
| 203542_S_AT | −1.37296862 | basic transcription element binding protein 1 |
| 214829_AT | −1.37211153 | aminoadipate-semialdehyde synthase |
| 203962_S_AT | −1.37105125 | nebulette |
| 220728_AT | −1.36752675 | Homo sapiens cDNA FLJ13480 fis, clone PLACE1003768 |
| 205498_AT | −1.36727065 | growth hormone receptor |
| 224237_AT | −1.36258559 | hypothetical protein PRO2372 |
| 205343_AT | −1.36211003 | sulfotransferase family, cytosolic, 1C, member 1 |
| 202780_AT | −1.36164729 | 3-oxoacid CoA transferase |
| 211600_AT | −1.35789069 | Human glomerular epithelial protein 1 (GLEPP1) mRNA, |
| 209243_S_AT | −1.35766223 | zinc finger, imprinted 2 |
| 242775_AT | −1.35564502 | CLONE = IMAGE: 3707280 /UG = Hs.114959 ESTs, |
| 218350_S_AT | −1.35561551 | geminin, DNA replication inhibitor |
| 217680_X_AT | −1.35548101 | CLONE = IMAGE: 4262274 /UG = Hs.322737 ESTs |
| 221221_S_AT | −1.35418041 | kelch-like 3 (Drosophila) |
| 203961_AT | −1.3478557 | nebulette |
| 208848_AT | −1.34606297 | alcohol dehydrogenase 5 (class III), chi polypeptide |
| 214920_AT | −1.34325648 | Homo sapiens cDNA FLJ11022 fis, clone PLACE1003771 |
| 211992_AT | −1.33095298 | protein kinase, lysine deficient 1 |
| 212229_S_AT | −1.32436547 | F-box only protein 21 |
| 208868_S_AT | −1.32436432 | GABA(A) receptor-associated protein like 1 |
| 205371_S_AT | −1.32425385 | dihydrolipoamide branched chain transacylase (E2 component of branched chain keto acid dehydrogenase complex; maple syrup urine disease) |
| 202242_AT | −1.32169226 | transmembrane 4 superfamily member 2 |
| 218024_AT | −1.32092619 | brain protein 44-like |
| 218025_S_AT | −1.32021953 | peroxisomal D3, D2-enoyl-CoA isomerase |
| 216022_AT | −1.31305478 | Homo sapiens mRNA; cDNA DKFZp564I153 (from clone DKFZp564I153) |
| 210833_AT | −1.31157081 | prostaglandin E receptor 3 (subtype EP3) |
| 218170_AT | −1.31118109 | CGI-111 protein |
| 203335_AT | −1.30822483 | phytanoyl-CoA hydroxylase (Refsum disease) |
| 217127_AT | −1.30809956 | DB_XREF = gi: 9717070 /UG = Hs.19904 cystathionase (cystathionine gamma-lyase) |
| 219949_AT | −1.30804865 | leucine-rich repeat-containing 2 |
| 213245_AT | −1.30679315 | Homo sapiens cDNA FLJ30781 fis, clone FEBRA2000874 |
| 212308_AT | −1.30493234 | cytoplasmic linker associated protein 2 |
| 235061_AT | −1.30292614 | CLONE = ADBDAF07 /UG = Hs.291000 ESTs |
| 202975_S_AT | −1.29383819 | Rho-related BTB domain containing 3 |
| 202976_S_AT | −1.29299796 | Rho-related BTB domain containing 3 |
| 221986_S_AT | −1.29295512 | hypothetical protein FLJ20059 |
| 210825_S_AT | −1.29199425 | erythrocyte membrane protein band 7.2 (stomatin) |
| 201689_S_AT | −1.28908447 | tumor protein D52 |
| 212599_AT | −1.28726395 | autism-related protein 1 |
| 212771_AT | −1.28331857 | Homo sapiens mRNA; cDNA DKFZp564A026 (from clone DKFZp564A026) |
| 203710_AT | −1.27572896 | inositol 1,4,5-triphosphate receptor, type 1 |
| 203774_AT | −1.27412008 | 5-methyltetrahydrofolate-homocysteine methyltransferase |
| 208905_AT | −1.27257254 | cytochrome c |
| 218793_S_AT | −1.27170765 | sex comb on midleg-like 1 (Drosophila) |
| 213308_AT | −1.27061856 | SH3 and multiple ankyrin repeat domains 2 |
| 228988_AT | −1.26996849 | zinc finger protein 6 (CMPX1) |
| 216173_AT | −1.26579651 | Homo sapiens cDNA: FLJ21707 fis, clone COL09953 |
| 226553_AT | −1.26159863 | transmembrane protease, serine 2 |
| 212231_AT | −1.2603298 | F-box only protein 21 |
| 211458_S_AT | −1.25719466 | GABA(A) receptors associated protein like 3 |
| 205353_S_AT | −1.2563457 | prostatic binding protein |
| 212956_AT | −1.25228059 | KIAA0882 protein |
| 201688_S_AT | −1.25013617 | tumor protein D52 |
| 217901_AT | −1.24760125 | Homo sapiens, clone IMAGE: 4242700, mRNA |
| 204143_S_AT | −1.24695197 | rTS beta protein |
| 217506_AT | −1.2463855 | ESTs, Weakly similar to hypothetical protein FLJ20378 [Homo sapiens] [H. sapiens] |
| 213353_AT | −1.24604628 | ATP-binding cassette, sub-family A (ABC1), member 5 |
| 205350_AT | −1.2421432 | cellular retinoic acid binding protein 1 |
| 228855_AT | −1.24176524 | nudix (nucleoside diphosphate linked moiety X)-type motif 7 |
| 206874_S_AT | −1.24091935 | Ste20-related serine/threonine kinase |
| 91920_AT | −1.23998086 | chondroitin sulfate proteoglycan BEHAB/brevican |
| 201007_AT | −1.23877842 | hydroxyacyl-Coenzyme A dehydrogenase/3-ketoacyl-Coenzyme A thiolase/enoyl-Coenzyme A hydratase (trifunctional protein), beta subunit |
| 212445_S_AT | −1.23634356 | neural precursor cell expressed, developmentally down-regulated 4-like |

-continued

| Probe ID | Fold change | Description |
|---|---|---|
| 218432_AT | −1.23606015 | F-box only protein 3 |
| 219429_AT | −1.2351116 | fatty acid hydroxylase |
| 200848_AT | −1.23449792 | S-adenosylhomocysteine hydrolase-like 1 |
| 201917_S_AT | −1.23443477 | hypothetical protein FLJ10618 |
| 210650_S_AT | −1.23299133 | piccolo (presynaptic cytomatrix protein) |
| 217988_AT | −1.23092887 | enhancer of invasion 10 |
| 238692_AT | −1.22894129 | Consensus includes gb: AL040935 /FEA = EST /DB_XREF = gi: 5409879 /DB_XREF = est: DKFZp434K1715_r1 /CLONE = DKFZp434K1715 /UG = Hs.271272 ESTs, Weakly similar to hypothetical protein *H. sapiens* |
| 215578_AT | −1.22802527 | *Homo sapiens* cDNA FLJ11662 fis, clone HEMBA1004629 |
| 212181_S_AT | −1.2241576 | nudix (nucleoside diphosphate linked moiety X)-type motif 4 |
| 212448_AT | −1.2229944 | neural precursor cell expressed, developmentally down-regulated 4-like |
| 203627_AT | −1.22231337 | insulin-like growth factor 1 receptor |
| 228716_AT | −1.2203084 | CLONE = IMAGE: 4673182 /UG = Hs.203213 ESTs |
| 211303_X_AT | −1.22024729 | folate hydrolase (prostate-specific membrane antigen) 1 |
| 230008_AT | −1.21997535 | CLONE = IMAGE: 2365454 /UG = Hs.23799 ESTs |
| 201690_S_AT | −1.21753378 | tumor protein D52 |
| 201619_AT | −1.2170889 | peroxiredoxin 3 |
| 216189_AT | −1.2166982 | *Homo sapiens*, clone IMAGE: 3344506, mRNA, partial cds |
| 209366_X_AT | −1.21651132 | cytochrome b-5 |
| 228051_AT | −1.21447265 | Consensus includes gb: AI979261 /FEA = EST /DB_XREF = gi: 5804280 /DB_XREF = est: wr72g05.x1 /CLONE = IMAGE: 2493272 /UG = Hs.102720 ESTs |
| 205776_AT | −1.21395425 | flavin containing monooxygenase 5 |
| 204793_AT | −1.2121485 | KIAA0443 gene product |
| 201599_AT | −1.20871256 | ornithine aminotransferase (gyrate atrophy) |
| 230645_AT | −1.20841509 | CLONE = IMAGE: 3567071 /UG = Hs.150478 |
| 209916_AT | −1.20554061 | KIAA1630 protein |
| 238530_AT | −1.20520574 | CLONE = IMAGE: 4247399 /UG = Hs.95793 ESTs |
| 202886_S_AT | −1.20383161 | protein phosphatase 2 (formerly 2A), regulatory subunit A (PR 65), beta isoform |
| 203859_S_AT | −1.20302619 | paralemmin |
| 240519_AT | −1.20229081 | CLONE = IMAGE: 1565190 /UG = Hs.132894 ESTs |
| 236170_X_AT | −1.20006966 | CLONE = IMAGE: 2066601 /UG = Hs.134071 ESTs |
| 203039_S_AT | −1.1990056 | NADH dehydrogenase (ubiquinone) Fe—S protein 1, 75 kDa (NADH-coenzyme Q reductase) |
| 221543_S_AT | −1.1988313 | chromosome 8 open reading frame 2 |
| 210409_AT | −1.19793095 | myeloid/lymphoid or mixed-lineage leukemia (trithorax homolog, *Drosophila*); translocated to, 4 |
| 213263_S_AT | −1.19531686 | mitogen-activated protein kinase kinase kinase 12 |
| 211994_AT | −1.19436248 | Human clone A9A2BRBS (CAC)n/(GTG)n repeat-containing mRNA |
| 215300_S_AT | −1.19332239 | flavin containing monooxygenase 5 |
| 212568_S_AT | −1.19317921 | dihydrolipoamide S-acetyltransferase (E2 component of pyruvate dehydrogenase complex) |
| 202110_AT | −1.19263303 | cytochrome c oxidase subunit VIIb |
| 207507_S_AT | −1.19166899 | ATP synthase, H+ transporting, mitochondrial F0 complex, subunit c (subunit 9) isoform 3 |
| 214629_X_AT | −1.1916409 | reticulon 4 |
| 225173_AT | −1.19106253 | MacGAP protein |
| 220925_AT | −1.18940274 | FLJ21613 similar to rat corneal wound healing related protein |
| 65630_AT | −1.18755469 | *Homo sapiens*, Similar to RIKEN cDNA 5530601I19 gene, clone MGC: 9743 IMAGE: 3854028, mRNA, complete cds |
| 210968_S_AT | −1.18735616 | reticulon 4 |
| 213564_X_AT | −1.18584496 | lactate dehydrogenase B |
| 219204_S_AT | −1.1857116 | serine racemase |
| 218637_AT | −1.18459303 | hypothetical protein IMPACT |
| 200780_X_AT | −1.18222481 | GNAS complex locus |
| 201030_X_AT | −1.18118636 | lactate dehydrogenase B |
| 202960_S_AT | −1.17837608 | methylmalonyl Coenzyme A mutase |
| 211615_S_AT | −1.17707851 | leucine-rich PPR-motif containing |
| 211509_S_AT | −1.1726182 | reticulon 4 |
| 201978_S_AT | −1.17109564 | KIAA0141 gene product |
| 227019_AT | −1.17087982 | Consensus includes gb: AA129774 /FEA = EST /DB_XREF = gi: 1690185 /DB_XREF = est: zl16h09.s1 /CLONE = IMAGE: 502145 /UG = Hs.288905 *Homo sapiens* cDNA FLJ13137 fis, clone NT2RP3003150 |
| 230828_AT | −1.17048926 | Consensus includes gb: AI379514 /FEA = EST /DB_XREF = gi: 4189367 /DB_XREF = est: tc64c02.x1 /CLONE = IMAGE: 2069378 /UG = Hs.114727 *Homo sapiens* cDNA FLJ11154 fis, clone PLACE1006932 |
| 65472_AT | −1.16875602 | *Homo sapiens* cDNA FLJ35653 fis, clone SPLEN2013690 |
| 213738_S_AT | −1.16801257 | ATP synthase, H+ transporting, mitochondrial F1 complex, alpha subunit, isoform 1, cardiac muscle |
| 209274_S_AT | −1.16762463 | hypothetical protein MGC4276 similar to CG8198 |
| 221985_AT | −1.16720677 | hypothetical protein FLJ20059 |

-continued

| Probe ID | Fold change | Description |
|---|---|---|
| 227632_AT | −1.16654532 | Consensus includes gb: N74056 /FEA = EST /DB_XREF = gi: 1231341 /DB_XREF = est: za58d04.s1 /CLONE = IMAGE: 296743 /UG = Hs.26966 KIAA1171 protein |
| 219288_AT | −1.16642254 | HT021 |
| 212175_S_AT | −1.16577054 | adenylate kinase 2 |
| 204182_S_AT | −1.16306974 | zinc finger protein 297B |
| 201119_S_AT | −1.16132535 | cytochrome c oxidase subunit VIII |
| 201100_S_AT | −1.15666012 | ubiquitin specific protease 9, X chromosome (fat facets-like *Drosophila*) |
| 239764_AT | −1.15304866 | Consensus includes gb: AA702143 /FEA = EST /DB_XREF = gi: 2705256 /DB_XREF = est: zi85h05.s1 /CLONE = IMAGE: 447609 /UG = Hs.190365 ESTs |
| 212073_AT | −1.15240151 | casein kinase 2, alpha 1 polypeptide |
| 219036_AT | −1.1507518 | p10-binding protein |
| 223194_S_AT | −1.14875186 | hypothetical protein FLJ22174 |
| 204149_S_AT | −1.14554212 | glutathione S-transferase M1 |
| 204199_AT | −1.14536943 | Ral guanine nucleotide exchange factor RalGPS1A |
| 220129_AT | −1.14528817 | hypothetical protein FLJ20449 |
| 200708_AT | −1.14491425 | glutamic-oxaloacetic transaminase 2, mitochondrial (aspartate aminotransferase 2) |
| 207709_AT | −1.1441423 | protein kinase, AMP-activated, alpha 2 catalytic subunit |
| 212273_X_AT | −1.14376241 | GNAS complex locus |
| 217649_AT | −1.14280468 | ESTs, Highly similar to zinc finger protein 216 [*Homo sapiens*] [*H. sapiens*] |
| 201134_X_AT | −1.13995956 | cytochrome c oxidase subunit VIIc |
| 210653_S_AT | −1.13875797 | branched chain keto acid dehydrogenase E1, beta polypeptide (maple syrup urine disease) |
| 209064_X_AT | −1.13761142 | polyadenylate binding protein-interacting protein 1 |
| 229909_AT | −1.13743587 | Consensus includes gb: AI654238 /FEA = EST /DB_XREF = gi: 4738217 /DB_XREF = est: tq89a02.x1 /CLONE = IMAGE: 2215946 /UG = Hs.98969 ESTs |
| 210236_AT | −1.13541059 | protein tyrosine phosphatase, receptor type, f polypeptide (PTPRF), interacting protein (liprin), alpha 1 |
| 229248_AT | −1.13503627 | Consensus includes gb: AA020784 /FEA = EST /DB_XREF = gi: 1484592 /DB_XREF = est: ze64f01.s1 /CLONE = IMAGE: 363769 /UG = Hs.25223 ESTs |
| 204178_S_AT | −1.13453786 | RNA binding motif protein 14 |
| 201273_S_AT | −1.13313629 | signal recognition particle 9 kDa |
| 215316_AT | −1.13311815 | *Homo sapiens* mRNA; cDNA DKFZp434M091 (from clone DKFZp434M091) |
| 218716_X_AT | −1.13309761 | MTO1 protein |
| 219205_AT | −1.13174133 | serine racemase |
| 213307_AT | −1.13146994 | SH3 and multiple ankyrin repeat domains 2 |
| 204294_AT | −1.13106548 | aminomethyltransferase (glycine cleavage system protein T) |
| 221531_AT | −1.13101319 | recombination protein REC14 |
| 209590_AT | −1.13078457 | bone morphogenetic protein 7 (osteogenic protein 1) |
| 201754_AT | −1.13070596 | cytochrome c oxidase subunit VIc |
| 212114_AT | −1.1282971 | *Homo sapiens*, clone MGC: 17296 IMAGE: 3460701, mRNA, complete cds |
| 204367_AT | −1.12698112 | Sp2 transcription factor |
| 221823_AT | −1.12337679 | hypothetical gene supported by AF038182; BC009203 |
| 208248_X_AT | −1.12289062 | amyloid beta (A4) precursor-like protein 2 |
| 202967_AT | −1.12246892 | glutathione S-transferase A4 |
| 208704_X_AT | −1.12241679 | amyloid beta (A4) precursor-like protein 2 |
| 204300_AT | −1.12006476 | PET112-like (yeast) |
| 200690_AT | −1.11854492 | heat shock 70 kDa protein 9B (mortalin-2) |
| 242449_AT | −1.11213009 | Consensus includes gb: BG054682 /FEA = EST /DB_XREF = gi: 12511636 /DB_XREF = est: 7o46f11.x1 /CLONE = IMAGE: 3577125 /UG = Hs.144763 ESTs |
| 212121_AT | −1.10840533 | DKFZP564D116 protein |
| 232047_AT | −1.10807855 | Consensus includes gb: AA913635 /FEA = EST /DB_XREF = gi: 3053027 /DB_XREF = est: om94f01.s2 /CLONE = IMAGE: 1554841 /UG = Hs.326413 *Homo sapiens* cDNA FLJ20812 fis, clone ADSE01316 |
| 235269_AT | −1.1017098 | Consensus includes gb: BE786265 /FEA = EST /DB_XREF = gi: 10207463 /DB_XREF = est: 601474419F1 /CLONE = IMAGE: 3877253 /UG = Hs.197680 ESTs |
| 214233_AT | 1.086061876 | golgi associated, gamma adaptin ear containing, ARF binding protein 2 |
| 200757_S_AT | 1.090523795 | calumenin |
| 226009_AT | 1.091675591 | DKFZP566F084 protein |
| 209165_AT | 1.093925622 | apoptosis antagonizing transcription factor |
| 78495_AT | 1.107305608 | hypothetical protein DKFZp762P2111 |
| 225844_AT | 1.109360529 | DNA polymerase epsilon p12 subunit |
| 217750_S_AT | 1.115000533 | hypothetical protein FLJ13855 |
| 208205_AT | 1.116111337 | protocadherin alpha 9 |
| 239332_AT | 1.119141184 | Consensus includes gb: AW079559 /FEA = EST /DB_XREF = gi: 6034711 /DB_XREF = est: xc18f10.x1 /CLONE = IMAGE: 2584651 /UG = Hs.152258 ESTs |

-continued

| Probe ID | Fold change | Description |
|---|---|---|
| 203452_AT | 1.12034557 | beta-1,3-glucuronyltransferase 3 (glucuronosyltransferase I) |
| 203769_S_AT | 1.121150341 | steroid sulfatase (microsomal), arylsulfatase C, isozyme S |
| 218567_X_AT | 1.122805511 | dipeptidylpeptidase III |
| 226035_AT | 1.125175582 | KIAA1203 protein |
| 229973_AT | 1.126903087 | Consensus includes gb: AI827930 /FEA = EST /DB_XREF = gi: 5448688 /DB_XREF = est: wf34g12.x1 /CLONE = IMAGE: 2357542 /UG = Hs.101277 ESTs |
| 202185_AT | 1.127345516 | procollagen-lysine, 2-oxoglutarate 5-dioxygenase 3 |
| 205477_S_AT | 1.13600702 | alpha-1-microglobulin/bikunin precursor |
| 213491_X_AT | 1.13811761 | ribophorin II |
| 218627_AT | 1.138900807 | hypothetical protein FLJ11259 |
| 208923_AT | 1.139946131 | cytoplasmic FMR1 interacting protein 1 |
| 210704_AT | 1.139987733 | fasciculation and elongation protein zeta 2 (zygin II) |
| 203878_S_AT | 1.141566576 | matrix metalloproteinase 11 (stromelysin 3) |
| 204693_AT | 1.144371005 | CDC42 effector protein (Rho GTPase binding) 1 |
| 244876_AT | 1.146593337 | Consensus includes gb: BF112140 /FEA = EST /DB_XREF = gi: 10941830 /DB_XREF = est: 7l40g11.x1 /CLONE = IMAGE: 3524156 /UG = Hs.191950 ESTs |
| 233959_AT | 1.146921579 | Consensus includes gb: W26606 /FEA = EST /DB_XREF = gi: 1307584 /DB_XREF = est: 35e8 /UG = Hs.136141 Human DNA sequence from clone RP1-238O23 on chromosome 6. Contains part of the gene for a novel protein similar to PIGR (polymeric immunoglobulin receptor), part of |
| 225185_AT | 1.147781598 | muscle RAS oncogene homolog |
| 213399_X_AT | 1.148580043 | ribophorin II |
| 225303_AT | 1.151887802 | Consensus includes gb: AI049973 /FEA = EST /DB_XREF = gi: 3299090 /DB_XREF = est: an38g03.x1 /CLONE = IMAGE: 1700980 /UG = Hs.170142 ESTs |
| 204558_AT | 1.152762332 | RAD54-like (*S. cerevisiae*) |
| 210988_S_AT | 1.153420605 | TcD37 homolog |
| 235571_AT | 1.155082902 | Consensus includes gb: AW300953 /FEA = EST /DB_XREF = gi: 6710630 /DB_XREF = est: xk10b12.x1 /CLONE = IMAGE: 2666303 /UG = Hs.195641 ESTs |
| 228479_AT | 1.155662152 | Consensus includes gb: AI094180 /FEA = EST /DB_XREF = gi: 3433156 /DB_XREF = est: qa29b09.s1 /CLONE = IMAGE: 1688153 /UG = Hs.15702 ESTs |
| 230326_S_AT | 1.157284643 | hypothetical protein |
| 216427_AT | 1.158279318 | *Homo sapiens* cDNA: FLJ22786 fis, clone KAIA2150 |
| 238809_AT | 1.158640219 | Consensus includes gb: BF439305 /FEA = EST /DB_XREF = gi: 11451822 /DB_XREF = est: nab62f12.x1 /CLONE = IMAGE: 3272590 /UG = Hs.154929 ESTs |
| 230381_AT | 1.158734789 | Consensus includes gb: AI587638 /FEA = EST /DB_XREF = gi: 4574079 /DB_XREF = est: tr80b03.x1 /CLONE = IMAGE: 2224589 /UG = Hs.97258 ESTs, Moderately similar to S29539 ribosomal protein L13a, cytosolic *H. sapiens* |
| 213832_AT | 1.159098844 | *Homo sapiens* clone 24405 mRNA sequence |
| 209946_AT | 1.16170491 | vascular endothelial growth factor C |
| 223626_X_AT | 1.162485201 | TLH29 protein precursor |
| 210605_S_AT | 1.163276135 | milk fat globule-EGF factor 8 protein |
| 207413_S_AT | 1.163398138 | sodium channel, voltage-gated, type V, alpha polypeptide (long (electrocardiographic) QT syndrome 3) |
| 209506_S_AT | 1.163479951 | nuclear receptor subfamily 2, group F, member 1 |
| 201797_S_AT | 1.165527424 | valyl-tRNA synthetase 2 |
| 211587_X_AT | 1.166963712 | cholinergic receptor, nicotinic, alpha polypeptide 3 |
| 222688_AT | 1.16706248 | alkaline phytoceramidase |
| 231496_AT | 1.16918117 | FKSG87 protein |
| 211241_AT | 1.169510286 | annexin A2 pseudogene 3 |
| 214719_AT | 1.171387212 | *Homo sapiens* cDNA: FLJ23067 fis, clone LNG04993 |
| 218358_AT | 1.173982864 | hypothetical protein MGC11256 |
| 218634_AT | 1.174349756 | pleckstrin homology-like domain, family A, member 3 |
| 231411_AT | 1.176079104 | lipoma HMGIC fusion partner |
| 202686_S_AT | 1.177256183 | AXL receptor tyrosine kinase |
| 204215_AT | 1.177923094 | hypothetical protein MGC4175 |
| 209641_S_AT | 1.180297137 | ATP-binding cassette, sub-family C (CFTR/MRP), member 3 |
| 228937_AT | 1.181527084 | Consensus includes gb: AI659800 /FEA = EST /DB_XREF = gi: 4763370 /DB_XREF = est: tu03b01.x1 /CLONE = IMAGE: 2249929 /UG = Hs.24250 ESTs |
| 216194_S_AT | 1.182566653 | cytoskeleton-associated protein 1 |
| 208837_AT | 1.182670307 | integral type I protein |
| 212566_AT | 1.182737899 | microtubule-associated protein 4 |
| 32402_S_AT | 1.183160054 | symplekin; Huntingtin interacting protein I |
| 207752_X_AT | 1.184738166 | proline-rich protein BstNI subfamily 1 |
| 227776_AT | 1.185536023 | Consensus includes gb: BF589251 /FEA = EST /DB_XREF = gi: 11681575 /DB_XREF = est: nab29d09.x1 /CLONE = IMAGE: 3267137 /UG = Hs.27172 ESTs |
| 202336_S_AT | 1.185997937 | peptidylglycine alpha-amidating monooxygenase |
| 221739_AT | 1.186943284 | interleukin 27 |

| Probe ID | Fold change | Description |
|---|---|---|
| 207714_S_AT | 1.189557616 | serine (or cysteine) proteinase inhibitor, clade H (heat shock protein 47), member 1, (collagen binding protein 1) |
| 219768_AT | 1.196282401 | hypothetical protein FLJ22418 |
| 224893_AT | 1.19715819 | Consensus includes gb: AA775408 /FEA = EST /DB_XREF = gi: 2834742 /DB_XREF = est: ad13b10.s1 /CLONE = IMAGE: 878107 /UG = Hs.93659 protein disulfide isomerase related protein (calcium-binding protein, intestinal-related) |
| 222288_AT | 1.19731715 | ESTs, Weakly similar to hypothetical protein FLJ20489 [*Homo sapiens*] [*H. sapiens*] |
| 202800_AT | 1.198273846 | solute carrier family 1 (glial high affinity glutamate transporter), member 3 |
| 225190_X_AT | 1.199233799 | ribosomal protein L35a |
| 226000_AT | 1.199543769 | hypothetical protein DKFZp547A023 |
| 224710_AT | 1.201989922 | RAB34, member RAS oncogene family |
| 223551_AT | 1.202954395 | protein kinase (cAMP-dependent, catalytic) inhibitor beta |
| 212680_X_AT | 1.203327214 | protein phosphatase 1, regulatory (inhibitor) subunit 14B |
| 200654_AT | 1.203766272 | procollagen-proline, 2-oxoglutarate 4-dioxygenase (proline 4-hydroxylase), beta polypeptide (protein disulfide isomerase; thyroid hormone binding protein p55) |
| 202117_AT | 1.204302402 | Rho GTPase activating protein 1 |
| 209574_S_AT | 1.204484226 | chromosome 18 open reading frame 1 |
| 201944_AT | 1.206435219 | hexosaminidase B (beta polypeptide) |
| 209925_AT | 1.208021557 | occludin |
| 208658_AT | 1.2107325 | protein disulfide isomerase related protein (calcium-binding protein, intestinal-related) |
| 203423_AT | 1.210740011 | retinol binding protein 1, cellular |
| 224928_AT | 1.211727589 | KIAA1717 protein |
| 212013_AT | 1.213796445 | Melanoma associated gene |
| 209869_AT | 1.215037002 | adrenergic, alpha-2A-, receptor |
| 227752_AT | 1.216047557 | Consensus includes gb: AA005105 /FEA = EST /DB_XREF = gi: 1448894 /DB_XREF = est: zh96f09.s1 /CLONE = IMAGE: 429161 /UG = Hs.18441 ESTs |
| 224531_AT | 1.216607034 | G protein-coupled receptor 61 |
| 206860_S_AT | 1.218715307 | hypothetical protein FLJ20323 |
| 204589_AT | 1.220213502 | KIAA0537 gene product |
| 244602_AT | 1.221077865 | Consensus includes gb: AI638020 /FEA = EST /DB_XREF = gi: 4690254 /DB_XREF = est: tt06b06.x1 /CLONE = IMAGE: 2239955 /UG = Hs.313651 ESTs |
| 238604_AT | 1.22368523 | Consensus includes gb: AA768884 /FEA = EST /DB_XREF = gi: 2820122 /DB_XREF = est: nz82e07.s1 /CLONE = IMAGE: 1301988 /UG = Hs.140489 ESTs |
| 228315_AT | 1.225992752 | Consensus includes gb: AI632728 /FEA = EST /DB_XREF = gi: 4684058 /DB_XREF = est: wa33e10.x1 /CLONE = IMAGE: 2299914 /UG = Hs.25144 ESTs |
| 218007_S_AT | 1.225996491 | ribosomal protein S27-like |
| 200095_X_AT | 1.226683191 | ribosomal protein S10 |
| 205151_S_AT | 1.226985415 | KIAA0644 gene product |
| 203954_X_AT | 1.228367034 | claudin 3 |
| 225102_AT | 1.229843848 | Consensus includes gb: BG168471 /FEA = EST /DB_XREF = gi: 12675184 /DB_XREF = est: 602339623F1 /CLONE = IMAGE: 4447685 /UG = Hs.3964 *Homo sapiens* clone 24877 mRNA sequence |
| 201792_AT | 1.230026928 | AE binding protein 1 |
| 226801_S_AT | 1.23180185 | hypothetical protein FLJ12806 |
| 201011_AT | 1.231973181 | ribophorin I |
| 207134_X_AT | 1.232180791 | tryptase beta 2 |
| 200002_AT | 1.234728973 | ribosomal protein L35 |
| 208789_AT | 1.235881012 | polymerase I and transcript release factor |
| 204154_AT | 1.236601919 | cysteine dioxyenase, type I |
| 229256_AT | 1.236980622 | Consensus includes gb: AV724329 /FEA = EST /DB_XREF = gi: 10828609 /DB_XREF = est: AV724329 /CLONE = HTBAYE09 /UG = Hs.26612 ESTs |
| 206767_AT | 1.237061736 | RNA binding motif, single stranded interacting protein |
| 212865_S_AT | 1.237617756 | collagen, type XIV, alpha 1 (undulin) |
| 205622_AT | 1.23863447 | sphingomyelin phosphodiesterase 2, neutral membrane (neutral sphingomyelinase) |
| 227550_AT | 1.24163209 | Consensus includes gb: AW242720 /FEA = EST /DB_XREF = gi: 6576565 /DB_XREF = est: xm90c07.x1 /CLONE = IMAGE: 2691468 /UG = Hs.94694 *Homo sapiens* cDNA FLJ10561 fis, clone NT2RP2002672 |
| 227400_AT | 1.245481895 | nuclear factor I/X (CCAAT-binding transcription factor) |
| 227095_AT | 1.247538855 | Consensus includes gb: AU151151 /FEA = EST /DB_XREF = gi: 11012672 /DB_XREF = est: AU151151 /CLONE = NT2RP2004501 /UG = Hs.11493 *Homo sapiens* cDNA FLJ13536 fis, clone PLACE1006521 |
| 213993_AT | 1.249679508 | spondin 1, (f-spondin) extracellular matrix protein |
| 200091_S_AT | 1.249883518 | ribosomal protein S25 |

-continued

| Probe ID | Fold change | Description |
|---|---|---|
| 226769_AT | 1.25158845 | Consensus includes gb: AI802391 /FEA = EST /DB_XREF = gi: 5367863 /DB_XREF = est: tc33c04.x1 /CLONE = IMAGE: 2066406 /UG = Hs.32478 ESTs |
| 235343_AT | 1.252594587 | Consensus includes gb: AI961235 /FEA = EST /DB_XREF = gi: 5753948 /DB_XREF = est: wt15d02.x1 /CLONE = IMAGE: 2507523 /UG = Hs.96885 ESTs |
| 215489_X_AT | 1.25463764 | Homer, neuronal immediate early gene, 3 |
| 226227_X_AT | 1.255386587 | ribosomal protein L10 |
| 221253_S_AT | 1.255591702 | thioredoxin related protein |
| 225293_AT | 1.257051538 | KIAA1870 protein |
| 212070_AT | 1.257819537 | G protein-coupled receptor 56 |
| 201004_AT | 1.258887314 | signal sequence receptor, delta (translocon-associated protein delta) |
| 225524_AT | 1.260794285 | Consensus includes gb: AU152178 /FEA = EST /DB_XREF = gi: 11013699 /DB_XREF = est: AU152178 /CLONE = NT2RP3000356 /UG = Hs.5897 *Homo sapiens* mRNA; cDNA DKFZp586P1622 (from clone DKFZp586P1622) |
| 200025_S_AT | 1.266750238 | ribosomal protein L27 |
| 201798_S_AT | 1.267666985 | fer-1-like 3, myoferlin (*C. elegans*) |
| 200999_S_AT | 1.268554366 | cytoskeleton-associated protein 4 |
| 205047_S_AT | 1.272415146 | asparagine synthetase |
| 232568_AT | 1.273750665 | Consensus includes gb: AU145658 /FEA = EST /DB_XREF = gi: 11007179 /DB_XREF = est: AU145658 /CLONE = HEMBA1005426 /UG = Hs.287447 *Homo sapiens* cDNA FLJ11733 fis, clone HEMBA1005426 |
| 226731_AT | 1.277394682 | Consensus includes gb: AA156873 /FEA = EST /DB_XREF = gi: 1728488 /DB_XREF = est: zl20h08.s1 /CLONE = IMAGE: 502527 /UG = Hs.184411 albumin |
| 230708_AT | 1.278154867 | Consensus includes gb: AA206141 /FEA = EST /DB_XREF = gi: 1801529 /DB_XREF = est: zq54h06.s1 /CLONE = IMAGE: 645467 /UG = Hs.86237 ESTs |
| 224915_X_AT | 1.278690668 | ribosomal protein L10 |
| 224874_AT | 1.285040296 | Consensus includes gb: N32181 /FEA = EST /DB_XREF = gi: 1152580 /DB_XREF = est: yy25c09.s1 /CLONE = IMAGE: 272272 /UG = Hs.279591 *Homo sapiens* clone 25056 mRNA sequence |
| 221004_S_AT | 1.285059625 | integral membrane protein 3 |
| 218718_AT | 1.288837342 | platelet derived growth factor C |
| 223044_AT | 1.28976985 | solute carrier family 11 (proton-coupled divalent metal ion transporters), member 3 |
| 201540_AT | 1.29071587 | four and a half LIM domains 1 |
| 204073_S_AT | 1.291992594 | chromosome 11 open reading frame 9 |
| 209250_AT | 1.29301844 | degenerative spermatocyte homolog, lipid desaturase (*Drosophila*) |
| 212419_AT | 1.293633012 | *Homo sapiens*, similar to Y43E12A.2.p, clone MGC: 33537 IMAGE: 4821347, mRNA, complete cds |
| 210987_X_AT | 1.295835332 | tropomyosin 1 (alpha) |
| 235527_AT | 1.300030842 | Consensus includes gb: U55983 /FEA = EST /DB_XREF = gi: 1354539 /DB_XREF = est: HSU55983 /CLONE = 25150 /UG = Hs.290270 ESTs |
| 225868_AT | 1.300252579 | gene overexpressed in astrocytoma |
| 200088_X_AT | 1.302539027 | ribosomal protein L12 |
| 205582_S_AT | 1.306594707 | gamma-glutamyltransferase-like activity 1 |
| 201590_X_AT | 1.310067911 | annexin A2 |
| 207191_S_AT | 1.314983958 | immunoglobulin superfamily containing leucine-rich repeat |
| 221530_S_AT | 1.31612576 | basic helix-loop-helix domain containing, class B, 3 |
| 203570_AT | 1.320595376 | lysyl oxidase-like 1 |
| 233607_AT | 1.323745885 | Consensus includes gb: AU145679 /FEA = EST /DB_XREF = gi: 11007200 /DB_XREF = est: AU145679 /CLONE = HEMBA1005497 /UG = Hs.301626 *Homo sapiens* cDNA FLJ11739 fis, clone HEMBA1005497 |
| 212489_AT | 1.325150391 | collagen, type V, alpha 1 |
| 225541_AT | 1.334165509 | Bernardinelli-Seip congenital lipodystrophy 2 (seipin) |
| 219332_AT | 1.337767498 | hypothetical protein FLJ23471 |
| 238935_AT | 1.338252224 | Consensus includes gb: AW958475 /FEA = EST /DB_XREF = gi: 8148159 /DB_XREF = est: EST370545 /UG = Hs.293947 ESTs, Weakly similar to I38022 hypothetical protein *H. sapiens* |
| 217757_AT | 1.339761129 | alpha-2-macroglobulin |
| 213503_X_AT | 1.340824578 | annexin A2 |
| 227628_AT | 1.340990903 | Consensus includes gb: AL571557 /FEA = EST /DB_XREF = gi: 12928970 /DB_XREF = est: AL571557 /CLONE = CS0DI024YP08 (3 prime) /UG = Hs.252280 Rho guanine nucleotide exchange factor (GEF) 1 |
| 231579_S_AT | 1.341554022 | Consensus includes gb: BE968786 /FEA = EST /DB_XREF = gi: 10579491 /DB_XREF = est: 601649975F1 /CLONE = IMAGE: 3933691 /UG = Hs.6441 *Homo sapiens* mRNA; cDNA DKFZp586J021 (from clone DKFZp586J021) |
| 244498_X_AT | 1.341921008 | hypothetical protein FLJ22795 |
| 210427_X_AT | 1.357240325 | annexin A2 |
| 213258_AT | 1.358572258 | tissue factor pathway inhibitor (lipoprotein-associated coagulation inhibitor) |

| Probe ID | Fold change | Description |
|---|---|---|
| 228333_AT | 1.361484587 | Consensus includes gb: AI912571 /FEA = EST /DB_XREF = gi: 5632426 /DB_XREF = est: we11c04.x1 /CLONE = IMAGE: 2340774 /UG = Hs.293676 ESTs |
| 228376_AT | 1.367416558 | Consensus includes gb: AI972498 /FEA = EST /DB_XREF = gi: 5769244 /DB_XREF = est: wr38c04.x1 /CLONE = IMAGE: 2489958 /UG = Hs.97469 ESTs, Highly similar to A39769 N-acetyllactosaminide alpha-1,3-galactosyltransferase *H. sapiens* |
| 202992_AT | 1.369860753 | complement component 7 |
| 216589_AT | 1.369973892 | Consensus includes gb: AL031276 /DEF = Human DNA sequence from clone 1118D24 on chromosome 1p36.11–36.33. Contains part of a novel gene similar to worm genes T08G11.1 and C25H3.9, part of a 60S Ribosomal Protein L10 LIKE (pseudo)gene and two 3 exons of the TNFR2 gene for Tumor Necrosi . . . /FEA = CDS_3 /DB_XREF = gi: 3947780 /UG = Hs.247773 Human DNA sequence from clone 1118D24 on chromosome 1p36.11–36.33. Contains part of a novel gene similar to worm genes T08G11.1 and C25H3.9, part of a 60S Ribosomal Protein L10 LIKE (pseudo)gene and two 3 exons of the TNFR2 gene for Tumor Necrosis Factor |
| 231956_AT | 1.37058989 | KIAA1618 protein |
| 232914_S_AT | 1.374130669 | synaptotagmin-like 2 |
| 206336_AT | 1.374366046 | chemokine (C—X—C motif) ligand 6 (granulocyte chemotactic protein 2) |
| 201939_AT | 1.381746061 | serum-inducible kinase |
| 201189_S_AT | 1.387216871 | inositol 1,4,5-triphosphate receptor, type 3 |
| 230061_AT | 1.39036339 | Consensus includes gb: AW338625 /FEA = EST /DB_XREF = gi: 6835251 /DB_XREF = est: ha63a02.x1 /CLONE = IMAGE: 2878346 /UG = Hs.22120 ESTs |
| 212646_AT | 1.391579711 | KIAA0084 protein |
| 212190_AT | 1.397987102 | serine (or cysteine) proteinase inhibitor, clade E (nexin, plasminogen activator inhibitor type 1), member 2 |
| 211340_S_AT | 1.398229327 | melanoma cell adhesion molecule |
| 214247_S_AT | 1.399778156 | dickkopf homolog 3 (*Xenopus laevis*) |
| 225725_AT | 1.399942478 | Consensus includes gb: AL533234 /FEA = EST /DB_XREF = gi: 12796727 /DB_XREF = est: AL533234 /CLONE = CS0DN003YO15 (3 prime) /UG = Hs.26418 ESTs |
| 218960_AT | 1.401709562 | transmembrane protease, serine 4 |
| 200986_AT | 1.402768462 | serine (or cysteine) proteinase inhibitor, clade G (C1 inhibitor), member 1, (angioedema, hereditary) |
| 225520_AT | 1.404939056 | Consensus includes gb: AL133260 /DEF = Human DNA sequence from clone RP1-292B18 on chromosome 6q24.3-25.3. Contains a 60S ribosomal protein L32 (RPL32) pseudogene, the 3 end of the gene for a novel protein similar to NADP+ dependent methylenetetrahydrofolat |
| 213332_AT | 1.410529364 | *Homo sapiens* cDNA FLJ39399 fis, clone PLACE6011041 |
| 210986_S_AT | 1.415326446 | tropomyosin 1 (alpha) |
| 201012_AT | 1.41609642 | annexin A1 |
| 214770_AT | 1.418908197 | macrophage scavenger receptor 1 |
| 222925_AT | 1.420398606 | RU2S |
| 203476_AT | 1.428852653 | trophoblast glycoprotein |
| 210933_S_AT | 1.42941576 | hypothetical protein MGC4655 |
| 209708_AT | 1.435248054 | DKFZP564G202 protein |
| 200795_AT | 1.437745827 | SPARC-like 1 (mast9, hevin) |
| 217360_X_AT | 1.44066345 | Consensus includes gb: AJ275408 /DEF = *Homo sapiens* partial IGVH3 gene for immunoglobulin heavy chain V region, case 1, cell Mo VI 162 /FEA = CDS /DB_XREF = gi: 7573079 /UG = Hs.272363 *Homo sapiens* partial IGVH3 gene for immunoglobulin heavy chain V region, case 1, cell Mo VI 162 |
| 211719_X_AT | 1.441332362 | fibronectin 1 |
| 210495_X_AT | 1.444417445 | fibronectin 1 |
| 202766_S_AT | 1.445284138 | fibrillin 1 (Marfan syndrome) |
| 224694_AT | 1.446756925 | tumor endothelial marker 8 |
| 234994_AT | 1.456358161 | KIAA1913 protein |
| 223395_AT | 1.456915192 | DKFZP586L2024 protein |
| 209114_AT | 1.463996851 | tetraspan 1 |
| 201141_AT | 1.470896057 | glycoprotein (transmembrane) nmb |
| 212464_S_AT | 1.471667088 | fibronectin 1 |
| 230865_AT | 1.473488244 | Consensus includes gb: N29837 /FEA = EST /DB_XREF = gi: 1148357 /DB_XREF = est: yw93e11.s1 /CLONE = IMAGE: 259820 /UG = Hs.25205 ESTs |
| 216442_X_AT | 1.481522822 | fibronectin 1 |
| 202403_S_AT | 1.498542655 | collagen, type I, alpha 2 |
| 205044_AT | 1.500072626 | gamma-aminobutyric acid (GABA) A receptor, pi |
| 218002_S_AT | 1.50143269 | chemokine (C—X—C motif) ligand 14 |
| 205890_S_AT | 1.501834772 | ubiquitin D |
| 222549_AT | 1.504922194 | claudin 1 |
| 227006_AT | 1.508429008 | protein phosphatase 1, regulatory (inhibitor) subunit 14A |
| 228367_AT | 1.508627522 | heart alpha-kinase |
| 203477_AT | 1.51069519 | collagen, type XV, alpha 1 |
| 214321_AT | 1.52285407 | nephroblastoma overexpressed gene |

| Probe ID | Fold change | Description |
| --- | --- | --- |
| 239519_AT | 1.533746711 | Consensus includes gb: AA927670 /FEA = EST /DB_XREF = gi: 3076490 /DB_XREF = est: om72a05.s1 /CLONE = IMAGE: 1552688 /UG = Hs.131704 ESTs |
| 207173_X_AT | 1.536504615 | cadherin 11, type 2, OB-cadherin (osteoblast) |
| 228750_AT | 1.542651522 | Consensus includes gb: AI693516 /FEA = EST /DB_XREF = gi: 4970856 /DB_XREF = est: wd43e03.x1 /CLONE = IMAGE: 2330908 /UG = Hs.28625 ESTs |
| 201438_AT | 1.545904663 | collagen, type VI, alpha 3 |
| 204933_S_AT | 1.564410582 | tumor necrosis factor receptor superfamily, member 11b (osteoprotegerin) |
| 203798_S_AT | 1.575116185 | visinin-like 1 |
| 225681_AT | 1.58766942 | Consensus includes gb: AA584310 /FEA = EST /DB_XREF = gi: 2368919 /DB_XREF = est: nn79g01.s1 /CLONE = IMAGE: 1090128 /UG = Hs.283713 ESTs, Weakly similar to ORF YGL050w *S. cerevisiae* |
| 213994_S_AT | 1.600995219 | spondin 1, (f-spondin) extracellular matrix protein |
| 201645_AT | 1.601544517 | tenascin C (hexabrachion) |
| 204150_AT | 1.60514469 | stabilin 1 |
| 204438_AT | 1.607478454 | mannose receptor, C type 1 |
| 226621_AT | 1.608496225 | fibrinogen, gamma polypeptide |
| 202404_S_AT | 1.625425914 | collagen, type I, alpha 2 |
| 219359_AT | 1.625667544 | hypothetical protein FLJ22635 |
| 221872_AT | 1.625850269 | retinoic acid receptor responder (tazarotene induced) 1 |
| 209774_X_AT | 1.632070072 | chemokine (C—X—C motif) ligand 2 |
| 205547_S_AT | 1.652144874 | transgelin |
| 217767_AT | 1.652843581 | complement component 3 |
| 223218_S_AT | 1.67088194 | molecule possessing ankyrin repeats induced by lipopolysaccharide (MAIL), homolog of mouse |
| 214803_AT | 1.680222335 | *Homo sapiens* mRNA; cDNA DKFZp564N1116 (from clone DKFZp564N1116) |
| 209960_AT | 1.693139918 | hepatocyte growth factor (hepapoietin A; scatter factor) |
| 204304_S_AT | 1.708433923 | prominin-like 1 (mouse) |
| 201852_X_AT | 1.713217834 | collagen, type III, alpha 1 (Ehlers-Danlos syndrome type IV, autosomal dominant) |
| 208451_S_AT | 1.716268712 | complement component 4B |
| 215076_S_AT | 1.717776215 | collagen, type III, alpha 1 (Ehlers-Danlos syndrome type IV, autosomal dominant) |
| 204932_AT | 1.721284296 | tumor necrosis factor receptor superfamily, member 11b (osteoprotegerin) |
| 201744_S_AT | 1.752427367 | lumican |
| 216598_S_AT | 1.771133304 | chemokine (C—C motif) ligand 2 |
| 201666_AT | 1.797990004 | tissue inhibitor of metalloproteinase 1 (erythroid potentiating activity, collagenase inhibitor) |
| 202357_S_AT | 1.812934811 | B-factor, properdin |
| 211161_S_AT | 1.814980251 | gb: AF130082.1 /DEF = *Homo sapiens* clone FLC1492 PRO3121 mRNA, complete cds. /FEA = mRNA /PROD = PRO3121 /DB_XREF = gi: 11493468 /UG = Hs.119571 collagen, type III, alpha 1 (Ehlers-Danlos syndrome type IV, autosomal dominant) /FL = gb: AF130082.1 |
| 229659_S_AT | 1.847078972 | Consensus includes gb: BE501712 /FEA = EST /DB_XREF = gi: 9704120 /DB_XREF = est: hw34c04.x1 /CLONE = IMAGE: 3184806 /UG = Hs.205126 *Homo sapiens* cDNA: FLJ22667 fis, clone HSI08385 |
| 203868_S_AT | 1.8584063 | vascular cell adhesion molecule 1 |
| 214428_X_AT | 1.868320095 | complement component 4A |
| 202238_S_AT | 1.872072166 | nicotinamide N-methyltransferase |
| 203892_AT | 1.925641314 | WAP four-disulfide core domain 2 |
| 208747_S_AT | 1.967306306 | complement component 1, s subcomponent |
| 227140_AT | 1.974210876 | Consensus includes gb: AI343467 /FEA = EST /DB_XREF = gi: 4080673 /DB_XREF = est: tb97a02.x1 /CLONE = IMAGE: 2062250 /UG = Hs.28792 *Homo sapiens* cDNA FLJ11041 fis, clone PLACE1004405 |
| 202310_S_AT | 1.986878496 | collagen, type I, alpha 1 |
| 226147_S_AT | 2.017873731 | Consensus includes gb: AA838075 /FEA = EST /DB_XREF = gi: 2913732 /DB_XREF = est: oe93h05.s1 /CLONE = IMAGE: 1419225 /UG = Hs.205126 *Homo sapiens* cDNA: FLJ22667 fis, clone HSI08385 |
| 226535_AT | 2.072503948 | Consensus includes gb: AK026736.1 /DEF = *Homo sapiens* cDNA: FLJ23083 fis, clone LNG06541, highly similar to IR2005735 *Homo sapiens* mRNA full length insert cDNA clone EUROIMAGE 2005735. /FEA = mRNA /DB_XREF = gi: 10439657 /UG = Hs.57664 *Homo sapiens* mRNA full leng |
| 225353_S_AT | 2.090924327 | Consensus includes gb: AI184968 /FEA = EST /DB_XREF = gi: 3735606 /DB_XREF = est: qe51c05.x1 /CLONE = IMAGE: 1742504 /UG = Hs.94953 ESTs, Highly similar to C1HUQC complement subcomponent C1q chain C precursor *H. sapiens* |
| 202953_AT | 2.158512953 | complement component 1, q subcomponent, beta polypeptide |
| 212067_S_AT | 2.168640328 | complement component 1, r subcomponent |
| 218232_AT | 2.186166831 | complement component 1, q subcomponent, alpha polypeptide |
| 227697_AT | 2.191502539 | STAT induced STAT inhibitor 3 |

-continued

| Probe ID | Fold change | Description |
|---|---|---|
| 216834_AT | 2.470272934 | regulator of G-protein signalling 1 |
| 217239_X_AT | 2.49895167 | Consensus includes gb: AF044592 /DEF = *Homo sapiens* lymphocyte-predominant Hodgkins disease case 4 immunoglobulin heavy chain gene, variable region, partial cds /FEA = CDS /DB_XREF = gi: 2852420 /UG = Hs.248077 *Homo sapiens* lymphocyte-predominant Hodgkins disease case 4 immunoglobulin heavy chain gene, variable region, partial cds |
| 202988_S_AT | 2.51395452 | regulator of G-protein signalling 1 |
| 202018_S_AT | 2.589367704 | lactotransferrin |
| 244567_AT | 2.77086294 | CLONE = IMAGE: 4453556 /UG = Hs.125395 ESTs |
| 204259_AT | 2.900639089 | matrix metalloproteinase 7 (matrilysin, uterine) |
| 202237_AT | 2.933157011 | nicotinamide N-methyltransferase |

Genes are identified by Affymetrix Probe ID in the first column, and are arranged in order of fold change over a span of 50 years (second column). Gene descriptions are in the third column. All of the Affymetrix data are available at the Stanford Microarray Database and at the Web site, herein specifically incorporated by reference.

Nucleic Acids. The nucleic acid sequences of genes associated with aging find various uses, including the preparation of arrays and other probes for hybridization, for the recombinant production of encoded polypeptides, and the like. The nucleic acids include those having a high degree of sequence similarity or sequence identity to the human genes set forth in Tables 1, 2 and 3. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to one of the sequences under stringent hybridization conditions.

Probes specific to the nucleic acid of the invention can be generated using publicly available nucleic acid sequences. The probes are preferably at least about 18 nt, 25 nt, 50 nt or more of the corresponding contiguous sequence of one of the sequences provided in Tables 1-3, and are usually less than about 2, 1, or 0.5 kb in length. Preferably, probes are designed based on a contiguous sequence that remains unmasked following application of a masking program for masking low complexity, e.g. BLASTX. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Polypeptides. Polypeptides encoded by the age associated genes may find uses. Such polypeptides include native forms, derivative, and fragments thereof. Peptides of interest include fragments of at least about 12 contiguous amino acids, more usually at least about 20 contiguous amino acids, and may comprise 30 or more amino acids, up to the provided peptide, and may extend further to comprise other sequences present in, e.g. precursor polypeptides.

The sequence of the polypeptides may be altered in various ways known in the art to generate targeted changes in sequence, e.g. differing by at least one amino acid, and may differ by at least two but not more than about ten amino acids. The sequence changes may be substitutions, insertions or deletions.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

Antibodies. Antibodies specific for the polypeptides of age-associated genes find uses in some embodiments. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage display libraries, usually in conjunction with in vitro affinity maturation.

Screening Methods. The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue harvested from a subject to be diagnosed, e.g., via blood drawing, biopsy of tissue, using standard protocols, where cell types or tissues from which such nucleic acids may be generated include any tissue in which the expression pattern of the to be determined phenotype exists. Cells may be cultured prior to analysis.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos.: 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acid provides information regarding expression for each of the genes that have been probed, where the expression information is in terms of whether or not the gene is expressed and, typically, at what level, where the expression data, i.e., expression profile, may be both qualitative and quantitative.

Alternatively, non-array based methods for quantitating the levels of one or more nucleic acids in a sample may be employed, including quantitative PCR, and the like.

Where the expression profile is a protein expression profile, any convenient protein quantitation protocol may be employed, where the levels of one or more proteins in the assayed sample are determined. Representative methods include, but are not limited to; proteomic arrays, flow cytometry, standard immunoassays, etc.

Reagents and Kits. Also provided are reagents and kits thereof for practicing one or more of the above-described methods. The subject reagents and kits thereof may vary greatly. Reagents of interest include reagents specifically designed for use in production of the above described expression profiles of phenotype determinative genes.

One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos.: 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In certain embodiments, the number of genes that are represented on the array are at least 10, usually at least 25, and may be at least 50, 100, up to including all of the genes listed, preferably utilizing the top ranked set of genes. The subject arrays may include only those genes that are listed, or they may include additional genes that are not listed. Where the subject arrays include probes for such additional genes, in certain embodiments the number % of additional genes that are represented does not exceed about 50%, usually does not exceed about 25%. In many embodiments where additional genes are included, a great majority of genes in the collection are age associated genes, where by great majority is meant at least about 75%, usually at least about 80% and sometimes at least about 85, 90, 95% or higher, including embodiments where 100% of the genes in the collection are age associated genes.

Another type of reagent that is specifically tailored for generating expression profiles of age associated genes is a collection of gene specific primers that is designed to selectively amplify such genes, for use in quantitative PCR and other quantitation methods. Gene specific primers and methods for using the same are described in U.S. Pat. No. 5,994,076, the disclosure of which is herein incorporated by reference. Of particular interest are collections of gene specific primers that have primers for at least 10 of the genes listed, often a plurality of these genes, e.g., at least 25, and may be 50, 100 or more to include all of the genes listed for a signature of interest. The subject gene specific primer collections may include only those genes that are listed, or they may include primers for additional genes that are not listed. Where the subject arrays include probes for such additional genes, in certain embodiments the number % of additional genes that are represented does not exceed about 50%, usually does not exceed about 25%. In many embodiments where additional genes are included, a great majority of genes in the collection are age associated genes, where by great majority is meant at least about 75%, usually at least about 80% and sometimes at least about 85, 90, 95% or higher, including embodiments where 100% of the genes in the collection are age associated genes.

The kits of the subject invention may include the above described arrays and/or gene specific primer collections. The kits may further include a software package for statistical analysis of one or more phenotypes, and may include a reference database for calculating the probability of susceptibility. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Compound Screening and Analysis of Therapy. The methods of the invention find use in screening tissues, cells, organs, etc. for a determination of physiological age. In such assays, an age signature is determined for the sample of interest, and used to assess the physiological age. The methods of the invention also find use in screening assays for agents that modulate aging. Such methods usually involve contacting cells, e.g. aged cells, with a candidate agent, and determining the change in expression of the markers provided herein in response to said treatment. In some embodiments, the cells are muscle cells, e.g. cardiac muscle, skeletal muscle, smooth muscle, satellite cells (muscle stem cells); and the like. In other embodiments, the cells are kidney cells, e.g. tubule cells, kidney organ cultures, glomeruli, cortex, and the like. In other embodiments, the cells are other than kidney or brain, e.g. skin cells such as keratinocytes, fibroblasts, epithelial cells, blood cells, e.g. leukocytes, endothelial cells, etc.

In some embodiments, the cells are provided in an in vitro culture environment, for example as a tissue section, primary cell culture, cell line, combination of cells, and the like. In other embodiments, the cells are provided in an in vivo environment, for example an animal model for age in pre-clinical trials, or human subjects in clinical trials and to follow the efficacy of therapeutic regimens. A review of animal models for age may be found at Narayanaswamy et al. (2000) Journal of Vascular and Interventional Radiology 11:5-17, herein incorporated by reference with respect to the use of various animal models.

Following exposure to the candidate compound, the panel of biomarkers is assessed for expression levels, for example in the absence or presence of the agent; in a time course following administration; in combination with other biologically active agents; in combination with non-pharmacologic therapy; and the like.

The compounds are typically added in solution, or readily soluble form, to the culture or animal. A plurality of assays may be run in parallel with different compound concentrations to obtain a differential response to the various concentrations. As known in the art, determining the effective concentration of a compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection.

Compounds of interest encompass numerous chemical classes, though typically they are organic molecules. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, etc.

Compounds and candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents that modulate activity of age associated proteins provide a point of therapeutic or prophylactic intervention. Numerous agents are useful in modulating this activity, including agents that directly modulate expression, e.g. expression vectors, antisense specific for the targeted gene; and agents that act on the protein, e.g. specific antibodies and analogs thereof, small organic molecules that block biological activity, etc.

Antisense molecules can be used to down-regulate expression in cells. The antisense reagent may be antisense oligo-nucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

In one embodiment of the invention, RNAi technology is used. As used herein, RNAi technology refers to a process in which double-stranded RNA is introduced into cells expressing a candidate gene to inhibit expression of the candidate gene, i.e., to "silence" its expression. The dsRNA is selected to have substantial identity with the candidate gene. In general such methods initially involve transcribing a nucleic acids containing all or part of a candidate gene into single- or double-stranded RNA. Sense and anti-sense RNA strands are allowed to anneal under appropriate conditions to form dsRNA. The resulting dsRNA is introduced into cells via various methods. Usually the dsRNA consists of two separate complementary RNA strands. However, in some instances, the dsRNA may be formed by a single strand of RNA that is self-complementary, such that the strand loops back upon itself to form a hairpin loop. Regardless of form, RNA duplex formation can occur inside or outside of a cell.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

A number of options can be utilized to deliver the dsRNA into a cell or population of cells. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Transcriptional Profile of Aging in the Human Kidney

Results

To procure material for analyzing changes in gene expression with age in the human kidney, we obtained kidney samples from normal tissue removed at nephrectomy for either removal of a tumor or for transplantation from 74 patients ranging in age from 27 to 92 y. We dissected each of the 74 kidney samples into cortex (72 samples) and medulla (62 samples) sections, isolated total RNA from each section, synthesized biotinylated complementary RNA (cRNA), and hybridized the labeled cRNA to Affymetrix high-density oligonucleotide arrays (HG-U133A and HG-U133B, containing a total of 44,928 probe sets corresponding to approximately 33,000 well-substantiated human genes). The level of expression for each gene was determined using DChip. Using our dataset, the expression level for every gene as a function of age could be plotted. For example, the expression of CDO1 (which encodes a cysteine dioxygenase type 1 protein) tended to increase with age. There was also variation between subjects and between the cortex and the medulla. Nearly all of the variation represents true differences between samples, as very little variation was observed when we performed repeat hybridizations using the same tissue sample.

We used a linear regression model to identify genes that showed a statistically significant change in expression with age (i.e., were age-regulated). We saw large differences in expression between tissue types and between the sexes. These differences were of similar magnitude for both young and old subjects, so that aging in one tissue (or sex) typically ran parallel to aging in the other. Our linear regression model allowed for these parallel trends; reasons for arriving at such a model are given below. Mathematically, our model takes the form $$Y_{ij}=\beta_{0j}+\beta_{1j}Age_i+\beta_{2j}Sex_i+\beta_{3j}Tissue_i+\epsilon_{ij}.\quad(1)$$

In equation 1, $Y_{ij}$ is the base 2 logarithm of the expression level for gene j in sample i, $Age_i$ is the age in years of the subject contributing sample i, $Sex_i$ is one if sample i came from a male subject (and zero for female), $Tissue_i$ is one if sample i was a medulla sample (and zero for cortex), and $\epsilon_{ij}$ is a random error term. The coefficients $\beta_{kj}$ for k=0, 1, 2, and 3 are values to be estimated from data. Our primary interest is in $\beta_{1j}$, which describes how quickly the expression of gene j changes with age, with $\beta_{1j}=0$ for genes with no linear age relationship.

In model 1 and others that we considered, the coefficients were estimated by least squares. The estimated values $\hat{\beta}_{kj}$ can differ from zero, even when the true coefficient is zero. We judged statistical significance through p-values, where a value of pij near zero corresponds to a large absolute value $|\hat{\beta}_{kj}|$ unlikely to have arisen by chance. Such p-values do not distinguish genes that increase with age from those that decrease with age. We also use one-tailed p-values, written P̃kj, taking values near zero to be significantly decreasing trends and those near one to be significantly increasing trends.

To make p-values comparable over genes, it is essential to use the same model for all genes. Before settling on the common model 1, we considered an alternative that allowed a quadratic trend in age. The P̃-values for the quadratic coefficient gave no reason to suspect that a curved relationship was needed. Similarly, a piecewise linear age relationship (with bends at ages 50 and 70) was not significantly better than a linear one. Large and statistically significant differences in expression were found for the two tissue types, and so the tissue type was included in equation 1. Incorporating tissue type into the model reduces the estimate of the noise variance, leading to greater power for detecting an age relationship. Similarly, a small number of genes were found to have significantly different expression between sexes. Seven genes were found to have a difference at p<0.001 for both sex and age.

We performed a genome-wide scan for genes that changed expression with respect to age. Age-regulated genes can be identified by plotting P̃-values for age based on model 1 (FIG. 1B). Genes that significantly decrease in expression with age appear in a peak on the left, while those whose expression increases with age are in a peak at the right. Using model 1, we found 985 genes that change with respect to age (p<0.001), which is considerably greater than would be expected by chance (approximately 45 from a total of 44,928 genes). Of these, 742 genes increase expression with age and 243 decrease expression with age.

Most of our samples were taken from patients that underwent nephrectomy for various medical reasons. We evaluated whether pathology, medical history, or medication might be factors that confounded our aging analysis. For example, if old people tend to be hypertensive more often than young, then genes that respond to hypertension may appear to be age-related.

We identified 20 different medical and other factors that might potentially confound our study, including race, blood pressure, diabetes, and type and size of tumor present in the kidney. Fourteen factors (such as diabetes or proteinuria) affected less than ten patients, making it unlikely that they could account for age-related change in gene expression in the 74 patients analyzed. Six factors occurred in ten or more patients (non-white race, two types of tumors, size of tumor, and hypertension), but it is unlikely that these affected our aging study for the following reasons.

First, with the exception of transitional cell carcinoma, none of the other factors were skewed with respect to age, and would not be expected to bias gene expression in an age-related fashion. Second, the two types of tumors (renal cell carcinoma and transitional cell carcinoma) were localized to an isolated region of the kidney. Our normal samples were obtained from the region of the kidney furthest from the carcinoma, were not directly contaminated with cancer cells, and appeared normal histologically. This procedure for obtaining kidney samples has been used previously to profile gene expression in normal kidney and as a normal control in a kidney cancer study.

Third, we used regression models to directly test whether our aging studies were affected by seven medical factors: renal cell carcinoma, transitional cell carcinoma, size of tumor, hypertension, systolic blood pressure, diastolic blood pressure, and diabetes mellitus. For renal cell carcinoma, we used a regression model predicting expression from age, sex, tissue type, and a zero/one variable indicating whether the sample came from a patient with renal cell carcinoma or not. The result gave a p-value for whether renal cell carcinoma affected each of the 44,928 genes present on the Affymetrix DNA chip. The smallest p-value was 0.00013. We would expect to see almost six such p-values by chance alone. This result indicates that the presence of renal cell carcinoma does not significantly affect the expression of any gene in the normal tissue from the same kidney, compared to normal tissues taken from kidneys without renal cell carcinoma.

Next, we plotted the results using only the age-regulated genes, to investigate whether adjustments for renal cell carcinoma could affect their change in expression with respect to age. We used one regression model that included a renal cell carcinoma term and another model that did not have the term. We then selected genes that showed statistically significant (p<0.001) age regulation using either of these models. Renal cell carcinoma does not significantly affect the age slopes for these genes, indicating that this medical factor has little effect on age-related gene expression.

We repeated the regression analysis for six other factors that might confound our results (transitional cell carcinoma, size of tumor, hypertension, systolic blood pressure, diastolic blood pressure, and diabetes mellitus). The regression slopes changed very little with and without these factors, indicating that these factors do not strongly affect our analysis of age regulation.

Fourth, five of the samples were from kidneys that did not have tumors, and two of these were from donor kidneys used for transplantation that had no associated pathology at all. The expression profile from these five patients was similar to the profile from other samples used in our study. In summary, it is unlikely that these disease and medical factors have confounded our analysis of age-regulated changes in gene expression.

Changes in the expression for some of the 985 age-regulated genes may directly reflect the aging process in the kidney; these genes would serve both as aging markers and provide clues about molecular mechanisms for aging in the kidney. Other changes may result from an age-related change in the relative proportion of cell types within the kidney, such as would result from increased infiltration of immune cells with age. Finally, the expression changes may reflect the downstream response of the kidney to an age-related process elsewhere, such as would result from age-related changes in blood pressure or vascular supply.

Common Mechanisms of Aging in the Cortex and Medulla of the Kidney. Since the cortex and medulla contain different cell types and have distinct functions, it was of interest to test whether they age similarly. To test whether age-related gene expression changes are different in cortex and medulla, we considered a model in which a term of the form $\beta 4j \times Tissue \times Age$ was added to the model in equation 1. In such a model, the change in expression with age is linear within each tissue type, but the slope in the medulla is larger than that in the cortex by $\beta 4j$. Genes showing tissue-specific slopes would appear in peaks on the left and right. The figure shows neither of these peaks, indicating there is no statistically significant difference in aging between the two tissue types.

To further investigate coordinate aging in the cortex and medulla, we searched for age-regulated genes in each of these tissues independently, and then tested whether age-regulated genes in one were also age-regulated in the other. Specifically, to find age-regulated genes in the cortex, we fit the model $$Y_{ij}=\beta_{0j}^{C}+\beta_{1j}^{C}Age_i+\beta_{2j}^{C}Sex_i+\epsilon_{ij}^{C}, \quad (2)$$

using the cortex samples only. To find age-regulated genes in the medulla, we fit the model $$Y_{ij}=\beta_{0j}^{M}+\beta_{1j}^{M}Age_i+\beta_{2j}^{M}Sex_i+\epsilon_{ij}^{M}, \quad (3)$$

using only the medulla samples. We found 634 genes in the cortex samples and 72 genes in the medulla samples that showed significant changes in expression with age (p<0.001).

Having identified age-regulated genes in the cortex, we next examined whether they were also age-regulated in the medulla. If aging in the medulla were unrelated to aging in the cortex, we would expect to see a flat histogram. The actual histogram has a strong peak of genes on the right, indicating that significantly age-regulated genes in the cortex tend to also be significantly age-regulated in the medulla. Of the 634 genes that increased expression with age in the cortex, 22 also increased expression with age in the medulla, compared with the 0.6 genes expected at p=0.001. We obtained similar results when we took the converse approach, first selecting the 72 age-regulated genes in the medulla, and then testing whether they were also age-regulated in the cortex.

Next, we compared the slope of expression with respect to age in the cortex to that in the medulla (FIG. 2C). The results show a strong correlation between age coefficients in cortex and medulla. For the 684 genes age-regulated in at least one of the tissue types, the age coefficients had a correlation of r=0.487. Models 2 and 3 allow us to investigate whether the cortex and medulla age at the same rate as specified in model 1. For the 22 genes that are significantly age-related in both tissues, the age coefficients have a high correlation (r=0.96), and the slopes themselves are numerically close (FIG. 2D). We found a small mean absolute difference in slopes of 0.00185 (log2 expression per year), corresponding to only a 6% divergence in expression over 50 y. Given the strong similarities in the aging profiles of these two tissue types, we are able to increase the statistical power of our analysis by pooling the cortex and medulla datasets (resulting in model 1).

Increased Expression of Immune Genes in the Kidney in Old Age. We examined the list of 985 age-regulated genes, and immediately found evidence for increased expression of genes from immunocytes. Many of the 985 age-regulated genes are expressed specifically in B cells (e.g., immunoglobulin mu, kappa, and lambda), T cells (e.g., T cell receptor beta), or neutrophils (e.g., neutrophil cytosolic factors 1 and 4). Nearly all of these immune genes increase expression with age. These results suggest that there are increased numbers of immune cells in the kidney in old age, resulting in an age-related increase in abundance in all genes that are expressed specifically in these cells. Immune function is known to decline with age, and the increased numbers of immunocytes in the kidney might compensate for decreased function in individual immune cells, either for immune surveillance or for responding to low levels of inflammation occurring normally. In addition to increased cell numbers, the apparent increase in expression of the immune genes could also be due to increased expression within the immune cells themselves. Immunohistochemical experiments using antibodies directed against markers specific for B cells, T cells, or neutrophils showed that the kidney samples contained a small proportion of immune cells (less than 1%) in sporadic clusters scattered throughout each section.

If the number of immune cells increases with age in our kidney samples, then any gene showing an age-related increase in expression might do so because it is expressed in immune cells and not because it is age-regulated in the kidney. As immune cells comprise only a small fraction of the kidney sample, age-regulated genes that are expressed at higher levels in the kidney than the blood are likely to be expressed in kidney cells themselves. To compare gene expression levels between the blood and the kidney, we purified RNA from whole blood from five new individuals, prepared labeled cRNA, and then hybridized it to Affymetrix gene chips in the same manner as before. We computed the log2 of the expression level for each gene, and then calculated an average expression level for the blood (five samples) and the kidney (134 samples). Of the 985 genes that change expression with age, 538 are expressed at higher levels in blood cells than in the kidney samples. Age-related changes in the RNA abundance of these genes may reflect either changes in the fraction of immune cells in the kidney or age-related changes in expression in kidney cells. The remaining 447 are expressed at higher levels in the kidney than in whole blood, and age regulation of these genes is likely to reflect expression changes in kidney cells themselves. Of these 447 genes, 257 have increased expression levels in old age (age-induced) and 190 have decreased expression levels (age-repressed).

Majority of Age-Regulated Genes in the Kidney Are Expressed Broadly. To address whether different organs have distinct or common aging profiles, we analyzed whether the 447 age-regulated genes in the kidney were expressed specifically in the kidney or broadly in many tissues. If the kidney has its own specific pattern of aging, one might expect that the set of 447 aging-regulated genes would be enriched for those expressed specifically in the kidney, such as genes that have direct roles in forming the filtration barrier or in regulating ion or water reabsorption. If there is a common profile for aging shared among tissues, one might expect that most of the list of 447 aging-regulated genes would be expressed in many tissues.

Figure 5:
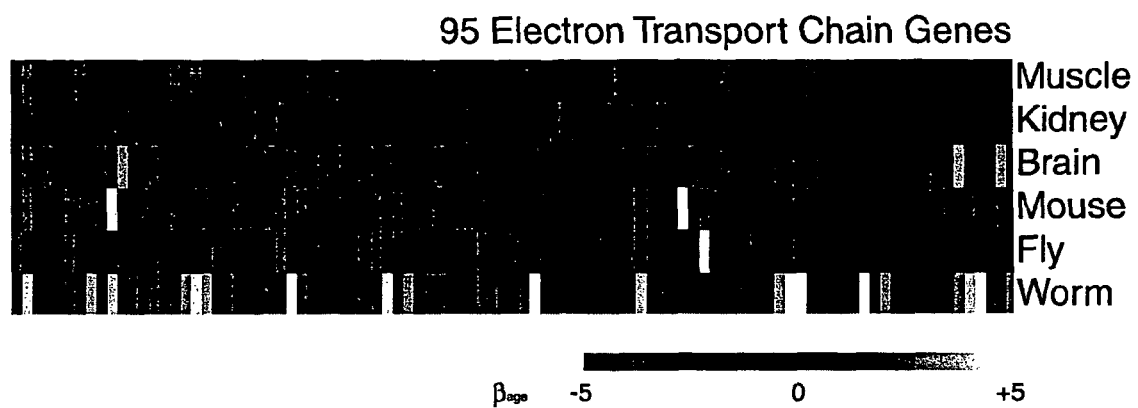
FIG. 5: The electron transport chain decreases expression with age in human and mouse. Rows represent either human tissues or model organisms. Columns correspond to individual human genes and homologs to human genes defined by reciprocal best BLAST hits in other species. Scale represents the normalized slope of the change in log2 expression level with age ($\beta 1j$). Data from different species were normalized by dividing the slope of expression with age by the standard deviation of all similar slopes in the data set. Grey indicates genes were not present in that species.

We determined the level of expression of the age-regulated genes in different tissues using data from a previous study reporting a genome-wide profile of gene expression in 26 different human tissues with Affymetrix gene arrays. Of the 447 aging-regulated kidney genes, 227 are represented in the previous work. Nearly all of these have general, rather than kidney-specific, expression patterns; specifically, we calculated the median expression level from all tissues and compared this to the average expression level from the kidney samples. We found that only seven of the 227 aging-regulated genes were enriched in the kidney more than 2-fold compared to the median level from all tissues (FIG. 5). The observation that nearly all of these 227 age-regulated genes are expressed in many tissues suggests that they act in common cellular pathways. Altered expression of these genes in old age may weaken these common functions, subsequently leading to physiological decline of kidney-specific functions.

Molecular Markers for Physiological Aging. The expression levels of these 447 age-regulated genes constitute a molecular profile of aging, and we can examine the expression profile of individual patients to observe how they compare to the average for their age group. Older individuals tended to express age-induced genes at higher levels and age-repressed genes at lower levels than younger individuals. However, certain individuals had unusual expression profiles, in which genes were expressed at levels more typical of a different age group. For example, patient 81 was 78 y old but had an expression profile as though she were older. Her kidney showed very high levels of age-induced genes and very low levels of age-repressed genes. Patient 95 was 81 y old, with an expression profile similar to patients 30 or 40 years younger.

Do the molecular gene expression profiles correlate with the physiological ages of the kidney samples? That is, does patient 81 have a kidney showing excessive age-related damage and does patient 95 have a kidney with unusually good health? To answer these questions, we determined the morphological and physiological states of the kidneys from each of the patients by examining histological stains. As people grow older, there is a general decline in the morphological appearance of the kidney: (1) the glomeruli lose their structure and their capillaries are replaced with fibrous tissue (glomerular sclerosis), (2) the tubules collapse and atrophy, and the interstitial space between them widens and scars (tubular atrophy/interstitial fibrosis), and (3) there is a thickening of the innermost layer of the arteriole wall due to the accumulation of hyaline material (arterial intimal hyalinosis). We gave three scores to each kidney section corresponding to the appearance of the glomeruli, the tubules, and the arterioles. Scores ranged from zero for normal appearance for youthful patients to four for an advanced state of glomerular sclerosis, tubular atrophy/interstitial fibrosis, or arterial intimal hyalinosis. We then added the glomerular, tubular, and arteriolar scores together to form a combined score ranging from zero (best) to 12 (worst), termed the chronicity index. The chronicity index is a quantitative estimate of the morphological appearance and physiological state of the kidney for each of the patients. As expected, the chronicity index shows a strong positive correlation with age showing that morphology and function tend to be worse for older subjects.

We then compared the chronicity index to the gene expression profiles of the 447 age-regulated genes as a function of age. In general, we found that the gene expression profiles correlated well with the chronicity index. Patients with expression profiles normally associated with people much older also had a high chronicity index; for example, the expression profile of patient 81 was similar to that of patients who were much older, and the chronicity index was also unusually high for the patient's age. Conversely, patients with expression profiles normally associated with younger people tended to have a low chronicity index for their age, such as patient 95. Although the 447 age-regulated genes were selected solely on the basis of their change with chronological age, these results indicate that their expression profiles are able to predict patients that have kidneys exhibiting unusual health or abnormal degeneration for their age. Thus, the 447 age-regulated genes can be used as molecular markers for physiological decline in the kidney during aging.

Age-Regulated Genes in the Kidney. Some of the 447 age-regulated genes may be involved in either causing or preventing aging in the kidney, whereas expression changes for others may be a consequence of age-related cellular changes. A candidate from our list that might promote age-related decline is mortalin-2 (which encodes Heat Shock Protein 70), which decreases expression in the kidney in old age. Heat shock proteins act as protein chaperones, and likely function to counteract cell senescence by alleviating the accumulation of damaged proteins in old cells. In human fibroblasts, overexpression of mortalin-2 extends lifespan in vitro. In the nematode *C. elegans*, overexpression of mortalin or HSP-16 (a related heat shock protein) extends longevity, and several genes encoding heat shock proteins decrease expression in old age. Reduced expression of mortalin-2 in old human kidneys could increase the accumulation of denatured proteins and thereby reduce general cellular function.

A gene from our list that might function to prevent aging is the gene encoding insulin-like growth factor receptor, which decreases expression in old age. Loss-of-function mutations in this gene result in extended longevity in worms, flies, and mice. This observation suggests that decreased expression of this gene during normal aging might help prolong the functional lifespan of human kidneys.

We examined the list of 447 age-regulated genes for functional groups showing a consistent change with age. One group includes genes involved in the formation of the extracellular matrix, which show a consistent increase in expression in old age. Seven age-regulated genes encode proteins known to play key roles in maintaining epithelial polarity (three types of claudins, two cadherins, occludin, and a cell adhesion molecule), all but one of which increase expression in old age. Forty-nine age-regulated genes encode protein components of the extracellular matrix, all but four of which increase expression in old age. In the kidney, the extracellular matrix could play a key role in governing the filtration of blood via the basement membrane, a capacity that declines with age. The observation that genes involved in forming the extracellular matrix increase expression in the kidney with age may be directly relevant to the age-related decline in glomerular filtration rate.

Another functional group is a set of 11 genes encoding ribosomal proteins, all of which increase expression with age. Protein synthesis rates are known to decline as animals grow older, and increased expression of these ribosomal protein genes may serve to offset this.

Changes in the expression of regulatory genes with age may have particularly strong effects on kidney metabolism and function, since these changes are likely to initiate cascades of changes in downstream genes. We examined our list of 447 age-regulated genes for those that are likely to function as regulatory genes. Of the 447 age-regulated genes, 15 encode transcription factors and 51 encode proteins that are part of signaling pathways.

Age-Regulated Genes Enriched in the Glomeruli. As filtration of the blood takes place in the glomerulus, age-regulated genes that are enriched in the glomerulus may be especially important for understanding how kidney function declines with age. We identified genes enriched in the glomerulus using data from a previous study, in which cDNA microarrays were used to compare expression levels in the glomeruli relative to the rest of the kidney. Of the 447 genes identified in our study, 213 were represented on the cDNA microarrays in the previous experiment, and 19 were enriched greater than 2-fold in the glomeruli relative to total kidney. These included four genes that encode proteins involved in the formation of the extracellular membrane (a type 5 collagen, alpha-2 macroglobulin, and two tissue inhibitors of met-alloproteinase), all of which increase expression with age.

Old age is associated with a functional decline in a myriad of molecular and cellular processes. To gain a global perspective of the diverse pathways that change with age, we performed a whole-genome analysis of gene expression as a function of age for kidney samples from 74 patients ranging in age from 27 to 92 y. Many factors affect gene expression in addition to age, including variability between individuals, between different tissues within the kidney, and between sexes. The large number of samples in our dataset provided good power for identifying age-regulated genes in noisy data despite small changes in expression, and allowed us to use a statistical linear regression model to identify 985 genes that change expression with age.

The results from this work show that transcriptional differences between young and old individuals involve an accumulation of small changes in expression from many genes, rather than resulting from large expression changes in a small number of genes. This observation suggests that functional decline in old age is not the result of the complete failure of a small number of cellular processes. Rather, it is the slight weakening of many pathways that cumulatively causes a significant decrease in cell function. Studying aging by analyzing one pathway at a time is difficult, because any single pathway might show only a small change with respect to age and might contribute only a small amount to the overall functional decline in old age. By contrast, functional genomics is a powerful approach to study aging, because many genes can be simultaneously scanned in parallel for small changes in expression.

Although the cortex and medulla are comprised of different types of cells and perform different physiological functions, our results suggest.that they share a common mechanism for aging. We plotted the expression levels of the 985 aging-regulated genes found in this work against a dataset of aging in muscle, and found that these genes did not show much age regulation in muscle. Specifically, the Pearson correlation (r) of the regression slopes for these 985 genes was only 0.085 between the kidney and muscle aging experiments and hence accounts for only 0.0072 of the variance between these two tissues.

Aging has been best studied in model organisms, and it is thus of great interest to discern whether aging in these species is similar to the aging process in humans. Previous studies have reported gene expression changes associated with old age for worms, flies, and several tissues from mice. We found no correlation between age regulation in human kidney and age regulation in either worms or flies.

Many of the age-regulated genes in the kidney may change in response to declining kidney function. Functional decline of the kidney with age varies between individuals, and these genes could be used as diagnostic markers to evaluate levels of kidney function in older patients. This could provide invaluable information in understanding the clinical course of kidney aging and the suitability of using older kidneys in organ transplants. Other genes may be directly regulated by aging per se, and these genes could pinpoint mechanisms that play key roles in the aging process itself.

Materials and Methods

Samples. Normal kidney samples were obtained either from biopsies of donor kidneys for transplantation or from nephrectromy patients (with informed consent) in which the pathology was localized and did not involve the part of the kidney sampled. Key factors include sex, race, age, blood pressure, pathology, medications, serum creatinine, and urinary protein concentrations. Kidney tissue was harvested meticulously with the intention of gathering normal tissue uninvolved in the tumor. Tissue was taken from a point as far away from the tumor as possible. Any samples that showed evidence of pathological involvement or in which there was only tissue in close proximity to the tumor were discarded. Kidney sections were immediately frozen on dry ice and stored at −80° C. until use. The same harvesting sources and techniques have been used previously to profile expression in normal kidney and to provide normal controls in a study on kidney cancer.

Histology. Frozen tissues were placed in cryomolds, embedded in Cryo Tissue Tek O.C.T. Compound (Sakura Finetek, Torrance, Calif., United States) and cut into 4-µm sections (Leica Microsystems, Wetzlar, Germany). Sections were stained with hematoxylin and eosin, and then histologically evaluated to exclude samples showing abnormal histology. Histology slides were also marked into two main functional sections, the cortex and medulla, to help aid in accurate dissection of these two areas. We reviewed radiological findings for all tumors and histology for all slides. We excluded any cases in which radiological imaging, gross examination at the time of resection, or histological review of the removed tissue indicated that there might be tumor involvement of the normal areas. Cases with incomplete or unclear medical records were excluded from this study.

RNA isolation. Frozen kidney tissue samples were dissected into cortex and medulla sections. Portions were weighed (0.05-0.75 g), cut into small pieces on dry ice, and then placed in 1 ml of TRIZOL™ chemical reagents (Invitrogen, Carlsbad, Calif., United States) per 50-100 mg of tissue. The tissue was homogenized using a POWERGEN 700™ homogenizer (Fisher Scientific, Pittsburgh, Pa., United States), and the total RNA was isolated according to the TRIZOL™ chemical reagents protocol.

High-density oligonucleotide arrays. A standard protocol designed by Affymetrix (Santa Clara, Calif., United States) for their HG-U133A and HG-U133B high-density oligonucleotide arrays was slightly modified by the Stanford Genome Technology Center (Stanford, Calif., United States), and all samples were processed in their facility. Eight micrograms of total RNA was used to synthesize cRNA for each sample, and 15 µg of cRNA was hybridized to each DNA chip. The samples were done in random order with respect to tissue type and age.

Microarray data normalization and analysis. Using the dChip program, microarray data (.cel files) were normalized according to the stable invariant set, and gene expression values were calculated using a perfect match model. All arrays passed the quality controls set by dChip. All of the Affymetrix data are available at the Stanford Microarray Database. The accession numbers for all genes on the Affymetrix arrays can be obtained from the Stanford Microarray Database.

Regression models and p-values. The p-values we use are based on t-tests from standard linear regression theory. Under the hypothesis H0 that $\beta kj=0$, the estimated coefficient $\hat{\beta} kj$ is a random variable. The least squares value is a particular number, $\hat{\beta} LSkj$. The p-value measures the extent to which the least squares value is surprisingly large assuming H0 holds. Specifically, the two-tailed p-value is $$p_{kj}=Pr(|\hat{\beta}_{kj}|\geq|\hat{\beta}_{kj}^{LS}|;H_0),\quad(4)$$

and the one-tailed p-value we use is $$\tilde{p}_{kj}=Pr(\hat{\beta}_{kj}\geq\hat{\beta}_{kj}^{LS};H_0).\quad(5)$$

Sometimes $\tilde{P}kj$ is employed to test H0 against an alternative hypothesis of $\beta kj<0$. We use it because it distinguishes between significant increasing and significant decreasing coefficients. Under H0, the distribution of p is U(0,1), and so is that of $\tilde{P}$. Numerically, the equation holds.

$$p=2\min(\tilde{p},1-\tilde{p})\quad(6)$$

The t-test is derived under an assumption of normally distributed errors. The data showed estimated errors with heavier than normal tails. The t-test is known to be robust against heavy-tailed errors.

A linear regression is more appropriate for these data than is an analysis of variance (ANOVA) on age groups, because the latter is aimed at piecewise constant expression patterns, and it is not plausible that expression should change sharply at a given age. A genome-wide ANOVA (data not shown) did, however, find a similar group of age-related genes. Unlike ANOVA, regression summarizes the age effect in one coefficient. This is advantageous for interpretation and for statistical power when there is little nonlinearity.

The decision of whether to include a variable in model 1 was based on the collection of p-values for all the genes. If the histogram of $\tilde{P}$ values differed sharply from uniform, and if the smallest p-values were small compared to 1/44,928, then the coefficient was included.

Gene lists were made using a threshold p-value of 0.001. Such a gene list can be expected to have about 44 genes in it by chance, even if all of the coefficients are really zero. Thus, of the 985 age-related genes, it is plausible that about 44 of them are false positives. We have chosen to work with a fixed significance level, instead of attempting to fix the false discovery rate, because our test statistics are strongly correlated.

We were concerned that intra-subject correlations might have affected our results. For each of 59 subjects with both cortex and medulla samples, we subtracted log2 expression in the cortex from that in the medulla, and fit a regression of the difference versus age and sex. Such an analysis removes intra-subject correlations. There was again no evidence of genes aging differently in the two tissue types.

Example 2

Results:
A Global Gene Expression Profile for Aging in Human Muscle

In order to study the effects of aging in human muscle, we obtained 81 samples of human skeletal muscle from individuals spanning 16 to 89 years of age (Table 2). 63 samples were obtained from the abdomen, 5 were from the arm, 2 were from the deltoid muscle, 2 were from the inner thigh, and 9 were from the quadriceps (Table 3). We used AFFYMETRIX™ DNA arrays to generate a transcriptional profile of aging in human muscle. We isolated total RNA from each muscle sample, and synthesized biotinylated cRNA from total RNA. We then hybridized the cRNA to AFFYMETRIX™ 133 2.0 Plus oligonucleotide arrays, representing nearly the entire human genome (54,675 individual probe sets corresponding to 31,948 individual human genes). We plotted the expression of each gene as a function of age, resulting in a dataset that shows the expression of nearly every gene in the genome as a function of age in human muscle.

We used a multiple regression technique on each gene to determine how its expression changes with age, as had been done for age regulation in the kidney (Example 2). We analyzed age regulation in skeletal muscle in two ways. In the first way, we used a stringent statistical cutoff to select genes showing age regulation. In the second way, we used a more sensitive screen to find evidence of consistent but subtle age regulation of entire genetic pathways.

To identify individual genes showing strong age regulation, we examined the slope with respect to age ($\beta 1j$) for each gene, and identified 250 genes in which the slope was significantly positive or negative (p-value <0.001)(FIG 1). We expect about 32 genes to be found by chance at this selection stringency, suggesting a false discovery rate of less than 13 percent. Of these age-regulated genes, 125 genes increase expression and 125 genes decrease expression with age.

We considered the possibility that some of the 250 genes might not be age-regulated per se, but rather might appear to be age-regulated because they are associated with a pathological condition that increases with age. For example, the incidence of diabetes is known to increase with age in the general human population. Our selection of patients might show a bias of diabetes in the elderly, in which case genes that change expression in response to diabetes might appear to be age regulated in our study. In addition to diabetes, we considered thirteen other factors that might also confound our study on aging, such as whether the patient was male or female, the anatomical origin of the muscle sample, the type of pathology associated with the patient, and types of medication taken by the patient (Table 3). With the exception of hypothyroidism, none of the medical factors showed a strong bias for age, and so it is unlikely that these confounding factors would cause genes to appear to be age-regulated. Hypothyroidism was absent in the young and present in about half of the elderly.

We tested each factor to determine whether it affected the slope of gene expression with respect to age of the 250 age-regulated genes. We used a multiple regression model that included a fourth term representing the medical factor (such as hypothyroidism) in addition to age, sex and anatomy. We then compared the aging coefficient using this new model with the one from the original model that did not include the term. If any of the 250 genes were to be regulated by the medical factor and not by age per se, we would expect marked differences in the aging coefficients ($\beta 1j$) generated by the two multiple regression models. None of the fourteen medical factors, including hypothyroidism, had a significant effect on age-regulation (FIG. S2). Thus, we found no evidence that any of these medical factors confound the results of our aging study.

In summary, we have generated a global profile of changes in gene expression during aging in human muscle (FIG. 1). It is well established that aging has many effects on muscle, such as decrease in physiological performance, changes in morphology and increased susceptibility to disease. The data from FIG. 1 extend our understanding of muscle aging to the level of specific genes and genetic pathways, providing insight into possible mechanisms underlying overall decline of muscle function in old age. Overall, the difference in gene expression between young and old muscle tissue is relatively small. Specifically, only 250 genes show significant changes in expression with age ($p<0.001$), and the large majority of these age-regulated genes change expression less than twofold over 50 years. These results are consistent with an aging process in which age-related decline in cellular functions is caused by the accumulation of multiple, minute changes in the regulation of genes and pathways.

For many of the 250 genes shown in FIG. 1, the observation that their expression is age-regulated suggests specific mechanisms that might contribute to age-related decline in muscle physiology. For example, CYP26B1 shows an average increase in expression of 90% over 50 years. CYP26B1 is a member of the cytochrome P450 family, which are monooxygenases used to metabolize toxic substances. Increased expression of CYP26B1 in old age could help eliminate toxins that accumulate with age.

LASS5 decreases expression about 25% in 50 years. LASS5 is the human ortholog of the yeast lag1 longevity assurance gene. In yeast, lag1 shows decreased expression in older yeast cells similar to our results showing decreased expression in old age in human muscle. LASS5 is involved in the ceramide signaling pathway, which plays important roles on several lifespan-associated processes, such as stress resistance and apoptosis. Reduced expression of LASS5 in old age could impair cell function by reducing ceramide signaling.

In addition to searching for age-regulation one gene at a time, we also screened known genetic pathways for those showing an overall change with age. Screening for coordinated age regulation of genetic pathways increases the sensitivity of our analysis, as the combined effects of small regulation of many genes in a pathway can be a significant. For example, in a previous study of type-2 diabetes, screening genetic pathways for changes in expression provided key insights that were not possible from analyzing genes individually.

We used Gene Set Enrichment Analysis (GSEA) to determine whether a genetic pathway shows evidence for age regulation. We assayed 949 gene sets defined by the Gene Ontology consortium. We modified the original GSEA paradigm because it was intended for data sets with two categories of sample, and we are instead fitting regression models to continuously varying independent and dependent variables. Accordingly, we have both replaced the two sample test statistic in GSEA with an estimated regression slope for age and replaced the Kolmogorov-Smirnof statistic with a Van der Waerden statistic. Using these parameters also let us adjust for other variables, such as the sex or tissue type in each data set.

Figure 2:
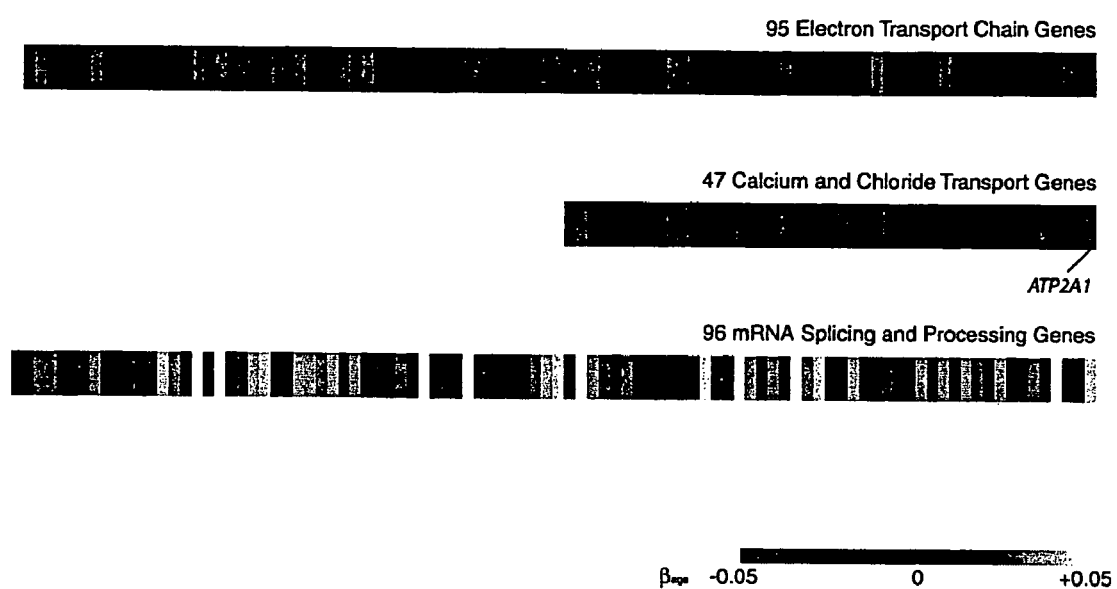
FIG. 2: Three gene sets are regulated with age in muscle. Rows represent the mRNA splicing and processing, the electron transport chain and the calcium/chloride ion transporter gene sets. Columns correspond to individual genes within a given gene set. Scale represents the slope of the change in log2 expression level with age ($\beta 1j$).

The GSEA algorithm searches for sets of genes in which the members show significant bias in age-regulation; e.g. the gene set shows either a coordinated increase or a coordinated decrease in expression in old age. Using a threshold of $p<1\times 10^{-6}$, we found that genes involved in either the electron transport chain or the calcium/chloride ion transport show an overall decrease in expression with age and that mRNA splicing showed an overall increase in expression with age (FIG. 2, Table 2). We would not expect to find any gene sets to show age regulation by chance given our stringent cutoff (949 gene sets; $p<1\times 10^{-6}$). We confirmed age-regulation of pathways nominated by GSEA by bootstrapping the dataset 1000 times and found in each of the three cases that one-sided p-values of the bootstrap were less than a threshold of 0.05 (Table 2).

The mitochondrial electron transport chain was found to show an overall decrease in expression with age (FIG. 2A). This group contains 95 genes, including genes associated with the NADH dehydrogenase family (complex I), succinate-coenzyme Q reductase (complex II), ubiquinone-cytochrome c reductase (complex III), cytochrome c oxidase (complex IV), H+-ATP synthase (complex V), and the uncoupling proteins. Of the 95 genes, 76 decrease expression and 19 increase expression with age. The finding that expression of genes involved in the electron transport chain decreases in old age supports the mitochondrial free radical theory of aging, as free radical generation by mitochondria would preferentially damage mitochondrial protein complexes such as the electron transport chain. Decreased expression of the electron transport genes (encoded in the nucleus) might be caused by feedback regulation from damage to the electron transport chain protein complex. Furthermore, other protein complexes in the mitochondria (such as mitochondrial ribosomal genes) do not decrease expression with age. Thus, aging does not have a general affect on genes encoding mitochondrial components, but rather specifically affects expression of genes that are part of the electron transport chain.

Calcium and chloride ion transport genes show an average decrease in expression with age. This gene set is composed of 47 genes, including calcium-ion ATP synthases, calcium ion channels, and chloride ion channels (FIG. 2B). ATP2A1, which encodes Ca2+-ATPase 1, shows the largest decrease in expression with age (22% over 50 years). Calcium and chloride ions play key roles in muscle contraction, and decreased expression of Ca2+/Cl- ion transport genes could play a role in limiting muscle performance in old age.

Genes involved in mRNA splicing and processing showed an overall increase in expression with age. This gene set is composed of a total of 96 genes, 84 of which increase expression and 12 of which decrease expression with age (FIG. 2C). This result suggests that mRNA splicing patterns might be altered in muscle tissue in old age.

Biomarkers of Physiological Aging

Figure 3:
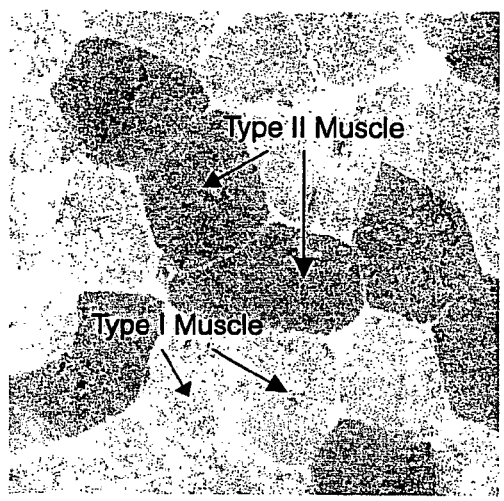
FIGS. 3A-3D: Gene expression predicts physiology of aging. A: Cross section of histologically unremarkable deltoid muscle from a 48 year old woman demonstrating relatively equivalent sizes of Types I and II muscle fibers. Arrows denote fibers types as distinguished by enzyme histochemistry. (Cryosection, 200×, myosin ATPase at pH 9.4). B: Cross section of deltoid muscle from an 88 year old woman demonstrating selective atrophy of Type II muscle fibers that stain darkly by ATPase enzyme histochemistry. (Cryosection, 200×, myosin ATPase at pH 9.4) C: Histogram showing the correlation between muscle physiology and gene expression for each of the 250 age-regulated genes. For each of the 250 age-regulated genes, we calculated the partial correlation coefficients between the TypeII/TypeI muscle fiber diameter ratio and gene expression excluding age variation (x-axis). The squared partial correlation coefficient denotes the amount that changes in gene expression account for variance in TypeII/TypeI muscle fiber diameter ratios while excluding the effects of age. D: Histogram showing the likelihood of finding 92 genes with |r|>0.2 from a set of random genes. We performed a Monte Carlo experiment by randomly selecting sets of 250 genes from the genome, and calculating how many genes in the set had |r|>0.2 as in part C. The procedure was repeated 1000 times and the histogram shows the number of genes from each random selection that have |r|>0.2. The arrow shows the number of genes exceeding this threshold (92) from the set of 250 age-regulated genes (p<0.001).
Figure 3:
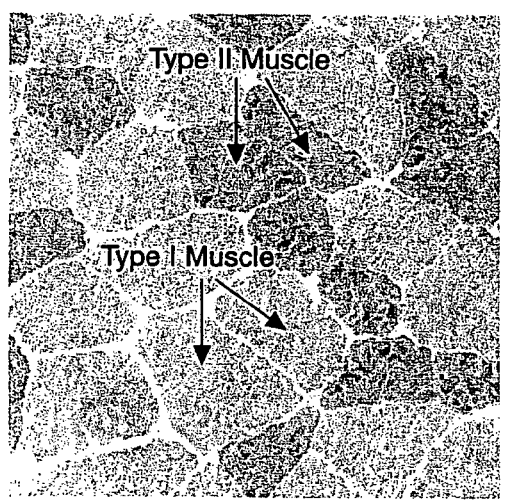
Figure 3:
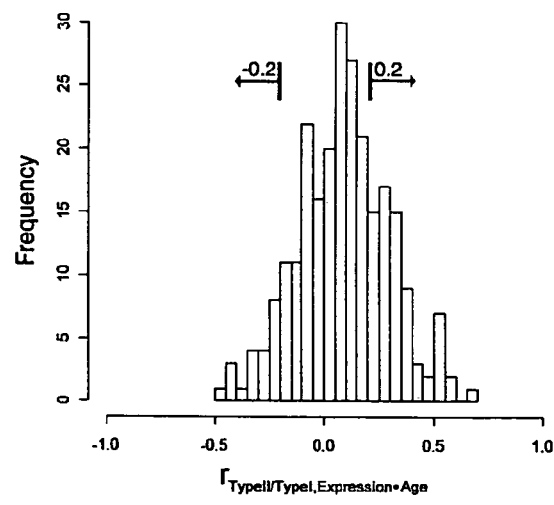
Figure 3:
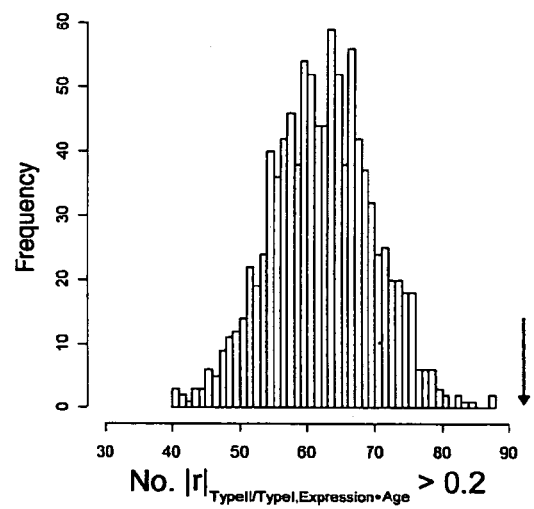

Some people age slowly and remain strong and fit in their 70s whereas others age rapidly, become frail and susceptible to age-related disease. We wanted to determine whether the expression profile for the 250 aging regulated genes could predict physiological, as well as chronological, aging. For example, patient V17 is 41 years old but expresses his age-regulated genes similar to patients that are 10 to 20 years older, and we would like to determine whether this patient had poor muscle physiology for his age (FIG. 1). Conversely, patient M73 is 64 years old but has a molecular profile similar to other patients that are 30 years younger, and we wanted to determine whether this patient has relatively good muscle physiology for his age. We prepared histological sections for all 81 skeletal muscle samples, and were able to reliably measure the diameters of the Type I and Type II muscle fibers for 32 samples (FIGS. 3A, 3B).

We wanted to determine whether the expression profile for some or all of the 250 age-regulated genes could predict Type II/Type I muscle fiber diameter ratio independently of age. To do this, we calculated the partial correlation coefficients for the influence of each gene on Type II/Type I diameter ratio excluding the effect that age has on variation (FIG. 3C). Genes that can predict physiological age of muscle will show a correlation with Type II/Type I diameter in the absence of the effect of age. Of the 250 age-regulated genes, 92 are biomarkers of physiological muscle aging as their partial correlation coefficients are greater than 0.2. As a control, we randomly chose 250 genes from the genome 1000 times, determined the number that had correlation coefficients greater than 0.2, and found that none of the random sets had 92 genes. This result indicates that the observed correlation between the DNA chip expression profile and physiological muscle aging is significant to $p<0.001$ (FIG. 3D).

The correlation between gene expression profile and physiological age can be seen in patients V17 and M73 in FIG. 1. Although patient V17 is relatively young (41 years old), the gene expression profile for the 250 age-regulated genes is most similar to older individuals and the Type II/Type I muscle fiber diameter ratio is low for his age. Conversely, although patient M73 is relatively old (64 years old), the gene expression pattern is similar to younger individuals and the Type II/Type I muscle fiber diameter ratio is high for his age (FIG. 1).

A Common Signature for Aging in Muscle, Kidney and Brain

Some aspects of aging affect only specific tissues; examples include progressive weakness of muscle, declining synaptic function in the brain, or decreased filtration rate in the kidney. Other aspects of aging occur in all cells regardless of their tissue type, such as the accumulation of oxidative damage from the mitochondria, DNA damage, and protein damage. Our genome-wide search for gene expression changes during aging includes both types of expression changes. It is of interest to discern which expression changes are muscle-specific and which are common to all tissues. Expression profiles that are common to aging in all tissues would provide insight into the core mechanisms that underlie cellular aging. Therefore, we compared the DNA chip expression data from the studies on muscle aging to DNA chip expression studies on aging in the brain and kidney.

Figure 4:
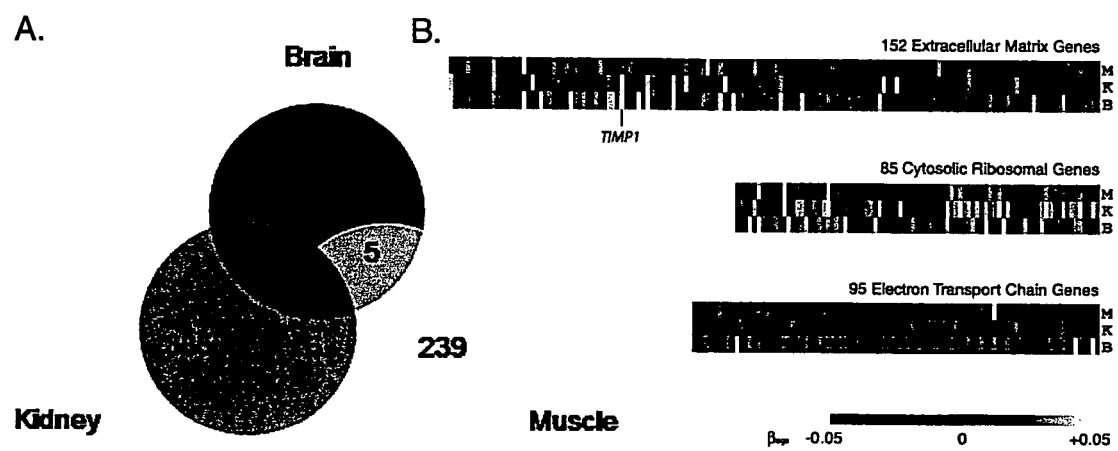
FIGS. 4A-4B: A common signature for aging in muscle, kidney, and brain. A: Venn diagram of overlaps between sets of aging-regulated genes. Muscle (250 aging-regulated genes), kidney (404 genes), and brain (386 genes). Significance for overlaps was calculated using the hypergeometric distribution. Muscle/kidney overlap: p<0.09. Muscle/brain overlap: p<0.07. Kidney/brain overlap: p<0.29. B: Shown are expression data from sets of extracellular matrix genes, ribosomal genes and electron transport chain genes. Rows are human tissues. (M, muscle; K, kidney; B, brain.) Columns correspond to individual genes in each gene set. Scale represents the slope of the change in log2 expression level with age ($\beta 1j$). Grey indicates genes were not present in the data set.

We used three methods to compare aging in the muscle to the brain and kidney. The most direct method was to separately select aging-regulated genes in each tissue using a high statistical cutoff, and then to compare the overlap in the aging-regulated gene sets. Previous studies had identified 404 unique aging-regulated genes in the kidney, and 346 unique aging-regulated genes in the brain. We did a pairwise comparison between each tissue to find genes that are aging-regulated in both sets (FIG. 4A). There are 6 aging-regulated genes in both the muscle and kidney ($p<0.09$, hypergeometric distribution), 5 aging-regulated genes in both the muscle and brain ($p<0.07$), and 13 aging-regulated genes in common between kidney and brain ($p<0.29$). There were no genes that were strongly age-regulated in all three data sets.

A second way to compare aging in different tissues is to calculate the correlation between age-regulation in two tissues. This approach is more sensitive than the first as a gene may be age-regulated in a second tissue but at a level below the stringent cutoff used to select aging-regulated genes. We combined the genes that are aging-regulated in either of two tissues, plotted their change in expression with respect to age in both tissues in a scatter plot, and calculated the Pearson correlation (r) for age regulation between the two tissues (Table 3). We found the strongest overlap in aging between the kidney and the brain ($r=0.219$), and smaller but positive overlaps in aging between the muscle and the kidney ($r=0.103$) or the muscle and the brain ($r=0.078$).

We tested the significance of these positive correlations in two ways. We first tested the likelihood of observing this level of correlation from a random list of genes. We generated 1000 sets of randomly-chosen genes and calculated the Pearson correlations of each set, and found that the correlations from the age-regulated genes were almost always higher than the correlations from the randomly chosen genes. This result indicates that the correlation in aging between tissues is significant for the muscle/kidney and kidney/brain pairings (Table 3). Next, we tested the possibility that the correlations were driven by aberrant readings from a few individuals in our experiments. We tested this by resampling the microarray data with replacement (so that data from certain samples would be lost and replaced by data from another sample), and then calculating the correlation in aging between two tissues in the resampled set. If the correlation is driven by a few outlying individuals in each expression experiment, then the positive correlation would not occur when these samples are absent from the resampled set. We observed that the resampled datasets gave positive correlations in all three pairings, and always gave positive correlations in the kidney/brain pairing (Table 3).

A third way to compare aging in different tissues is to evaluate the behavior of genetic pathways in the two different tissues. This approach is more sensitive than the previous approaches as significant results can be obtained from the accumulation of small changes in many genes in a pathway. Furthermore, the specific biological processes associated with each genetic pathway provide insights into mechanisms of aging. We used the modified Gene Set Enrichment Analysis described above to analyze data on age-regulation in the kidney and brain. We then searched for gene sets that showed significant age regulation in all three tissues. Specifically, we selected those gene sets that had a p-value less than 0.001 in each individual tissue and that also had a combined p-value of less than $1\times10^{-20}$. From a total of 949 sets of genes, we found that extracellular matrix genes and cytosolic ribosomal genes significantly increase expression with age in all three human tissues, and electron transport genes significantly decrease expression with age (Table 1). For each genetic pathway nominated by GSEA, we confirmed common age-regulation in these gene sets by bootstrapping each contributing dataset 1000 times and recalculating enrichment scores. In order to be confirmed by bootstrap as significantly age-regulated, each contributing tissue must reject the null hypothesis to a threshold of $p<0.05$, with a total multipled p-value of less than $10^{-5}$. Both the extracellular matrix and electron transport chain pathways met this threshold, while the cytosolic ribosomal pathway was very near the threshold (brain $p<0.06$) (Table 1).

The extracellular matrix gene set includes a total of 152 genes, and these genes show an overall increase in expression with age (combined p value$<1\times10^{-20}$; FIG. 4B). TIMP1, which encodes tissue inhibitor of metalloproteinase 1, shows the largest increase in expression with age (average 236% over 50 years). Increased expression of extracellular matrix genes with advancing age may contribute to widespread fibrosis in the elderly. Fibrosis is a process by which fibrous connective tissue proliferates throughout organs and impairs function of many tissues.

Cytosolic ribosomal genes include 85 genes that show a general increase in expression with age in all three tissues (combined p value<$1\times10^{-35}$). Specifically, 64 out of 85 cytosolic ribosomal genes increase expression with age in muscle, 80 out of 85 genes increase expression with age in the kidney, and 51 out of 67 genes increase expression with age in brain (FIG. 4B). This result is interesting because the rate of protein synthesis is known to decrease in old age, and yet our expression results show an increase in the expression of ribosomal genes. One possibility is that decreased protein synthesis in old cells induces expression of ribosomal genes, as part of a homeostatic feedback loop to partially compensate for loss of translational efficiency.

Electron transport chain genes show an overall decrease in expression with age (combined p value<$1\times10^{-35}$; FIG. 4B). Changes in expression with age of the electron transport genes in the kidney are generally greater than those seen in either muscle or brain. As discussed above, decreased expression of the electron transport chain is not a general phenomenon due to decreased mitochondrial copy number, as other mitochondrial components are not age regulated.

We wanted to determine whether there was a similar pattern of age-regulation for these three biological processes in different tissues. For instance, we wanted to determine whether the most highly age-regulated gene in one tissue was also highly age-regulated in other tissues. To test this model, we calculated the Spearman coefficient for each of the gene sets between pairs of tissues. For the extracellular matrix pathway, we found that the rank correlation of age-regulation between muscle and kidney was $r=0.25$ ($p<0.002$). For the electron transport chain pathway, we found that the correlation of age-regulation between kidney and brain was $r=0.26$ ($p<0.01$). These results suggest that there is significant similarity regarding which members of these two pathways exhibit the most age-regulation in these two pairs of tissues.

In summary, all three methods showed that there is a common core set of genes that show similar age-regulation across different tissues. In contrast, other genetic pathways (such as mRNA splicing genes and the calcium/chloride ion transporter genes) are age-regulated specifically in muscle.

A Public Age-Regulated Pathway in Humans and Mice

Having identified genetic pathways that are commonly age-regulated in different human tissues, we next determined whether their age-regulation is specific for humans (private) or whether these groups are also age regulated in other species (public). Genetic pathways that are age-regulated in different species would be of particular interest because they would identify mechanisms that are inextricably related to aging, even in animals that have vastly different lifespans.

We compared age regulation in humans to age regulation in the kidney of the mouse, *Drosophila melanogaster* and *Caenorhabditis elegans*. We first identified orthologs of human genes in each of the other species. Next, we determined the change in expression with respect to age for each gene in each species, using multiple regression techniques similar to the ones used for our studies on aging in human muscle.

We took the three gene sets shown to be aging-regulated in diverse human tissues, and then asked whether they also showed age-regulation in any of the other three species. We analyzed the expression of each of the three gene sets using modified Gene Set Enrichment Analysis to determine whether they showed an overall bias in expression with age in each species. The cytosolic ribosome pathway did not show age-regulation in the other species, and the extracellular matrix pathway did not have sufficient data in other species to make any conclusion.

The electron transport chain genes showed a consistent decrease in expression with age in humans ($p<10^{-12}$) and mice ($p<10^{-4}$). Expression of the genes in this pathway also consistently decreased with age in *Drosophila* ($p<10^{-12}$), but increased with age in C. elegans ($p<10^{-3}$) (FIG. 5). We again confirmed the age-regulation of this pathway by bootstrapping each contributing dataset and calculating a p-value of the bootstrap. Human, mouse and fly datasets exceeded the threshold of $p<0.05$, whereas worm exhibited a bootstrap p-value of 0.27. We can therefore confirm age-regulation of the electron transport chain in three species, but reject age-regulation of the electron transport chain in the worm. It is unclear whether the electron transport chain is actually unregulated in the worm. Potentially, lack of statistical power in the worm dataset could cause the pathway to appear unregulated with age. Thus, decreased expression of the electron transport chain during aging is similar between mammals, but not for invertebrates.

People age at different rates, especially with regard to muscular aging. Some remain fit and strong whereas other become frail and weak when they are old. The transcriptional profile for aging in this study revealed not only the chronological age, but also the physiological age, of the subjects. Specifically, a number of the age-regulated genes found in this study correlated not only with the chronological, but also with the physiological, age of the muscle sample (as measured by the diameter of the Type I and Type II muscle fibers).

Our results provide the first evidence for a common signature of changes of gene expression in different human tissues. Specifically, we found similar patterns of age regulation for three biological pathways in the muscle, kidney and brain. The increase in expression of the extracellular matrix pathway may be involved in widespread fibrosis seen in all aging tissues. The increase in expression of the cytosolic ribosomal pathway may be compensation for impaired translational capacity in aged cells. Finally, the electron transport chain may decrease expression as regulatory feedback to either oxidative damage inflicted on the electron transport chain or to decreased cellular metabolism.

We also found that nearly all age-regulation is specific to humans, and does not seem to occur in old mice, flies or worms. Thus, much of age-regulation in humans is species-specific (private) rather than universal for all animals (public). This result emphasizes the importance of studying aging in humans rather than model organisms with short life spans in order to understand how people grow old.

Nevertheless, we did find one pathway that was age-regulated in both humans and mice. The electron transport chain gene pathway decreases expression with age in both mammals. However, this pathway does not show similar age-regulation in all species as it decreases expression in flies, but increases expression in worms. Our results showed that expression of the electron transport chain decreases expression (rather than increases) in the muscle, kidney and brain of elder people. It is interesting that the electron transport chain is an ancient pathway with nearly identical sets of proteins in all eukaryotes, and yet it shows very different rates of age-regulation in humans and mice that precisely matches the 20-30 fold differences in their life spans. This suggests that decreased expression of the electron transport chain pathway with age may particularly informative as a biomarker of physiological aging in mammals.

Materials and Methods

Sample collection. The muscle samples were obtained from patient biopsies collected either during surgery or in an outpatient procedure. For example, the abdominal muscle samples were harvested during surgeries to treat gastrointestinal pathologies. There was no known pathology associated with these abdominal muscle samples themselves, except that they were obtained from patients with various gastrointestinal disorders. In the case of patients with gastrointestinal cancer, the abdominal muscle samples were harvested from regions of the abdomen that were not affected by the cancer. Each muscle sample was immediately frozen in liquid nitrogen and subsequently stored at −80° C. Finally, we checked each sample by histological staining, and excluded any samples that appeared abnormal or diseased.

RNA isolation. Frozen muscle samples were weighed (50 mg-100 mg), cut into small pieces on dry ice, and then placed in 1 ml of TRIZOL™ chemical reagents (Invitrogen, Carlsbad, Calif., United States). The tissue was homogenized using a POWERGEN 700™ homogenizer (Fisher Scientific, Pittsburgh, Pa., United States), and the total RNA was isolated according to the TRIZOL™ chemical reagents protocol.

DNA gene chip hybridization. A standard protocol designed by Affymetrix (Santa Clara, Calif., United States) for their HG-U133 2.0 Plus high-density oligonucleotide arrays was slightly modified by the Stanford Genome Technology Center (Stanford, Calif., United States), and all samples were processed in their facility. Eight micrograms of total RNA was used to synthesize cRNA for each sample, and 15 μg of cRNA was hybridized to each DNA chip. The samples were done in random order with respect to age.

Microarray data normalization and analysis. We used the DChip program to normalize the data and to generate expression levels for each individual probe set by a perfect-match only model. When different probe sets corresponded to the same gene, we averaged the expression levels together.

Muscle Fiber Diameter Measurement. Cross sections of muscle cryosections were photographed at 200× and the pictures were either measured digitally (diagnostic muscle biopsy samples, ATPase preparations) or printed (abdominal muscle samples, combined SDH-cytochrome c oxidase preparations) and measured by hand. All of the diagnostic muscle biopsies were measured and 32 of the 81 abdominal muscle samples were suitable for measurement, the remainder being inadequately oriented for cross sections or too small for meaningful data. Digital analysis consisted of measuring the shortest width through the approximate center of the cell. After calibration with a known length, the diameters were measured and converted to microns using SigmaScan Pro 5.0 software (SPSS Software, Chicago, United States). Diameters were tabulated by type I and type II cell types. The counts ranged from approximately 30 cells per type to over 100 depending on the sample size. Print analysis was by similar methodology. Raw measurements in millimeters were used to calculate the ratio of Type II to Type I diameters without converting to microns.

Multiple Regression Analysis. To determine the change in expression with age, we used a multiple regression model in which the change in expression with age takes into account the possibility that age regulation might differ in men versus women, or in abdominal muscle versus peripheral muscle. Specifically, we used the following multiple regression model:

$$Y_{ij}=\beta_{0j}+\beta_{1j}Age_i+\beta_{2j}Sex_i+\beta_{3j}Anatomy_i+\epsilon_{ij}. \quad (1)$$

where, $Y_{ij}$ is the expression level of the jth probe set for the ith sample; $Age_i$ is the age in years of the ith sample; $Sex_i$ corresponds to the sex of the ith sample (0 for male, or 1 for female); $Anatomy_i$ is the anatomic location from which the muscle sample was harvested (0 for abdominal or 1 for peripheral muscle); $\epsilon_{ij}$ represents an error term; $\beta_{1j}$ is the change of expression with age; $\beta_{2j}$ is the variation of expression with sex; $\beta_{3j}$ is the variation of expression with anatomical origin of sample; and $\beta_{0j}$ is the regression intercept. For each gene, we used a least-squares method to determine its slope with respect to age ($\beta_{1j}$). We are interested in genes that show either a positive or negative value for $\beta_{1j}$, indicating either increasing or decreasing expression in old age, respectively.

The data set on mouse kidney aging measures the expression levels of 16896 genes in the kidneys from 40 mice ranging in age from 0 to 24 months. The expression data were normalized using a Z-score method.

For human brain, mouse kidney and Drosophila, we determined the change in expression with age for each gene using the following multiple regression model:

$$Y_{ij}=\beta_{0j}+\beta_{1j}Age_i+\beta_{2j}Sex_i+\epsilon_{ij}. \quad (2)$$

For human kidney, we used the multiple regression model:

$$Y_{ij}=\beta_{0j}+\beta_{1j}Age_i+\beta_{2j}Sex_i+\beta_{3j}Tissue_i+\epsilon_{ij}. \quad (3)$$

In equation 3, the tissue term is a binary term scored 0 for cortex and 1 for medulla. For C. elegans data, we used a simple linear regression with age:

$$Y_{ij}=\beta_{0j}+\beta_{1j}Age_i+\epsilon_{ij}. \quad (4)$$

Modified Gene Set Enrichment Analysis. GSEA uses a nonparametric test to decide when the n genes in a group G have age coefficients that differ significantly from the N-n genes that are not in G. The null hypothesis is that the age coefficients in G have the same distribution, F, as those that are not in G. The alternative is that there are two different distributions, F and G, with G being the distribution of age coefficients for genes in G. The Kolmogorov-Smirnov test is based on counting how many genes from G are in the top K genes of the combined list of age coefficients. By letting K vary from 1 to N, the test is sensitive to any alternative F≠G. In our analysis, we have replaced the Kolmogorov-Smirnov test by the van der Waerden normal scores test.

There is a very accurate closed form expression for the p-values of the van der Waerden test which allows us to obtain p-values without simulation. The original GSEA proposal used simulation to set p-values. If one simulates 1000 times then the cost is multiplied by a factor of 1000 and the p-values cannot be smaller than 0.001. Using near exact p-values from the van der Waerden test gives us the ability to resolve much smaller p-values without simulation.

The van der Waerden test also conforms more closely to our interpretation of what it means for a group G of genes to be age-related than does the Kolmogorov-Smirnov test. When N is large, then any small group that contains the single most age-related gene is significantly age related by the Kolmogorov-Smirnov test. Such a group displays a genuine statistical significance and comprises strong evidence that F≠G, but isn't necessarily biologically increasing or decreasing expression as a mechanistic unit with age. For example, a group of 30 genes with two of the most age-increasing genes and 2 of the most age-decreasing genes could be found to be both an age-increasing group and also an age-decreasing group with significance, even though the other 26 genes are not particularly age related. Here it is clear that F≠G, but perhaps it is simply because G has higher variance than F. The van der Waerden test is sensitive to alternatives in which all or most of G is shifted left or right relative to F, and does not allow for cases in which G is both significantly increasing and decreasing in expression with age.

In our implementation of GSEA, genes were ranked by magnitude of the slope of expression with age; thus, the gene with the most positive slope with age was accorded the highest rank when looking for gene sets increasing expression with age, whereas the gene exhibiting the most negative slope was set to highest rank when looking for gene sets with decreased expression.

Confounder analysis for GSEA. Given an experimental set of human individuals which vary in gene expression, there is a finite chance that any random ordering of the experimental set can exhibit significant regulation in one or more gene sets. This is due to the uncontrollable nature of experiments using humans, in which unknown medical and environmental factors can play a role in gene expression. In the context of this study, we wished to determine whether gene sets observed to be age-regulated were indeed regulated by aging, or instead by some other confounding factor inherent to the ordering of the 81 individuals.

To test for the presence of confounding factors, we randomly re-ordered the 81 individuals, recalculated regression coefficients, and finally recalculated GSEA enrichment scores for the 949 gene sets. The procedure was repeated 1000 times. Only in three randomizations did any gene sets meet or exceed the p-values exhibited by the age-regulated gene sets. This suggests that it is unlikely that those age-regulated gene sets observed by GSEA are associated with an unknown confounding factor inherent to the ordering of the 81 individuals ($p<0.003$).

Bootstrap Test for Significance of GSEA. We also wished to address the possibility that the population of 81 individuals sampled in this study is not representative of the total possible population, or that one or more individuals could be causing undue significance in the age-regulated gene sets. To examine this possibility, we bootstrapped the population of 81 individuals 1000 times, recalculated regression coefficients, and recalculated GSEA enrichment scores for the genetic pathways nominated as significant by GSEA. A one-sided p-value for robustness of the sample set was calculated for each gene set, with the null hypothesis asserting that the gene set is not age-regulated due to insufficient sampling of the population.

Blood Infiltration Analysis. We considered the possibility that gene sets might appear to increase expression with age if they consisted of genes that are specifically expressed in white blood cells, as levels of immune infiltration in muscle tissue increase in old age. Genes that are expressed in muscle as well as immune cells would not appear to be age-regulated due to increased inflammation with age because expression changes in immune cells would be obscured by expression in muscle since immune cells are only a small fraction of muscle tissue. In order to test whether the age-regulated pathways discussed in this paper might be caused by age-dependent inflammation, we compared the expression level of each gene in whole human blood to human skeletal muscle using the Novartis GeneAtlas to see if the most highly age-regulated genes were also those most enriched in blood cells. None of the age-regulated gene sets showed a strong correlation between age-regulation and blood expression ($r>0.5$). Therefore, age-related changes in expression from the gene sets are not caused by changes in the level of blood infiltration.

What is claimed is:

1. A method for assessing relative physiological age of a kidney sample from a human subject, the method comprising:
   determining expression information of a set of at least ten extracellular matrix protein genes associated with kidney aging selected from the group consisting of:
   TIMP1, TFPI2, TNC, EFEMP1, SPP1, CSPG2, MMP7, MMP13, CTGF, VWF, CHI3L1, THBS2, TGFBI, ADAMTS1, POSTN, COMP, THBS4, ZP2, ECM2, LTBP1, LUM, MGP, BGN, LAMA2, TIMP2, SPARCL1, TIMP4, FBN1, GPC4, LAMA5, MATN3, FLRT3, COL9A3, FBLN1, COL17A1, COL6A3, MATN2, FMOD, THBS1, LTBP2, DGCR6, LAMC1, COL6A2, ADAMTS5, MMRN2, MMP17, KAL1, FLRT2, DAG1, LAMB2, MMP2, GPC6, SOD3, MMP3, DCN, MMP9, MMP20, TNA, DMP1, EMILIN1, COL9A2, MATN1, MMP23B, DPT, ADAMTS2, NTN2L, ADAMTS17, ADAMTS20, ADAMTS15, GPC5, FBLN2, EMILIN2, ADAMTS19, MFAP1, ADAMTS14, TNXB, ADAMTS6, MFAP3, TIMP3, NYX, ADAMTS10, OMD, WNT3, ADAMTS12, LTBP4, MMP15, LAMB3, AMBN, COL14A1, USH2A, ADAMTS7, ADAMTSI3, ADAMTS4, OPTC, RBP3, PRELP, MMPL1, GPC2, MMP27, EMID2, KERA, MEPE, DSPP, GPC3, LAMC3, EMID1, MMP16, AMELX, MMP28, ENAM, NTNG1, MMP24, CHAD, COL9A1, COL6A1, SPG7, HAS1, ASPN, TECTA, NTN1, PI3, MMP25, SPOCK, ECM1, DSPG3, MMP10, GPC1, MMP12, LAMA3, CLECSF1, MMP1, ADAMTS8, ADAMTS9, SPOCK2, ADAMTS3, MMP26, LAMB4, MMP19, HAPLN2, MMP11, FBN2, CD164L1, ELN, FLRT1, NTN4, LOX, ZP4, HAPLN1, MMP8, LAMB1, AGC1, MMP21 from a sample obtained from said subject, and using said expression information to generate an age signature for said sample;
   comparing said age signature with a control age signature comprising:
       expression information of said at least ten extracellular matrix protein genes,
   wherein a statistically significant match with a positive control or a statistically significant difference from a negative control is indicative of relative age in said sample.

2. The method according to claim 1, wherein said age signature further comprises expression information for a functional group selected from cytosolic ribosomal genes and electron transport chain genes.

* * * * *